United States Patent
Donahoe et al.

(10) Patent No.: US 11,518,793 B2
(45) Date of Patent: Dec. 6, 2022

(54) MULLERIAN INHIBITING SUBSTANCE (MIS) PROTEINS FOR OVARIAN AND UTERINE ONCOPROTECTION, AND OVARIAN RESERVE AND UTERINE PRESERVATION

(71) Applicant: THE GENERAL HOSPITAL CORPORATION, Boston, MA (US)

(72) Inventors: Patricia K Donahoe, Boston, MA (US); David Pepin, Somerville, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 16/469,461

(22) PCT Filed: Dec. 14, 2017

(86) PCT No.: PCT/US2017/066346
§ 371 (c)(1),
(2) Date: Jun. 13, 2019

(87) PCT Pub. No.: WO2018/112168
PCT Pub. Date: Jun. 21, 2018

(65) Prior Publication Data
US 2020/0071376 A1 Mar. 5, 2020

Related U.S. Application Data

(60) Provisional application No. 62/434,382, filed on Dec. 14, 2016.

(51) Int. Cl.
| | | |
|---|---|---|
| C07K 14/575 | (2006.01) | |
| A61K 38/00 | (2006.01) | |
| A61K 45/06 | (2006.01) | |
| C12N 7/00 | (2006.01) | |

(52) U.S. Cl.
CPC .............. *C07K 14/575* (2013.01); *C12N 7/00* (2013.01); *A61K 38/00* (2013.01); *A61K 45/06* (2013.01); *C07K 2319/43* (2013.01); *C07K 2319/50* (2013.01); *C12N 2750/14143* (2013.01)

(58) Field of Classification Search
None
See application file for complete search history.

(56) References Cited

U.S. PATENT DOCUMENTS

| 4,753,794 A | 6/1988 | Donahoe |
| 5,010,055 A | 4/1991 | Donahoe |
| 5,661,126 A | 8/1997 | Donahoe et al. |
| 5,759,802 A | 6/1998 | Maki et al. |
| 6,428,978 B1 | 8/2002 | Olsen et al. |
| 6,673,352 B1 | 1/2004 | Donahoe et al. |
| 2003/0124620 A1 | 4/2003 | Seifer et al. |
| 2004/0062750 A1 | 1/2004 | Donahoe et al. |
| 2005/0186664 A1 | 8/2005 | Rosen et al. |
| 2006/0216294 A1 | 8/2006 | McLennan et al. |
| 2009/0304675 A1 | 12/2009 | McLennan et al. |
| 2010/0233689 A1 | 9/2010 | Teixeira et al. |
| 2013/0189327 A1 | 7/2013 | Ortega et al. |
| 2016/0039898 A1 | 2/2016 | Donahoe |
| 2016/0228514 A1 | 8/2016 | Donahoe |
| 2016/0310574 A1 | 10/2016 | Donahoe et al. |

FOREIGN PATENT DOCUMENTS

| EP | 1074265 A1 | 2/2001 |
| JP | H-02117384 A | 5/1990 |
| WO | 1988000054 A1 | 1/1988 |
| WO | 1989006695 A1 | 7/1989 |
| WO | 1992013951 A1 | 8/1992 |
| WO | 2001008695 A2 | 2/2001 |
| WO | 2001019387 A1 | 3/2001 |
| WO | 2003016514 A1 | 2/2003 |
| WO | 2005030963 A1 | 4/2005 |
| WO | 2009012357 A2 | 1/2009 |
| WO | 2014164981 A1 | 10/2014 |
| WO | 2015041718 A1 | 3/2015 |
| WO | 2015089321 A2 | 6/2015 |

OTHER PUBLICATIONS

Bhattacharya et al., PLoS One 12(3): e0171355. https://doi.org/10.1371/journal.pone.0171355; 22 pages total (Year: 2017).*
Silva et al., Autoimmunity Reviews 13 (2014) 427-430 (Year: 2014).*
Behringer et al., "Abnormal sexual development in transgenic mice chronically expressing Mullerian inhibiting susbstance", Nature 345(6271): 167-170 (1990).
Benatar et al., "Lost in translation: treatment trials in the SOD1 mouse and in human ALS", Neurobiol Dis 26(1): 1-13 (2007).
Carter et al., "Fusion partners can increase the expression of recombinant interleukins via transient transfection in 2936E cells", Protein Sci 19(2): 357-362 (2010).
Clowse et al., "Ovarian Preservation by GnRH Agonists during Chemotherapy: A Meta-Analysis", Journal of Women's Health 18(3): 311-319 (2009).
DiBernardo et al., "Translating preclinical insights into effective human trials in ALS", Biochim Biophys Acta 1762(11-12):1139-1149 (2006).

(Continued)

*Primary Examiner* — Christina M Borgeest
(74) *Attorney, Agent, or Firm* — Nixon Peabody LLP; David S. Resnick; Susanna C. Benn

(57) ABSTRACT

One aspect of the invention provides a method of ovarian protection by administering to a female subject a composition comprising Mullerian inhibiting substance (MIS). Ovarian protection can be an induced arrest of folliculogenesis to preserve fertility. In some embodiments, ovarian protection is oncoprotection, the protection of the ovarian function during a cytotoxic treatment, e.g., chemotherapy. Another aspect of the invention relates to a method of treating PCOS, the method comprising administering to a female subject a composition comprising recombinant MIS protein.

9 Claims, 34 Drawing Sheets
Specification includes a Sequence Listing.

(56) References Cited

OTHER PUBLICATIONS

Durlinger et al., "Anti-Mullerian Hormone Inhibits Initiation of Primordial Follicle Growth in the Mouse Ovary", Endocrinology 143(3): 1076-1084 (2002).
Durlinger et al., "Control of Primordial Follicle Recruitment by Anti-Mullerian Hormone in the Mouse Ovary", Endocrinology 140(12): 5789-5796 (1999).
Kano et al., "AMH/MIS as a contraceptive that protects the ovarian reserve during chemotherapy", Proc Natl Acad Sci USA 114(9): E1688-E1697 (2017).
Kurian et al., "Cleavage of Müllerian inhibiting substance activates antiproliferative effects in vivo", Clin Cancer Res 1(3): 343-349 (1995).
MacLaughlin et al., "Müllerian inhibiting substance/anti-Müllerian hormone: a potential therapeutic agent for human ovarian and other cancers", Future Oncol, 6(3): 391-405 (2010).
Maeda et al., "Efficient production of active TNF-alpha by albumin signal peptide", Biochem Mol Biol Int 42(4): 825-832 (1997).
Papakostas et al., "Development of an efficiently cleaved, bioactive, highly pure FLAG-tagged recombinant human mullerian Inhibiting Substance", Protein Expr Purif. 70(1): 32-38 (2010).
Pepin et al., "An albumin leader sequence coupled with a cleavage site modification enhances the yield of recombinant C-terminal Mullerian Inhibiting Substance", Technology 1(1): 63-71 (2013).
Pieretti-VanMarcke et al., "Mullerian Inhibiting Substance enhances subclinical doses of chemotherapeutic agents to inhibit human and mouse ovarian cancer", PNAS 103(46): 17426-17431 (2006).
Search result generated on May 17, 2017 shows Seq ID No. 3 integrated into UniProtKB/Swiss-Prot in 1986; 4 pages total.
Akira. "Ovarian Reserve." Sanfujin-ka Tiryo (Obstetrics and gynecology treatment), vol. 102, p. 547-551 (2011) [English Translation Included].
Skaar et al., "Proteolytically activated, recombinant anti-mullerian hormone inhibits androgen secretion, proliferation, and differentiation of spermatogonia in adult zebrafish testis organ cultures", Endocrinology 152(9): 3527-3540 (2011).
Teixeira et al., "Müllerian-Inhibiting Substance Regulates Androgen Synthesis at the Transcriptional Level", Endocrinology 140(10): 4732-4738 (1999).
UniProtKB MIZ-Human [online] [Retrieved on Jun. 10, 2016], Web. <URL:http:uniprot.org/uniprot/P03971.txt?version=138. (Nov. 30, 2010) Entire Document.
Zou et al., "Overexpression of human transforming growth factor-beta1 using recominant CHO cell expression system", Protein Expression and Purificaiton 37(2): 265-272 (2004).
Shulman. "Mullerian Anomalies." Clinical Obstetrics and Gynecology 51(1): 214-222 (2008).
Jafarlou et al. "An Overview of the History, Applications, Advantages, Disadvantages and Prospects of Gene Therapy." Journal of Biological Regulators & Homeostatic Agents 30(2): 315-321 (2016).
Nachtigal et al. "Bioactivation of Mullerian inhibiting substance during gonadal development by a kex2/subtilisin-like endoprotease." Proc. Natl. Acad. Sci. USA 93(15): 7711-7716 (1996).
Nakayama. "Furin: a mammalian subtilisin/Kex2p-like endoprotease involved in processing of a wide variety of precursor proteins." Biochem. J. 327(3): 625-635 (1997).
Phillips. "The challenge of gene therapy and DNA delivery." Journal of Pharmacy and Pharmacology. 53(9): 1169-1174 (2001).
Winkler. ""Oligonucleotide" conjugates for therapeutic applications." Ther. Deliv. 4(7): 791-809 (2013).
Bordo et al., "Suggestions for "safe" residue substitutions in site-directed mutagenesis." Journal of molecular biology 217.4 (1991): 721-729.

* cited by examiner

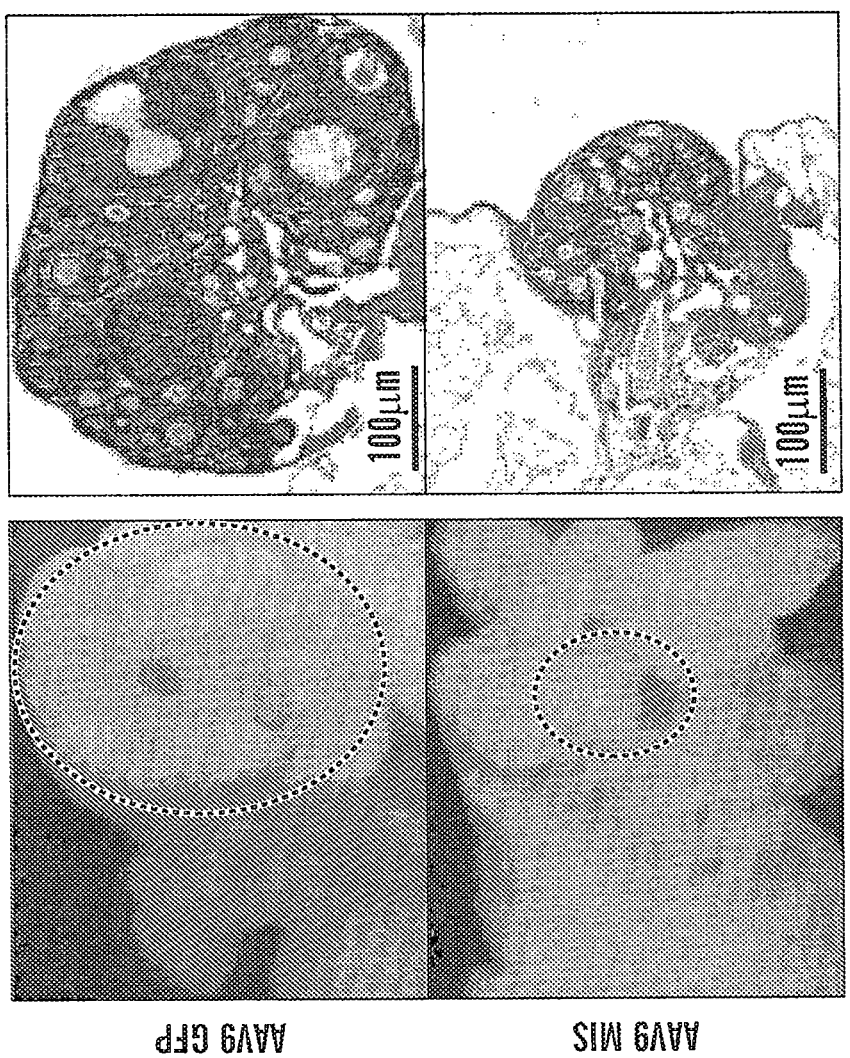

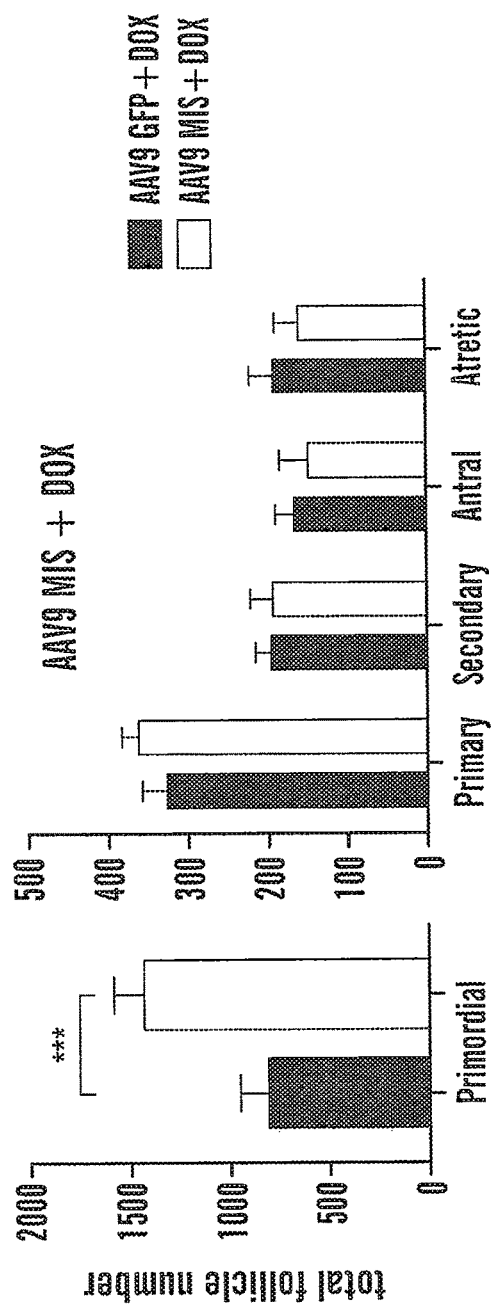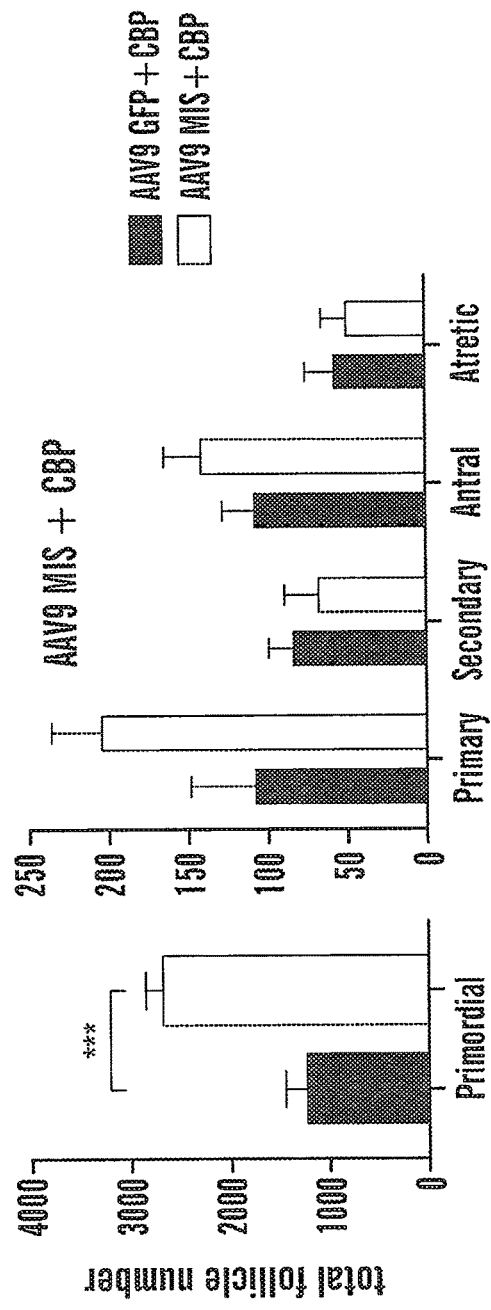
FIG. 5B
FIG. 5C

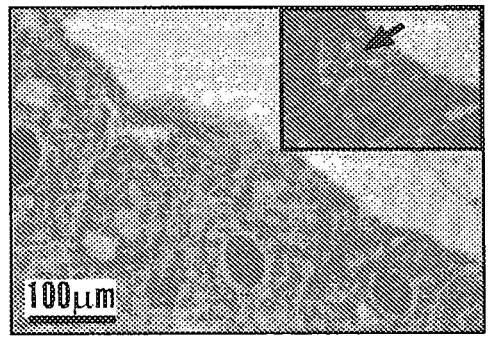 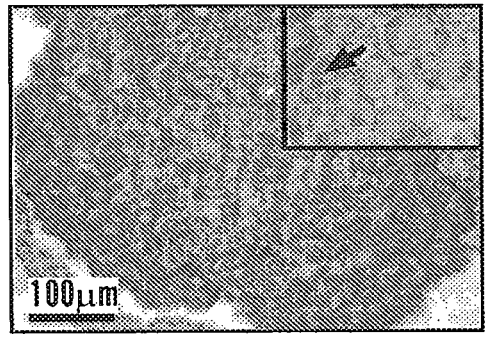
FIG. 7A  FIG. 7B
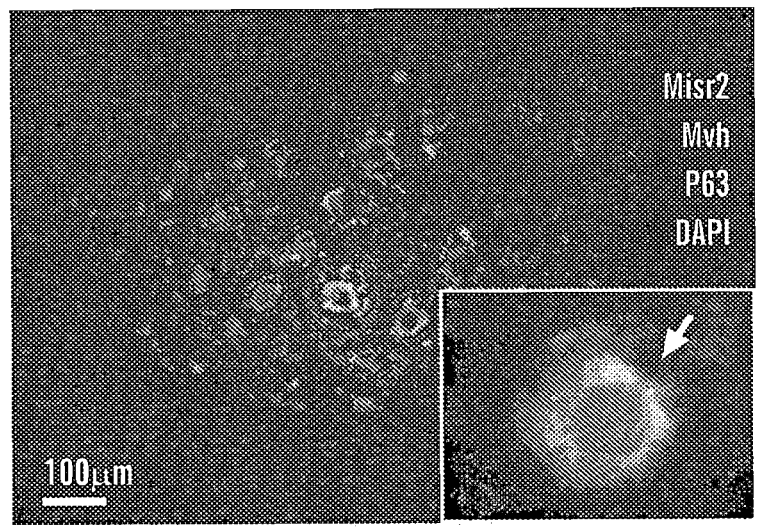
FIG. 7C

MULLERIAN INHIBITING SUBSTANCE (MIS) PROTEINS FOR OVARIAN AND UTERINE ONCOPROTECTION, AND OVARIAN RESERVE AND UTERINE PRESERVATION

CROSS-REFERENCE TO RELATED APPLICATIONS

This application is a 35 U.S.C. § 371 National Phase Entry Application of International Application No. PCT/US2017/066346 filed Dec. 14, 2017, which designates the U.S. and claims benefit under 35 U.S.C. § 119(e) of the U.S. Provisional Application No. 62/434,382 filed Dec. 14, 2016, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Dec. 14, 2017, is named 030258-088591-PCT_SL.TXT and is 24,833 bytes in size.

BACKGROUND

Mullerian Inhibiting Substance (MIS) also known as anti-Mullerian hormone (AMH), is a 140-kDa disulfide-linked homodimer glycoprotein member of the large transforming growth factor-β (TGFβ) multigene family of glycoproteins. The proteins in this gene family are all produced as dimeric precursors and undergo posttranslational processing for activation, requiring cleavage and dissociation to release bioactive C-terminal fragments. Similarly, the 140 kilodalton (kDa) disulfide-linked homodimer of MIS is proteolytically cleaved to generate its active C-terminal fragments.

MIS, is a reproductive hormone produced in fetal testes, which inhibits the development of female secondary sexual structures in males. Before sexual differentiation, the fetus is bipotential, and the developmental choice of male Wolffian ducts (i.e. prostate, vas deferens) over female Mullerian ducts (i.e. Fallopian tubes, uterus, vagina) in the male is controlled in part by MIS. In females, MIS is produced only postnatally in granulosa cells from prepuberty through menopause at levels similar to adult males, after which expression ceases. In male fetuses MIS causes regression of the Mullerian ducts, the precursors to the Fallopian tubes, uterus, cervix, and upper third of the vagina.

The ovarian reserve represents the stock of quiescent primordial follicles in the ovary which is gradually used up during a woman's reproductive lifespan, eventually triggering menopause when the pool is spent. MIS, which is produced by granulosa cells of growing follicles, has been proposed as a negative regulator of primordial follicle activation. MIS is a candidate therapeutic for regulating the rate at which primordial follicles are activated, thus controlling the ovarian reserve.

SUMMARY

During her reproductive lifespan, a woman may wish to halt, or arrest the activation of primordial follicles, as a way to preserve her fertility. This could be done, for example, to prevent premature ovarian failure caused by a cytotoxic drug or other drug treatment (e.g., a chemotherapeutic), or to preserve her ovarian reserve while undergoing a long-term treatment where she may not wish to become pregnant (e.g., a during treatment for a chronic disease or disorder, such as Lupus and the like), or until she is ready to conceive (e.g., due to relationship status, or a career or other reason). The technology described herein is based, in part, on the discovery that long-term administration of superphysiological doses of Mullerian Inhibiting Substance (MIS) protein, using either an AAV9 gene therapy vector or administration of a recombinant MIS protein, resulted in a complete arrest of folliculogenesis in mice. For example, the inventors demonstrate that mice treated with an AAV9 vector expressing a MIS protein exhibited complete and permanent contraception for their entire reproductive lifespan, disrupted vaginal cycling, and hypergonadotropic hypogonadism. However, when ovaries from AAV9 MIS treated mice were transplanted back orthotopically into normal recipient mice, or if temporary treatment with the protein was discontinued, folliculogenesis resumed, indicating that the block is reversible. Further, AAV9 MIS treatment protects the ovary from chemotherapy-induced "follicular burnout" (over recruitment of primordial follicles leading to exhaustion on ovarian reserve).

Accordingly, one aspect of the invention described herein provides a method for ovarian protection in a female subject comprising administering to the female subject a composition comprising a recombinant MIS protein, wherein the recombinant MIS protein comprises a modification of at least one amino acid between residues 448-451 of SEQ ID NO: 3 (MIS) to increase cleavage as compared to in the absence of the modification. In one embodiment, the ovarian protection is oncoprotection.

In one embodiment, the method further comprises, prior to administering, selecting a subject in need of ovarian protection and/or oncoprotection. In some embodiments, the technology described herein relates to a method for ovarian protection or oncoprotection, comprising administering to the female subject a composition comprising a recombinant MIS protein as disclosed herein, e.g., a LR-MIS protein, or a recombinant MIS protein produced from processing of the LR-MIS protein, where the produced protein is a recombinant MIS variant homodimer protein of comprising two monomers, each monomer comprising (i) a N-terminal domain of the recombinant MIS protein comprising amino acids 26-451 of SEQ ID NO: 3 (MIS) or a variant having at least 85% sequence identity thereto, where amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS) or a variant having at least 85% sequence identity thereto.

Another aspect of the invention described herein provides a method for uterine protection in a female subject, comprising administering to the female subject a composition comprising a recombinant MIS protein, wherein the recombinant MIS protein comprises a modification of at least one amino acid between residues 448-451 of SEQ ID NO: 3 (MIS) to increase cleavage as compared to in the absence of the modification. In one embodiment, the method further comprises, prior to administering, selecting a subject in need of uterine protection. In some embodiments, the technology described herein relates to a method for uterine protection, administering to the female subject a composition comprising a recombinant MIS protein as disclosed herein, e.g., a LR-MIS protein, or a recombinant MIS protein produced from processing of the LR-MIS protein, where the produced protein is a recombinant MIS variant homodimer protein of comprising two monomers, each monomer comprising (i) a N-terminal domain of the recombinant MIS protein comprising amino acids 26-451 of SEQ ID NO: 3 (MIS) or a variant having at least 85% sequence identity thereto, wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS) or a variant having at least 85% sequence identity thereto.

Another aspect of the invention described herein provides a method for treating polycystic ovarian syndrome (PCOS) in a female subject, comprising administering to the female subject a composition comprising a recombinant MIS protein, wherein the recombinant MIS protein comprises a modification of at least one amino acid between residues 448-451 of SEQ ID NO: 3 (MIS) to increase cleavage as compared to in the absence of the modification. In one embodiment, the method further comprises, prior to administering, selecting a subject in need of treatment for PCOS. In one embodiment, the method further comprises, prior to administering, selecting a subject who has previously been diagnosed with PCOS. In one embodiment, the method further comprises, prior to administering, diagnosing a subject with PCOS. In some embodiments, the technology described herein relates to a method for treatment, or prevention of PCOS in a subject, comprising administering to the female subject a composition comprising a recombinant MIS protein as disclosed herein, e.g., a LR-MIS protein, or a recombinant MIS protein produced from processing of the LR-MIS protein, where the produced protein is a recombinant MIS variant homodimer protein of comprising two monomers, each monomer comprising (i) a N-terminal domain of the recombinant MIS protein comprising amino acids 26-451 of SEQ ID NO: 3 (MIS) or a variant having at least 85% sequence identity thereto, wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS) or a variant having at least 85% sequence identity thereto.

Yet another aspect of the invention provides a method for treating polycystic ovarian syndrome (PCOS) in a female subject, comprising administering to the female subject a composition comprising a recombinant MIS protein, wherein the recombinant MIS protein comprises a modification of at least one amino acid between residues 448-451 of SEQ ID NO: 3 (MIS) to increase cleavage as compared to in the absence of the modification.

In one embodiment of all aspects, the recombinant MIS protein comprises amino acid residues 25-559 of SEQ ID NO: 4 (LR-MIS) or a polypeptide which has at least 85% sequence identity to the amino acid sequence of amino acid residues 25-559 of SEQ ID NO: 4 (LR-MIS).

In one embodiment of all aspects, the recombinant MIS protein administered to a subject is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS), wherein optionally, amino acid residue 452 of SEQ ID NO: 1 is changed from S to R.

In one embodiment of all aspects, the recombinant MIS protein does not comprise a FLAG tag.

In one embodiment of all aspects, the female subject has cancer and will be treated with, or is currently being treated with, or has been treated with, a cancer treatment selected from chemotherapy, radiotherapy, chemo-radiotherapy, or surgery. In one embodiment of all aspects, the female subject has an autoimmune disease and will be treated with, or is currently being treated with, or has been treated with, an immunotherapy.

In one embodiment of all aspects, the female subject will be treated with, or is currently being treated with, or has been treated with, a cytotoxic drug or cytotoxic agent that causes cell death or cell damage to cells in the uterus or ovary. In one embodiment of all aspects, the female subject will be treated with, or is currently being treated with, or has been treated with, a long-term treatment regimen.

In one embodiment of all aspects, ovarian protection is reducing folliculogenesis in the female subject, or reducing the number of primordial follicles being recruited by at least 10% as compared to in the absence of the recombinant MIS protein, or reducing the number of primordial follicles being recruited by between 10% and 99%, or causing a complete arrest in folliculogenesis, or slowing down of primordial follicle activation, as compared to in the absence of the recombinant MIS protein.

In one embodiment of all aspects, uterine protection is a reduction in uterine damage leading to dystocia.

In one embodiment of all aspects, treating PCOS is reducing folliculogenesis in the female subject, or reducing the number of primordial follicles being recruited by at least 10% as compared to in the absence of the recombinant MIS protein, or reducing the number of primordial follicles being recruited by between 10% and 99%, or causing complete arrest in folliculogenesis, or is a slowing down of primordial follicle activation, as compared to in the absence of the recombinant MIS protein.

In some embodiments, a recombinant MIS protein as described herein, e,g., for use in a method for any of: ovarian protection, oncoprotection, uterine protection, treatment and/or prevention of PCOS is a LR-MIS protein as described herein (e.g., amino acids 25-559 of SEQ ID NO: 4), or a recombinant MIS protein produced from processing of the LR-MIS protein, where the produced protein is a recombinant MIS variant homodimer protein of comprising two monomers, each monomer comprising (i) a N-terminal domain of the recombinant MIS protein comprising amino acids 26-451 of SEQ ID NO: 3 (MIS) or a variant having at least 85% sequence identity thereto, wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS) or a variant having at least 85% sequence identity thereto.

In some embodiments, the a recombinant MIS protein as described herein, e,g., for use in a method for any of: ovarian protection, oncoprotection, uterine protection, treatment and/or prevention of PCOS is a LR-MIS protein as described herein is administered by subcutaneous injection, or i.p. injection, either via individual injection doses or administered via a pump.

In one embodiment of all aspects, the recombinant MIS protein is administered as a continuous administration or via pulse administration (e.g., 1.5 mg/kg twice a day). Continuous administration can be via an infusion or pump administration or transdermal patch administration.

In one embodiment of all aspects, the recombinant MIS protein is administered at a high level sufficient to arrest folliculogenesis and/or keep the ovary in a quiescent state. In some embodiments, a composition comprising a MIS protein or MIS variant (e.g., LR-MIS) as described herein, or a vector expressing such a MIS variant protein is administered at superphysiological levels, such that the levels in the blood are superphysiological relative to normal levels, but is sufficient to achieve physiological MIS levels in the ovary. In some embodiments, the superphysiological levels or high levels of recombinant MIS protein can be administered between 0.001 mg/kg per hour and 0.1 mg/kg per hour, or between 0.2 µg/hr and 10.0 µg/hr. Additionally, the high levels of recombinant MIS protein can be sufficient to result in any of the following: (a) a concentration of MIS protein in the blood of the subject that is 10% to 50% higher as compared to the absence of administration of the recombinant MIS protein; (b) a concentration of MIS protein in the blood of the subject that is 50% to 100% higher as compared to the absence of administration of the recombinant MIS protein; (c) a concentration of MIS protein in the blood of the subject that is 2 to 5-fold higher or more than 5-fold higher as compared to the absence of administration of the recombinant MIS protein; or (d) a concentration of MIS protein in the blood of the subject of between 1 µg/ml-5 µg/ml.

In one embodiment of all aspects, the female subject is a human subject. In one embodiment of all aspects, the female subject is a pre-menopausal female subject. In some embodiments, the subject is a pre-pubescent female subject.

In one embodiment of all aspects, the female subject is in need of preserving their ovarian reserve, or who has a need or desire to delay reproduction to a later time point, or wherein the female subject has, or is pre-disposed to, any of the following: diminished ovarian reserve (DOR), premature ovarian aging (POA), primary ovarian insufficiency (POI), endometriosis, polycystic ovarian syndrome (PCOS), one or more FMR1 premutations or 55-200 GCC FMR1 repeats, BRAC1 mutations, turner syndrome, an autoimmune disease, thyroid autoimmunity, adrenal autoimmunity or autoimmunity polyglandular syndromes. In one embodiment of all aspects, the female subject is in need of fertility preservation.

In one embodiment of all aspects, administering the MIS protein as disclosed herein can be used in a method to prevent the female from getting pregnant; or can be used in a method as a means of temporary contraception or short-term contraception; or in a method that allows the female to control cycling and/or control of reproductive hormones, and/or slowing down primordial follicle activation.

In one embodiment of all aspects, a female subject to be administered a recombinant MIS protein as disclosed herein will undergo, or has undergone an ovarian tissue graft or cortical ovarian tissue graft.

In one embodiment of all aspects, the MIS protein (e.g., LR-MIS protein) is administered in combination with, or concurrently with a chemotherapeutic agent or anti-cancer therapy; an immunotherapy agent; or a second therapeutic. In one embodiment of all aspects, the MIS protein is administered prior to administration of a chemotherapeutic agent or anti-cancer therapy; an immunotherapy agent; or at least a second therapeutic.

An anti-cancer therapy can be, e.g., radiotherapy, chemoradiotherapy, or surgery. Exemplary chemotherapeutic agents include, but are not limited to, a platinum chemotherapeutic agent, an anthracyclin therapeutic agent, or an alkylating chemotherapeutic agent.

A second therapeutic agent can be, for example, a cytotoxic drug, or cytotoxic agent that causes cell death or cell damage to cells in the uterus or ovary.

Another aspect of the invention described herein provides a kit for use in ovarian protection, or alternatively oncoprotection, of a female subject comprising (a) an administration device, e.g., a pump or infusion device, or one or more single dose, or multi-dose pre-loaded injection syringes, or transdermal patch, comprising: (i) a recombinant MIS protein, wherein the recombinant MIS protein comprises amino acid residues 25-559 of SEQ ID NO: 4 (LR-MIS) or a polypeptide which has at least 85% sequence identity to the amino acid sequence of amino acid residues 25-559 of SEQ ID NO: 4 (LR-MIS); or (ii) a recombinant MIS protein, wherein the recombinant MIS protein is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS), wherein optionally, amino acid residue 452 of SEQ ID NO: 1 is changed from S to R; and instructions for implanting the pump or infusion device into the female subject for the treatment of a subject with one or more of: a diminished ovarian reserve (DOR), premature ovarian aging (POA), primary ovarian insufficiency (POI), endometriosis, polycystic ovarian syndrome (PCOS), one or more FMR1 premutations or 55-200 GCC FMR1 repeats, or where the subject is undergoing, has, or will undergo a cancer treatment.

Another aspect of the invention described herein provides a kit for use in uterine protection of a female subject comprising (a) an administration device, e.g., a pump or infusion device, or one or more single dose, or multi-dose pre-loaded injection syringes, or transdermal patch, comprising: (i) a recombinant MIS protein, wherein the recombinant MIS protein comprises amino acid residues 25-559 of SEQ ID NO: 4 (LR-MIS) or a polypeptide which has at least 85% sequence identity to the amino acid sequence of amino acid residues 25-559 of SEQ ID NO: 4 (LR-MIS); or (ii) a recombinant MIS protein, wherein the recombinant MIS protein is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS), wherein optionally, amino acid residue 452 of SEQ ID NO: 1 is changed from S to R; and instructions for implanting the pump or infusion device into the female subject for the treatment of a subject with one or more of: a diminished ovarian reserve (DOR), premature ovarian aging (POA), primary ovarian insufficiency (POI), endometriosis, polycystic ovarian syndrome (PCOS), one or more FMR1 premutations, premutations or 55-200 GCC FMR1 repeats, or where the subject is undergoing, has, or will undergo a cancer treatment.

Another aspect of the invention described herein provides a kit for use in treatment of polycystic ovarian syndrome (PCOS) of a female subject comprising (a) an administration device, e.g., a pump or infusion device, or one or more single dose, or multi-dose pre-loaded injection syringes, or transdermal patch, comprising: (i) a recombinant MIS protein, wherein the recombinant MIS protein comprises amino acid residues 25-559 of SEQ ID NO: 4 (LR-MIS) or a polypeptide which has at least 85% sequence identity to the amino acid sequence of amino acid residues 25-559 of SEQ ID NO: 4 (LR-MIS); or (ii) a recombinant MIS protein, wherein the recombinant MIS protein is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS), wherein optionally, amino acid residue 452 of SEQ ID NO: 1 is changed from S to R; and instructions for implanting the pump or infusion device into the female subject for the treatment of a subject with one or more of: polycystic ovarian syndrome (PCOS), one or more FMR1 premutations or 55-200 GCC FMR1 repeats, or where the subject is undergoing, has, or will undergo a cancer treatment.

In one embodiment of all aspects, the pump is an osmotic pump, e.g., an alzet pump.

In one embodiment of all aspects, the infusion device is a transdermal patch or preloaded injector or hypodermic needle. In some embodiments, an administration device is a single dose, or multi-dose pre-loaded injection syringe or autoinjector, or a syringe to insert a single dose or multi-dose canister (or ampoule) or container comprising the recombinant MIS protein as disclosed herein, where the syringe allows the dose to be adjusted prior to administration, and the syringe can have fresh needles attached prior to each injection. In such embodiments, a multi-dose injection syringe has enables the subject to adjust the dose for each administration (often referred to as an autoinjector), and attachment of a needle to the syringe. Such autoinjectors are well known in the art, and are disclosed in, e.g., U.S. Pat. Nos. 4,874,381, 4,968,229, 4,822,340, 4,874,381, 4,968, 299, 5,267,963, 6,277,097, 6,368,306, 2011/0172640, 2011/0213315 and U.S. Pat. No. 6,793,646, where U.S. Pat. No. 6,793,646 allows injection of two substances at the same time, e.g., a recombinant MIS protein as disclosed herein and another agent (e.g., second agent), e.g., a cytotoxic agent, chemotherapeutic agent or other agent.

In some embodiments, the kits as disclosed herein, e.g., for use in a method of any of: ovarian protection, oncoprotection, uterine protection, treatment and/or prevention of PCOS, can comprise an administration device, e.g., a pump or infusion device, or single pre-loaded injection syringes, or transdermal patch, comprising: a LR-MIS protein as described herein (e.g., amino acids 25-559 of SEQ ID NO: 4), or a recombinant MIS protein produced from processing of the LR-MIS protein, where the produced protein is a recombinant MIS variant homodimer protein of comprising two monomers, each monomer comprising (i) a N-terminal domain of the recombinant MIS protein comprising amino acids 26-451 of SEQ ID NO: 3 (MIS) or a variant having at least 85% sequence identity thereto, wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS) or a variant having at least 85% sequence identity thereto.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "Mullerian Inhibiting Substance" and "MIS" are used interchangeably herein and is also known as anti-Müllerian hormone or AMH, refer to compounds and materials which are structurally similar to MIS. By "MIS" or "Mullerian Inhibiting Substance" is meant a polypeptide having an amino acid sequence at least about 60%, or at least about 70%, or at least about 80%, or at least about 90%, or at least about 95%, or at least about 96%, or at least about 97%, or at least about 98%, or at least about 99% identical to amino acid residues 26-560 of SEQ ID NO: 3. The present invention is intended to include mutant forms of recombinant human MIS which have substantially the same, or greater biological activity as wild-type MIS. Examples of such mutant MIS molecules carrying a deletion, insertion, or alteration in the amino acid sequence of wild-type MIS (e.g., amino acid residues 26-560 of SEQ ID NO:3). Other forms of include substances are for example, salts, functional derivatives and aglycone forms of wild-type MIS and recombinant human MIS. Additionally, human recombinant MIS protein can be obtained using recombinant DNA technology, or from chemical synthesis of the MIS protein. For reference purposes only, the wild-type human MIS nucleic acid corresponds to Ref Seq No: NM_000479, which are incorporated herein by reference.

The term "Mullerian Inhibiting Substance type II receptor" or "MISRII" are used interchangeably herein to refer to the type II receptor for MIS. The term MISRII is intended to encompass all MIS receptors substantially homologous to MISRII and functional derivatives of MISRII. MISRII is also known by the alias as AMHR2, and for reference purposes, the nucleic acid sequence of human MISRII corresponds to NM_020547 and GenBank No: AF172932 which are incorporated herein by reference The term "wild type" refers to the naturally-occurring polynucleotide sequence encoding a protein, or a portion thereof, or protein sequence, or portion thereof, respectively, as it normally exists in vivo. Accordingly, as disclosed herein, the wild type amino acid sequence for the pre-proprotein of human MIS corresponds to SEQ ID NO: 3, where amino acid residues 1-25 correspond to the leader sequence. The proprotein of MIS comprises amino acid residues 26-560 of SEQ ID NO: 3 (e.g., lacking the 1-25 leader sequence), which is then post-translationally processed by cleavage as discussed herein to form a bioactive MIS homodimer.

The term "soluble MIS polypeptide" as used herein refers to a MIS polypeptide that does not comprise at least part of, or all of, the amino acids which allow it to functionally bind to the membrane.

By a "polynucleotide encoding MIS" is meant a polynucleotide encoding a polypeptide having at least about 60%, or at least about 70%, or at least about 80%, or at least about 90%, or at least about 95%, or at least about 96%, or at least about 97%, or at least about 98%, or at least about 99% sequence identity to any of the amino acid sequences corresponding to amino acid residues 26-560 of SEQ ID NO: 3.

The term "mutant" refers to any change in the genetic material of an organism, in particular a change (i.e., deletion, substitution, addition, or alteration) in a wild-type polynucleotide sequence or any change in a wild-type protein sequence. The term "variant" is used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent). The term mutation is used interchangeably herein with polymorphism in this application.

The term "nucleic acid" is well known in the art. A "nucleic acid" as used herein will generally refer to a molecule (i.e., strand) of DNA, RNA or a derivative or analog thereof, comprising a nucleobase. A nucleobase includes, for example, a naturally occurring purine or pyrimidine base found in DNA (e.g. an adenine "A," a guanine "G." a thymine "T" or a cytosine "C") or RNA (e.g. an A, a G. an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. The term "nucleic acid" also refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. The terms "polynucleotide sequence" and "nucleotide sequence" are also used interchangeably herein.

As used herein, the term "gene" refers to a nucleic acid comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. These definitions generally refer to a single-stranded molecule, but in specific embodiments will also encompass an additional strand that is partially, substantially or fully complementary to the single-stranded molecule. Thus, a nucleic acid may encompass a double-stranded molecule or a double-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "is." The term "gene" refers to the segment of DNA involved in producing a polypeptide chain, it includes regions preceding and following the coding region as well as intervening sequences (introns) between individual coding segments (exons). A "promoter" is a region of a nucleic acid sequence at which initiation and rate of transcription are controlled. It may contain elements at which regulatory proteins and molecules may bind, such as RNA polymerase and other transcription factors, to initiate the specific transcription of a nucleic acid sequence. The term "enhancer" refers to a cis-acting regulatory sequence involved in the transcriptional activation of a nucleic acid sequence. An enhancer can function in either orientation and may be upstream or downstream of the promoter.

The terms "polypeptide" and "protein" are used interchangeably to refer to a polymer of amino acid residues, and are not limited to a minimum length. Peptides, oligopeptides, dimers, multimers, and the like, are also composed of linearly arranged amino acids linked by peptide bonds, and whether produced biologically, recombinantly, or synthetically and whether composed of naturally occurring or non-naturally occurring amino acids, are included within this definition. Both full-length proteins and fragments thereof are encompassed by the definition. The terms also include co-translational and post-translational modifications of the polypeptide, such as, for example, disulfide-bond formation, glycosylation, acetylation, phosphorylation, proteolytic cleavage (e.g., cleavage by furins or metalloproteases and prohormone convertases (PCs)), and the like. Furthermore, for purposes of the present invention, a "polypeptide" encompasses a protein that includes modifications, such as deletions, additions, and substitutions (generally conservative in nature as would be known to a person in the art), to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. Polypeptides or proteins are composed of linearly arranged amino acids linked by peptide bonds, but in contrast to peptides, has a well-defined conformation. Proteins, as opposed to peptides, generally consist of chains of 50 or more amino acids. For the purposes of the present invention, the term "peptide" as used herein typically refers to a sequence of amino acids of made up of a single chain of D- or L-amino acids or a mixture of D- and L-amino acids joined by peptide bonds. Generally, peptides contain at least two amino acid residues and are less than about 50 amino acids in length.

The incorporation of non-natural amino acids, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. In some embodiments, a recombinant human MIS protein is comprised of D- or L-amino acid residues, as use of naturally occurring L-amino acid residues has the advantage that any break-down products should be relatively non-toxic to the cell or organism.

The term "fragment" of a peptide, polypeptide or molecule as used herein refers to any contiguous polypeptide subset of the molecule. The term "protein fragment" as used herein includes both synthetic and naturally-occurring amino acid sequences derivable from MIS proteins of SEQ ID NO:3 or 4 or 5. The protein fragment can be obtained by fragmenting the recombinant human MIS protein, or if it can be synthesized based upon a knowledge of the sequence of the naturally occurring amino acid sequence or of the genetic material (DNA or RNA) which encodes this sequence. Accordingly, a "fragment" of a molecule, is meant to refer to any polypeptide subset of the molecule. In some embodiments, a functional fragment of recombinant human MIS comprises at least the C-terminal domain and at least the N-terminal domain. In some embodiments, a functional fragment comprises a portion of the C-terminal and/or a portion (e.g., fragment) of the N-terminal domain of the recombinant human MIS protein. Fragments of a recombinant human MIS protein which have the activity at least or greater than the MIS protein of SEQ ID NO: 3, 4, or 5 as disclosed herein and which are soluble are also encompassed for use in the present invention.

Fragments of a recombinant human MIS protein, for example functional fragments of SEQ ID NO: 3, 4 or 5 useful in the methods as disclosed herein have at least 30% the activity as that of a polypeptide of SEQ ID NO: 3, 4 or 5 in vivo, e.g., to cause inhibition of follicologenesis as disclosed herein. Stated another way, a functional fragment of a recombinant human MIS protein is a fragment of any of SEQ ID NO: 3, 4 or 5 which, alone or as a fusion protein can result in at least 30% of the same activity as compared to SEQ ID NO: 3, 4 or 5 to bind and activate MISRII, or inhibit follicle maturation as disclosed herein. Fragments as used herein can be soluble (i.e. not membrane bound). A "fragment" can be at least about 6, at least about 9, at least about 15, at least about 20, at least about 30, least about 40, at least about 50, at least about 100, at least about 250, at least about 300 nucleic or amino acids, and all integers in between. Exemplary fragments include C-terminal truncations, N-terminal truncations, or truncations of both C- and N-terminals (e.g., deletions of, for example, at least 1, at least 2, at least 3, at least 4, at least 5, at least 8, at least 10, at least 15, at least 20, at least 25, at least 40, at least 50, at least 75, at least 100 or more amino acids deleted from the N-termini, the C-termini, or both). One of ordinary skill in the art can create such fragments by simple deletion analysis. Such a fragment of SEQ ID NO: 3, 4 or 5 can be, for example, 1, 2, 3, 4, 5, 6, 7, 8, 9 or 10 amino acids or more than 10 amino acids, such as 15, 30, 50, 100 or more than 100 amino acids deleted from the N-terminal and/or C-terminal of SEQ ID NO: 3, 4 or 5, respectively. Persons of ordinary skill in the art can easily identify the minimal peptide fragment of SEQ ID NO: 3, 4 or 5 useful in the methods and compositions as disclosed herein, or fusion proteins as disclosed herein, by sequentially deleting N- and/or C-terminal amino acids from SEQ ID NO: 3, 4 or 5, or sequentially deleting N- and C-terminal amino acids from recombinant human MIS protein and assessing the function of the resulting peptide fragment, alone or when it is cleaved. One can create functional fragments with multiple smaller fragments. These can be attached by bridging peptide linkers. One can readily select linkers to maintain wild type conformation. In some embodiments, a fragment must be at least 6 amino acids, at least about 9, at least about 15, at least about 20, at least about 30, at least about 40, at least about 50, at least about 100, at least about 250, at least about 500 continuous nucleic acids or amino acids, or any integers in between.

The term "derivative" as used herein refers to peptides which have been chemically modified, for example but not limited to by techniques such as ubiquitination, labeling, pegylation (derivatization with polyethylene glycol) or addition of other molecules. A molecule also a "derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

The term "functional" when used in conjunction with "derivative" or "variant" or "fragment" refers to a polypeptide which possess a biological activity (either functional or structural) that is substantially similar to a biological activity of the polypeptide which it is a functional derivative, variant or functional fragment thereof. The term functional derivative is intended to include the fragments, analogues or chemical derivatives of a molecule. By "substantially similar" in this context is meant that the biological activity, e.g., activation of MISRII is at 25% or at least 35%, or at least 50% as active as a reference polypeptide, e.g., a corresponding wild-type MIS polypeptide or recombinant human MIS protein, and preferably at least 60% as active, 70% as active, 80% as active, 90% as active, 95% as active, 100% as active or even higher (i.e., the variant or derivative has greater activity than the wild-type), e.g., 110% as active, 120% as active, or more. Stated another way, a "substantially similar" functional fragment of a recombinant human MIS protein in this context is meant that at least 25%, at least 35%, at least 50% of the relevant or desired biological activity of a corresponding recombinant human MIS protein is retained. In the instance of a functional fragment or peptide of a recombinant human MIS protein as disclosed herein (e.g., SEQ ID NO: 3, 4 or 5), a functional fragment of SEQ ID NO: 3, 4 or 5 would be a protein or peptide comprising a portion of SEQ ID NO: 3, 4 or 5 which retained an activity to activate MISRII, or inhibit follicle maturation as disclosed herein; preferably the fragment of SEQ ID NO: 3, 4 or 5 that retains at least 25%, at least 35%, at least 50% at least 60%, at least 70%, at least 80%, at least 90%, at least 95%, at least 100% or even higher (i.e., the variant or derivative has greater activity than a MIS protein of SEQ ID NO: 3 or of a recombinant human MIS protein of SEQ ID NO 4 or 5), e.g., at least 110%, at least 120%, or more activity compared to MIS proteins corresponding to SEQ ID NO: 3, 4 or 5.

The term "functional derivative" and "mimetic" or "biologically active variant" or "biologically active fragment" are used interchangeably, and refers to a compound which possess a biological activity (either functional or structural) that is substantially similar to a biological activity of the entity or molecule its is a functional derivative of (e.g., the recombinant human MIS protein). The term functional derivative is intended to include the fragments, variants, analogues or chemical derivatives of a molecule.

The term "functional derivatives" is intended to include the "fragments," "variants," "analogs," or "chemical derivatives" of a molecule. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical. An "analog" of a recombinant human MIS protein is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

A "variant" of a recombinant human MIS protein is meant to refer to a molecule substantially similar in structure and function to either the entire molecule, or to a fragment thereof. Accordingly, the term "variant" as used herein refers to a peptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size. Substitutions encompassed by the present invention may also be "non conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide). A "variant" of a recombinant human MIS protein is meant to refer to a molecule substantially similar in structure and function, i.e. where the function is the ability to activate MISRII.

For example, a variant of a recombinant human MIS protein can contain a modification that differs from a reference amino acid in SEQ ID NO: 3, 4 or 5. In some embodiments, a variant of SEQ ID NO: 3, 4 or 5 is a fragment of SEQ ID NO: 3, 4 or 5 as disclosed herein. In some embodiments, a variant can be a different isoform of SEQ ID NO: 3, 4 or 5 or can comprise different isomer amino acids. Variants can be naturally-occurring, synthetic, recombinant, or chemically modified polynucleotides or polypeptides isolated or generated using methods well known in the art. Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of omithine which do not normally occur in human proteins.

The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to reduce T-reg cells and/or decrease inflammatory cytokines as disclosed herein). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In some embodiments, individual substitutions, deletions or additions that alter, add or delete a single amino acid or a small percentage of amino acids can also be considered "conservative substitutions" is the change does not reduce the activity of the MIS protein (i.e. the ability of a recombinant human MIS protein or variant to cause Mullerian duct regression in vivo, which can be determined using the Mullerian Duct regression bioassay as disclosed herein). Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119 (1986); 205-218 and S. French and B. Robson, J. Mol. Evol. 19 (1983) 171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants. A variant of a recombinant human MIS protein, for example a variant of SEQ ID NO: 3, 4 or 5 is meant to refer to any molecule substantially similar in structure and function to either the entire molecule of SEQ ID NO: 3, 4 or 5, or to a fragment thereof.

The terms "homology", "identity" and "similarity" refer to the degree of sequence similarity between two peptides or between two optimally aligned nucleic acid molecules. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with the sequences as disclosed herein.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or I) or residue occurs in both sequences to yield the number of matched positions, dividing the number of matched positions by the total number of positions in the comparison window (i.e., the window size), and multiplying the result by 100 to yield the percentage of sequence identity.

The terms "substantial identity" as used herein denotes a characteristic of a polynucleotide or amino acid sequence, wherein the polynucleotide or amino acid comprises a sequence that has at least 85% sequence identity, preferably at least 90% to 95% sequence identity, more usually at least 99% sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. Determination of homologs of the genes or peptides of the present invention can be easily ascertained by the skilled artisan.

The term "substantially homologous" refers to sequences that are at least 90%, at least 95% identical, at least 96%, identical at least 97% identical, at least 98% identical or at least 99% identical. Homologous sequences can be the same functional gene in different species. Determination of homologs of the genes or peptides of the present invention can be easily ascertained by the skilled artisan.

A molecule is said to be "substantially similar" to another molecule if both molecules have substantially similar structures or if both molecules possess a similar biological activity, for example if both molecules are able to activate MISRII or inhibit ovarian follicle maturation. Thus, provided that two molecules possess a similar activity, (i.e. a variant of a recombinant human MIS protein which can activate MISRII similar to that of the MIS protein which corresponds to SEQ ID NO: 3, or recombinant human MIS protein which corresponds to SEQ ID NO: 4 or 5) are considered variants and are encompassed for use as disclosed herein, even if the structure of one of the molecules not found in the other, or if the sequence of amino acid residues is not identical. Thus, provided that two molecules possess a similar biological activity, they are considered variants as that term is used herein even if the structure of one of the molecules not found in the other, or if the sequence of amino acid residues is not identical. As such, nucleic acid and amino acid sequences having lesser degrees of similarity but comparable biological activity to recombinant human MIS protein are considered to be equivalents. In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a specific nucleic acid sequence of SEQ ID NO:1 or 2 as disclosed herein if: (a) the nucleotide sequence is hybridizes to the coding regions of the natural MIS nucleic acid, or (b) the nucleotide sequence is capable of hybridization to nucleotide sequence of a recombinant human MIS protein encoded by SEQ ID NO: 1 or 2 under moderately stringent conditions and has biological activity similar to the recombinant human MIS protein; or (c) the nucleotide sequences which are degenerative as a result of the genetic code to the nucleotide sequences defined in (a) or (b). Substantially similar proteins will typically be greater than about 80% similar to the corresponding sequence of the native protein.

The term "substantial similarity" in the context of polypeptide sequences, indicates that the polypeptide comprises a sequence with at least 60% sequence identity to a reference sequence, or 70%, or 80%, or 85% sequence identity to the reference sequence, or most preferably 90% identity over a comparison window of about 10-20 amino acid residues. In the context of amino acid sequences, "substantial similarity" further includes conservative substitutions of amino acids. Thus, a polypeptide is substantially similar to a second polypeptide, for example, where the two peptides differ by one or more conservative substitutions.

In one embodiment, the term "human homolog" to a gene transcript refers to a DNA sequence that has at least about 55% homology to the full length nucleotide sequence of the sequence of a recombinant human MIS protein gene as encoded by the genome of humans or an animal, for example mouse or transgenic animal. In one embodiment, the term "human homolog" to a protein identified as associated with a recombinant human MIS protein refers to an amino acid sequence that has 40% homology to the full length amino acid sequence of the protein identified as associated with a recombinant human MIS protein as encoded by the genome of the transgenic animal of the present invention, more preferably at least about 50%, still more preferably, at least about 60% homology, still more preferably, at least about 70% homology, even more preferably, at least about 75% homology, yet more preferably, at least about 80% homology, even more preferably at least about 85% homology, still more preferably, at least about 90% homology, and more preferably, at least about 95% homology. As discussed above, the homology is at least about 50% to 100% and all intervals in between (i.e., 55%, 60%, 70%, 75%, 80%, 85%, 90%, 95%, 98%, etc.). Determination of the human homologs of the genes of the present invention may be easily ascertained by the skilled artisan.

As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

The term "insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "substitution" when referring to a peptide, refers to a change in an amino acid for a different entity, for example another amino acid or amino-acid moiety. Substitutions can be conservative or non-conservative substitutions.

An "analog" of a molecule such as a recombinant human MIS protein, for example SEQ ID NO: 4 or 5 refers to a molecule similar in function to either the entire molecule or to a fragment thereof. The term "analog" is also intended to include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; acedisubstituted amino acids, N-alkyl amino acids, lactic acid, 4-hydroxyproline, β-carboxyglutamate, ε-N,N,N-trimethyllysine, ε-N-acetyllysine, O-phosphoserine, N-acetylserine, N-formylmethionine, 3-methylhistidine, 5-hydroxylysine, ε-N-methylarginine. Fragments and analogs can be screened for prophylactic or therapeutic efficacy in transgenic animal models as described below.

By "covalently bonded" is meant joined either directly or indirectly (e.g., through a linker) by a covalent chemical bond.

The term "fusion protein" as used herein refers to a recombinant protein of two or more proteins. Fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. As a non-limiting example, the nucleic acid sequence encoding the recombinant human MIS-fusion protein is derived from the nucleotide sequence of encoding a recombinant human MIS protein or a functional derivative fragment or variant thereof, fused in frame to an end, either the 5' or the 3' end, of a gene encoding a first fusion partner, such as a IgG1 Fc fragment. In this manner, on expression of the gene, the recombinant human MIS protein or functional derivative fragment or variant thereof is functionally expressed and fused to the N-terminal or C-terminal end of the IgG1 Fc. In certain embodiments, modification of the polypeptide probe is such that the functionality of the recombinant human MIS protein or a functional derivative fragment or variant thereof remains substantially unaffected in terms of its biological activity by fusion to the first fusion partner, such as IgG1 Fc.

By "specifically binds" or "specific binding" is meant a compound or antibody that recognizes and binds a desired polypeptide but that does not substantially recognize and bind other molecules in a sample, for example, a biological sample, which naturally includes a polypeptide of the invention.

By "substantially pure" or is meant a nucleic acid, polypeptide, or other molecule that has been separated from the components that naturally accompany it. Typically, a polypeptide is substantially pure when it is at least about 60%, or at least about 70%, at least about 80%, at least about 90%, at least about 95%, or even at least about 99%, by weight, free from the proteins and naturally occurring organic molecules with which it is naturally associated. For example, a substantially pure polypeptide may be obtained by extraction from a natural source, by expression of a recombinant nucleic acid in a cell that does not normally express that protein, or by chemical synthesis.

By "enhanced proteolytic stability" is meant a reduction of in the rate or extent of proteolysis of a peptide sequence by at least about 2%, at least about 5%, at least about 10%, at least about 20%, at least about 30%, at least about 40%, at least about 50%, at least about 60%, at least about 70%, at least about 80%, at least about 85%, at least about 90%, at least about 95%, at least about 98%, or at least about 99% as compared to a control sequence under the same conditions (e.g., in vivo or in an in vitro system such as in a cell or cell lysate). A peptide with enhanced proteolytic stability may contain any modification, for example, insertions, deletions, or point mutations which reduce or eliminate a site subject to proteolytic cleavage at a particular site. Sites of proteolytic cleavage may be identified based on known target sequences or using computer software (e.g., software described by Gasteiger et al., Protein Identification and Analysis Tools on the ExPASy Server. In John M. Walker, ed. The Proteomics Protocols Handbook, Humana Press (2005)). Alternatively, proteolytic sites can be determined experimentally, for example, by Western blot for the protein following expression or incubation in a cellular system or cellular lysate, followed by sequencing of the identified fragments to determine cleavage sites.

The term "recombinant" as used herein to describe a nucleic acid molecule, means a polynucleotide of genomic, cDNA, viral, semisynthetic, and/or synthetic origin, which, by virtue of its origin or manipulation, is not associated with all or a portion of the polynucleotide with which it is associated in nature. The term recombinant as used with respect to a protein or polypeptide, means a polypeptide produced by expression of a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The terms "subject" and "individual" are used interchangeably herein, and refer to an animal, for example a human, to whom treatment, including prophylactic treatment, with the pharmaceutical composition according to the present invention, is provided. As used herein, a "subject" means a human or animal. Usually the animal is a vertebrate such as, but not limited to a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. A subject is preferably female. Additionally, a subject can be an infant or a child. A subject can be of child-bearing age (e.g., 20 to 35 years old), a teenager (e.g., 13-19 years old), or pre-pubescent (e.g., 6-12 years old). A female subject can be older than 35 years old.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with autoimmune disease or inflammation. In addition, the methods and compositions described herein can be used for domesticated animals and/or pets. A human subject can be of any age, gender, race or ethnic group, e.g., Caucasian (white), Asian, African, black, African American, African European, Hispanic, Mideastern, etc. In some embodiments, the subject can be a patient or other subject in a clinical setting. In some embodiments, the subject can already be undergoing treatment.

As used herein, the terms "administering," and "introducing" are used interchangeably herein and refer to the placement of the recombinant MIS protein, or an agent or vector expressing the recombinant MIS protein as disclosed herein into a subject by a method or route which results in at least partial localization of a recombinant MIS protein at a desired site. The compounds of the present invention can be administered by any appropriate route which results in blocking folliculogenesis in the subject.

The term "effective amount" as used herein refers to the amount of a recombinant human MIS protein as disclosed herein, to alleviate at least one or more symptom of the disease or disorder, and relates to a sufficient amount of pharmacological composition to provide the desired effect. The phrase "therapeutically effective amount" as used herein, e.g., a pharmaceutical composition comprising at least one recombinant human MIS protein as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylacticly significant reduction in a symptom or clinical marker associated with a cancer or a cancer-mediated condition. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of fertility, and any treatment or administration of the compositions or formulations that leads to preventing pregnancy, or arresting folliculogenesis indicates effective treatment.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

The term "prophylactically effective amount" refers to an amount of a recombinant human MIS protein or functional fragment or variant thereof which is effective, at dosages and for periods of time necessary, to achieve the desired prophylactic result, e.g., to prevent pregnancy or prevent decrease in follicle ovarian reserve (FOR) in the female subject. In some embodiments, a prophylactically effective amount is less than the therapeutically effective amount (e.g., for the treatment of a subject who has or is at risk of POA or DOR. A dose of MIS or MIS protein variant for contraceptive measures (e.g., prophylactic effective amount) may be higher than the prophylactic amount for preventing a decrease in ovarian reserve (e.g., for preventing a decrease in follicle ovarian reserve (FOR). A prophylactically effective amount of a recombinant human MIS protein or functional fragment or variant thereof is also one in which any toxic or detrimental effects of the compound are outweighed by the beneficial effects.

As used herein, the terms "prevent," "preventing" and "prevention" refer to the avoidance or delay in manifestation of one or more symptoms or measurable markers of a disease or disorder, e.g., of POA or DOR (diminished ovarian reserve). A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the avoidance or prevention of a symptom or marker of the disease, but also a reduced severity or degree of any one of the symptoms or markers of the disease, relative to those symptoms or markers in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

A "composition" or "pharmaceutical composition" are used interchangeably herein refers to a composition that usually contains an excipient, such as a pharmaceutically acceptable carrier that is conventional in the art and that is suitable for administration to cells. The cells may be part of a subject, for example for therapeutic, diagnostic, or prophylactic purposes. The cells may also be cultured, for example cells as part of an assay for screening potential pharmaceutical compositions, and the cells may be part of a transgenic animal for research purposes. The composition can also be a cell culture, in which a polypeptide or polynucleotide encoding a metabolic regulator of the present invention is present in the cells and/or in the culture medium. In addition, compositions for topical (e.g., oral mucosa, respiratory mucosa) and/or oral administration can form solutions, suspensions, tablets, pills, capsules, sustained-release formulations, oral rinses, or powders, as known in the art and described herein. The compositions also can include stabilizers and preservatives. For examples of carriers, stabilizers and adjuvants, University of the Sciences in Philadelphia (2005) Remington: *The Science and Practice of Pharmacy with Facts and Comparisons,* 21st Ed.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule.

The term "vector" refers to a nucleic acid molecule capable of transporting another nucleic acid to which it has been linked; a plasmid is a species of the genus encompassed by "vector". The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA loops which, in their vector form are not bound to the chromosome, and typically comprise entities for stable or transient expression or the encoded DNA. Other expression vectors can be used in the methods as disclosed herein for example, but are not limited to, plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self-replicating extrachromosomal vectors or vectors which integrates into a host genome. Preferred vectors are those capable of autonomous replication and/or expression of nucleic acids to which they are linked. Vectors capable of directing the expression of genes to which they are operatively linked are referred to herein as "expression vectors". Expression vectors can result in stable or transient expression of the DNA. An exemplary expression vector for use in the present invention is pcDNA3.1.

The term "viral vectors" refers to the use as viruses, or virus-associated vectors as carriers of the nucleic acid construct into the cell. Constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells. The vector may or may not be incorporated into the cells genome. The constructs may include viral sequences for transfection, if desired. Alternatively, the construct may be incorporated into vectors capable of episomal replication, e.g., EPV and EBV vectors.

The term "inducible vector" refers to a vector whose gene expression can be controlled. For example, the level of gene expression can be increased, decreased, or reduced to zero. In some embodiments, the inducible vector can comprise a switch that controls gene expression.

As used herein, a "promoter" or "promoter region" or "promoter element" used interchangeably herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated. A promoter can refer to a tissue specific promoter (e.g., specific for expression on the ovary, or uterus).

The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, inducible promoters and transcriptional elements, an optional operate sequence to control transcription, a sequence encoding suitable mRNA ribosomal binding sites, and sequences to control the termination of transcription and/or translation. Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

The term "operatively linked" as used herein refers to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined Enhancers need not be located in close proximity to the coding sequences whose transcription they enhance. Furthermore, a gene transcribed from a promoter regulated in trans by a factor transcribed by a second promoter may be said to be operatively linked to the second promoter. In such a case, transcription of the first gene is said to be operatively linked to the first promoter and is also said to be operatively linked to the second promoter.

The terms "decrease", "reduced", "reduction", or "inhibit" are all used herein to mean a decrease by a statistically significant amount. In some embodiments, the terms "reduced", "reduction", "decrease", or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or up to between about 90-95% or 90-99% decrease or any decrease of at least 10%-95% or 10-99% as compared to a reference level.

The term "statistically significant" or "significantly" refers to statistical significance and generally means a two standard deviation (2SD) or greater difference.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

DESCRIPTION OF THE DRAWINGS

FIG. 1A shows rat fetal (E14.5) urogenital ridges were incubated ex-vivo with recombinant protein (right column), and the contralateral ridge mock treated (left column) for 72 h. Representative sections from ridges treated with fresh rhMIS (LR-MIS) protein at 5 µg/ml top row, LR-MIS recovered from a pump implanted for one week in a mouse at 5 µg/ml middle row, or commercial C-terminal MIS (R&D systems) protein produced in $E\ coli$ at 5 µg/ml. Regressed (top and middle rows), or intact (bottom row) Mullerian ducts are indicated with arrows. Pharmacokinetics of MIS administered by different delivery routes with serum levels of MIS measured serially with a human specific ELISA including FIG. 1B shows results of s.c. bolus injection at 3 mg/kg (N=3), FIG. 1C shows results of i.v. bolus injection 3 mg/kg (N=3), FIG. 1D shows results after AAV9 MIS 3E11 particles/mouse (N=5), FIG. 1E shows results of i.p. bolus injection 1.5 mg/kg (N=3), FIG. 1F shows results of implanted i.p. osmotic pump delivering 0.6 µg/h of rhMIS protein. FIG. 1G is a representative western blot of MIS protein showing holo (70 kDa) and cleaved c-terminal (12.5 kDa) peptides from tissue lysates of a mouse injected with 3E11 particles of AAV9 MIS with CHOK1-LRMIS conditioned media as a positive control, and uninjected (WT) muscle lysate as a negative control.

FIGS. 2A-2E present experimental showing that AAV9 MIS treatment results in reversible ovarian quiescence. Mice were treated with a single dose of AAV9 MIS at 3E11 particles per mouse, and ovaries examined after 39 days. FIG. 2A shows representative images of gross morphology (ovary circled with dashed line) and FIG. 2B shows representative images of the middle section compared to an AAV9-GFP control ovary. FIG. 2C shows the total follicle counts of (N=5) AAV9 MIS and (N=5) AAV9 GFP mice 39 days after treatment with a single dose of 3E11 viral particles. Statistical significance indicated by * $p<0.05$,  $p<0.01$, and * $p<0.001$ by student t-test. FIG. 2D shows a schematic of the scheme of transplants of ovaries from AAV9 MIS treated (60 days) mice into AAV9 GFP or AAV9 MIS control recipients. FIG. 2E shows representative images of middle sections from transplanted ovaries (middle row) or intact contralateral ovaries (top row) from 4 donor mice, 12 days after transplantation into either AAV9 GFP or MIS recipients. Higher magnification of growing follicles indicated by arrows (bottom left panels), or quiescent primordial follicles (bottom right panels).

FIG. 3A shows representative images of middle sections from ovaries of mice at d0, d3, d5, d10, and d15 post-treatment (top row, left to right), and higher magnification examples of quiescent primordial (bottom 2 left panels), or growing (bottom 3 right panels) follicles. FIG. 3B shows the total follicle counts from ovaries of mice treated with (left to right) AAV9-MIS as a positive control of complete quiescence, rhMIS protein for 35 days and released for 0 days (d0), 3 days (d3), 5 days (d5), 10 days (d10), 15 days (d15), or treated with saline for 35 days as negative control with normal folliculogenesis (control). FIG. 3C shows the serum MIS levels as measured by ELISA during the 35 days of s.c. treatment with 1.5 mg/kg of rhMIS protein, taken at the trough (12 h after injection). FIG. 3D shows the results of simulation of the pharmacokinetics of s.c. administration of 1.5 mg/kg of rhMIS protein every 12 h over a 24 h interval.

FIG. 4A shows MIS levels in cycling was monitored by daily vaginal swabs over 70 days. FIG. 4B shows the relative amount of time spent in estrus was compared for the first half (d0-d35) and second half (d36-d70) of the observation period in both groups. FIG. 4C shows the mating trios (N=10 trios) consisting of a proven male breeder with an AAV9 MIS and an AAV9 empty vector control female were continuously housed together for a 6 month interval, and the average cumulative number of pups per female compared by ANOVA with a Holm-Sidak post-hoc test (p-value indicated). FIG. 4D shows AAV9 MIS treated females were split into two groups, AAV9 MIS high and low, based their serum levels of MIS, as measured by ELISA, being above or below the 0.25 µg/ml threshold respectively for the duration of the experiment. FIG. 4E shows levels of LH, FSH, T, P4, INHB, and E2 in the serum (measured by ELISA) following the 6 month breeding experiment. Statistical significance indicated by * $p<0.05$,  $p<0.01$, and * $p<0.001$ by student t-test.

FIGS. 5A-5H show experimental data showing that treatment with MIS protects the ovarian reserve from the follicular burnout induced by chemotherapy. FIG. 5A show mice that were treated with a single injection of 3E11 particles of AAV9 MIS or AAV9 GFP control and one day later started weekly chemotherapy, and were sacrificed either 3 (DOX) or 5 days (CBP) after the second chemotherapeutic injection. FIG. 5B shows total follicle counts were performed for (N=5) AAV9 MIS and (N=5) AAV9 GFP mice treated 80 mg/kg CBP i.p. FIG. 5C shows total follicle counts were performed for (N=5) AAV9 MIS and (N=5) AAV9 GFP mice treated 3 mg/kg DOX i.v. and analyzed by 2-way ANOVA with a Holm-Sidak post-hoc test. FIG. 5D is a representative image of the middle section from a CBP (AAV9-GFP) treated ovary at endpoint stained by H&E, with a representative cleaved caspase-3 IHC-stained follicle in the insert. FIG. 5E show the schematic of mice were implanted i.p. with pumps delivering either rhMIS protein at 0.6 µg/h or saline as a negative control, which were replaced every 5 or 7 days. One day after the implantation of the pump weekly rounds of chemotherapy started, and mice were sacrificed one week after the last dose of chemotherapy. FIG. 5F-5H show the total follicle counts were performed for (N=5) saline pump+saline i.p. controls, (N=5) rhMIS protein pump+saline i.p. controls, (N=5) saline pump+chemotherapy i.p., and (N=5) rhMIS protein pump+chemotherapy i.p. FIG. 5F shows protection with DOX 7.5 mg/kg i.p., FIG. 5G shows protection with CBP 60 mg/kg i.p., and FIG. 5H shows protection with CPA 60 mg/kg i.p. Average follicle counts were analyzed by 2-way ANOVA with a Holm-Sidak post-hoc test with statistical significance indicated by * $p<0.05$,  $p<0.01$, and * $p<0.001$.

FIGS. 7A-7F present experimental data showing treatment modality validation. 0 FIGS. 7A-7C show ovaries from adult mice (FIG. 7A) or neonatal d5 mouse pups (FIG. 7B) stained by IHC for MISR2, with representative examples of primordial follicles in the inserts. FIG. 7C shows neonatal d10 mouse ovaries sectioned and stained for Misr2 (green), Mvh (red), P63 (purple) and DAPI (blue). Representative primordial follicles in the insert in FIG. 7C. FIG. 7D show viral titrations from 1E10 to 1E12 viral particles of AAV9-MIS (or 3E11 GFP control), with serial serum analysis for circulating rhMIS by a human-specific ELISA. FIG. 7E shows the total follicle counts 60 days after administration of the titrated viral particles. FIG. 7F shows the average number of pups produced per female during a 1-mo mating period at 12 mo of age in n=10 females treated with either AAV9-MIS or AAV9-empty control at 7 wk of age. **$P<0.01$ by Student's t test.

FIG. 9A shows the total cumulative litters per female. Statistical analysis of p-value derived by Mann-Whitney test. FIG. 9B shows that dystocia, which is a lethal adverse-side effect/complication of doxorubicin, was experienced in half of the control animals, whereas the mice received recombinant MIS protein did not experience dystocia. Kaplan-Meier plots indicates the occurrences of dystocia during the experiment. p-value by Chi-squared test.

FIG. 16A shows an immunoblot of tissue protein lysates from animals treated with AAV9-empty vector or AAV9-MIS probed for the expression of MIS (murine and human) and β-actin. FIG. 16B shows the average change in endogenous murine MIS levels, as measured by ELISA, comparing pretreatment and posttreatment serum concentrations (14 d after two weekly doses of saline, DOX, CBP, or CPA) in individual mice (n=3 per group). *$P<0.05$ by Student's t test compared with saline control.

DETAILED DESCRIPTION

Figure 1A:
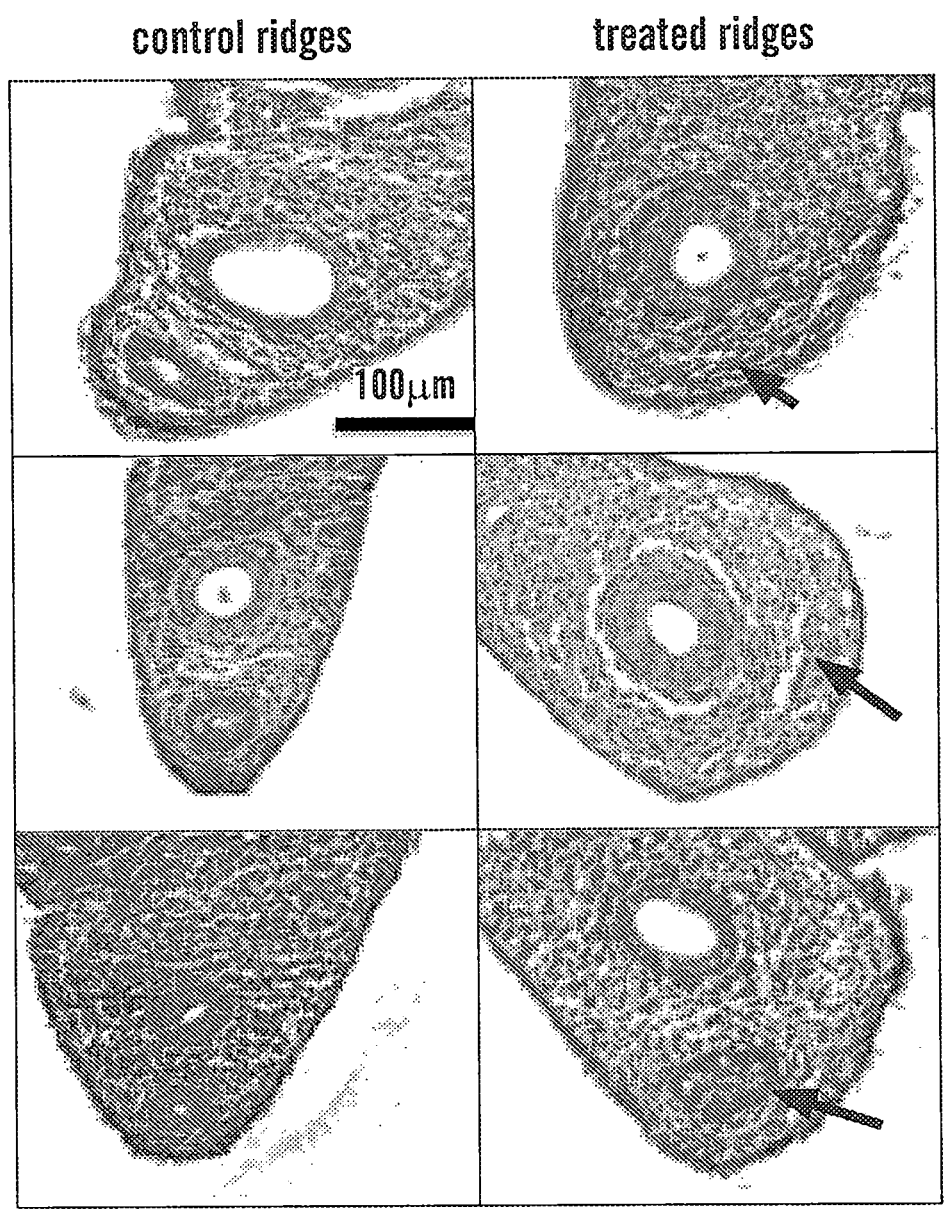
FIGS. 1A-1G present experimental data showing comparative analysis of multiple modes of administration of MIS.

All reversible hormonal contraceptive methods in the clinic rely on modulating gonadotropins or sex steroids by acting on the hypothalamic-pituitary-gonadal axis. Primordial follicle activation, the first step of folliculogenesis, is independent of gonadotropins and steroids. Long-term administration of Mullerian Inhibiting Substance (MIS), using either an AAV9 gene therapy vector or recombinant protein, arrested folliculogenesis in mice. AAV9 MIS treated mice exhibited complete contraception while receiving MIS protein, however, folliculogenesis resumed when administration was stopped, indicating that the block is reversible. Controlling primordial follicle recruitment with MIS represents an ideal mechanism of contraception since, unlike current contraceptives, it would spare the germ cells, thus retaining the ovarian reserve for later reproductive use, and averting primary ovarian insufficiency. Thus, MIS provides a novel paradigm of a treatment that can provide contraception, or when given concurrently with a therapeutic that can elicit a deleterious effect on the ovarian reserves, (e.g., a chemotherapeutic), mitigates secondary damage to the ovarian reserve associated with gonadotoxic chemotherapeutics.

Mullerian Inhibiting Substance (MIS)

Without wishing to be bound by theory, the Mullerian Inhibiting Substance (MIS) is a member of the TGFβ multigene family of glycoproteins. The proteins in this gene family are all produced as dimeric precursors and undergo posttranslational processing for activation, requiring cleavage and dissociation to release bioactive C-terminal fragments. MIS is a 140-kDa dimer which consists of identical 70 kDa disulfide-linked monomers, each composed of a 57 kDa N-terminal domain and a 12.5 kDa carboxyl-terminal (C-terminal). Thus, MIS comprises 2 identical monomers (and thus is termed a "homodimer"), each monomer comprising two domains, the N-terminal and C-terminal domain, which are held in non-covalent association. The purified C-terminal domain is the biologically active moiety and cleavage is required for activity. The N-terminal domain may assist with protein folding in vivo and facilitate delivery of the C-terminal peptide to its receptor, e.g., MISRI and MISRII. A non-cleavable mutant of MIS is biologically inactive.

The carboxy-terminal active domain shares amino acid homology with other TGFβ family members, such as TGFβ 1, 2, and 3, inhibin, activin, and bone morphogenetic proteins, as well as a member of Growth and Differentiation Factors (GDFs). The structure of the MIS carboxy-terminal domain is supported by seven cysteines involved both in intra- and intermolecular disulfides bridges that lead to its structural stability, as revealed by homology to the three dimensional structure of TGFβ using molecular modeling (Lorenzo, Donahoe, et al., unpublished data).

Like other TGFβ family members, MIS can be cleaved by plasmin which generates its amino- and carboxy-terminal domains. This proteolytic process is required for its physiological activity and occurs at a site in a position similar to the dibasic cleavage site found in the sequence of TGFβ. The resultant products are tightly associated in a non-covalent complex that dissociates at low pH; therefore, technically complex and time-demanding protocols with plasmin treatment and molecular size exclusion chromatography are required to enhance or complete the separation of the carboxy terminus from the amino terminus.

Processing of the mature MIS protein involves the proteolytic cleavage and removal of the leader sequence (e.g., amino acids 1-25 of SEQ ID NO: 3), the cleavage of the MIS protein at the primary site to generate the N-terminal and C-terminal domains, and the formation of these domains into a monomer, which is disulfide linked by inter- and intrachain disulfide bonds to an identical monomer to form the bioactive homodimer MIS protein.

MIS contains two major cleavage sites that are sensitive to plasmin and result in difficult and complex purification of recombinant human MIS protein. There is a primary monobasic cleavage site is Q/R which is located at amino acid position 426-427 of human wild-type MIS protein (where the leader sequence has been cleaved) (the RAQ/R cleavage site corresponds to amino acid 448-451 of SEQ ID NO: 3, which is the wild type hMIS protein including the leader sequence of 1-25 of SEQ ID NO: 3). Cleavage at this site, which releases the active carboxy-terminal domain of MIS, resembles a consensus furin cleavage site. A secondary cleavage site (referred to as "R/S"), is identified by amino-terminal sequencing of MIS fragments is located at residues 229-230 in the amino-terminal domain of wild-type MIS (corresponding to amino acids 254-255 of SEQ ID NO: 3). This site contains an R/S, but otherwise does not follow the consensus Arg-X-(Arg/Lys)-Arg for furin cleavage. Separation of purified carboxy-terminal from amino-terminal MIS after digestion with exogenous plasmin previously used molecular size-exclusion chromatography under acidic conditions. This technique requires extreme care to control MIS digestion, since long incubations of MIS in plasmin produced the carboxy-terminal MIS domain plus other fragments of 22 and 34 kDa, due to cleavage both at the primary and secondary sites, are extremely difficult to separate from one another by size exclusion. Since all fragments generated after plasmin digestion are glycosylated, except the carboxy-terminal domain, wheat-germ lectin affinity can be used as an alternative to size chromatography separation to purify the carboxy-terminal domain of MIS. After plasmin cleavage, the resulting fragments can be loaded onto a wheat germ lectin column at pH 3.5 in order to dissociate the amino- and carboxy-terminal domains, as disclosed in Lorenzo et al., J. Chromatography, (2001), 776; 89-98, which is incorporated herein its entirety by reference.

In order to make purification easier and to prevent the production of MIS fragments during purification, (e.g., where both the carboxy-terminal MIS domain plus a 22 and 34 kDa fragment are produced due to cleavage both at the primary and secondary sites), the inventors previously developed a modified recombinant MIS protein (herein referred to as "LR-MIS" and corresponds to SEQ ID NO: 4) where the primary RAQ/R cleavage site at amino acid position 426-427 of human wild-type MIS (corresponding to amino acid 448-451 of SEQ ID NO:3 herein) was changed to RAQ/R. This is disclosed in PCT application PCT/US14/024010 and U.S. patent application Ser. No. 15/103,568, which are incorporated herein in its entireties by reference, where the inventors previously demonstrated that changing the Q at position 450 of SEQ ID NO:3 herein to a R allowed production of a highly purified cleaved preparation of human MIS protein that has full bioactivity.

Accordingly, in all aspects of the invention, a MIS protein for use in the method, compositions and kits as disclosed herein can be wild-type MIS comprising at least one modification between residues 448-451 of SEQ ID NO: 3, or alternatively, can be a recombinant MIS protein comprising amino acid residues 25-559 of SEQ ID NO: 4 (e.g., LR-MIS), or a polypeptide which has at least 85% sequence identity to the amino acid sequence of amino acid residues 25-559 of SEQ ID NO: 4. In one embodiment, a MIS protein for use in the method, compositions and kits as disclosed herein can be or a polypeptide which has at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to the amino acid sequence of amino acid residues 25-559 of SEQ ID NO: 4.

As discussed above, the mature wild-type MIS protein is initially produced as a prohormone comprising a N-terminal leader sequence, which corresponds to amino acid residues 1-25 of wild-type MIS protein of SEQ ID NO: 3. This leader sequence is cleaved off to render the mature MIS protein. In all aspects of the invention, a MIS protein or a nucleic acid sequence encoding the same for use in the method, compositions and kits as disclosed herein can have a non-endogenous MIS leader sequence, where the MIS leader sequence of amino acids 1-25 of SEQ ID NO: 3 has been replaced with different leader sequence, such as, for example, a human serum albumin leader sequences. In all aspects of the invention, a MIS protein or a nucleic acid sequence encoding the same for use in the method, compositions and kits as disclosed herein is a modified recombinant MIS protein (herein referred to as "LR-MIS") and corresponds to SEQ ID NO:4 where the primary RAQ/R cleavage site at amino acid position 426-427 of human wild-type MIS (corresponding to amino acid 448-451 of SEQ ID NO:3 herein) was changed to RAR/R, and where the endogenous MIS leader sequence has been replaced with an albumin leader sequence.

In some embodiments, a MIS protein or a nucleic acid sequence encoding the same for use in the method, compositions and kits as disclosed herein is a modified recombinant MIS protein comprising at least amino acids 25-559 of SEQ ID NO: 4 (where the primary RAQ/R cleavage site has been changed to RAR/R) and any suitable N-terminal leader sequence, such as those disclosed in PCT application PCT/US14/024010, which is incorporated herein in its entirety by reference.

Different non-endogenous leader sequences often improve the expression and/or secretion of a polypeptide of interest in a host cell, and are useful for the production of recombinant proteins. Generally, as an efficient method for production of a desired protein by a genetic engineering procedure involves it secretion from a cell, where the procedure involves the expression of a fused protein, e.g., comprising the desired protein (e.g., MIS) and a prepropeptide (signal peptide+propeptide) in a host cell and then its intracellular cleavage (e.g., processing) by enzymes of the host, followed by its extracellular secretion. According to this process, the fused protein must be cleaved twice by enzymes of the host to be a mature protein, resulting in lower yield of the mature protein and contamination of the mature protein with residual fused protein.

Accordingly, secreted proteins are expressed initially inside the cell in a precursor form containing a leader sequence ensuring entry into the secretory pathway. Such leader sequences, also referred to as signal peptides, direct the expressed product across the membrane of the endoplasmic reticulum (ER). Signal peptides are generally cleaved off by signal peptidases during translocation to the ER. Once entered in the secretory pathway, the protein is transported to the Golgi apparatus. From the Golgi the protein can follow different routes that lead to compartments such as the cell vacuole or the cell membrane, or it can be routed out of the cell to be secreted to the external medium (Pfeffer and Rothman (1987) Ann. Rev. Biochem. 56:829-852).

For industrial production of a secreted protein, the protein to be produced needs to be secreted efficiently from the host cell or the host organism. The signal peptide may be, e.g., the native signal peptide of the protein to be produced, a heterologous signal peptide, or a hybrid of native and heterologous signal peptide. However, several problems are encountered with the use of currently known signal peptides. One problem often encountered when producing a human protein from a non-human host cell or organism is that the native signal peptide does not ensure efficient translocation and/or cleavage of the signal peptide. This leads to low rates of protein secretion and/or to secretion of mature proteins that display N-terminal extensions due to an incorrect cleavage of the signal peptide. Thus the choice of the signal peptide is of great importance for industrial production of a protein.

In addition of leader sequences directing the secretion of the protein, a precursor form can comprise supplemental leader sequences that are cleaved during maturation. These supplemental leader peptides, named propeptides, usually follow the signal peptide. Virtually all peptide hormones, numerous bioactive protein (for example, growth factors, receptors and cell-adhesion molecules, and including MIS), and many bacterial toxins and viral envelope glycoproteins comprise a propeptide that is post-translationally excised to generate the mature and biologically active protein (Seidah and Chretien (1999) Brain Res. 848:45-62).

Peptides are further cleaved by enzymes named proprotein convertases. Mammalian proprotein convertases include, e.g., the subtilisin convertases PCSK1, PCSK2 and furin. Furin is ubiquitously expressed and located in the trans-Golgi network. Furin proteolytically activates large numbers of proproteins substrates in secretory pathway compartments. (Thomas (2002) Nat Rev Mol Cell Biol. 3:753-766). More specifically, furin localizes to the Trans Golgi Network, a late Golgi structure that is responsible for sorting secretory pathway proteins to their final destinations, including the cell surface, endosomes, lysosomes and secretory granules. The site that furin cleaves has been extensively studied. The cleavage site is positioned after the carboxyl-terminal arginine of the consensus sequence R-X-L/R-R, wherein X may represent any amino acid (Nakayama (1997) Biochem. J 327:625-635). The cleavage efficiency is increased when X is a lysine, a valine, an isoleucine or an alanine (Watanabe et al (1992) J Biol. Chem. 267:8270-8274).

In some embodiments, the recombinant human MIS protein comprises a modified leader sequence in place of the wild-type leader sequence of the MIS protein corresponding to amino acid residues 1-25 of SEQ ID NO:3. In some embodiments, the native leader sequence of amino acid residues 1-25 of SEQ ID NO: 3 is replaced with a non-MIS leader sequence, for example, but not limited to an albumin leader sequence, or functional fragment thereof. In some embodiments, the non-MIS leader sequence is a human serum albumin sequence (HSA), for example, a leader sequence corresponding to SEQ ID NO: 6 (i.e. amino acids 1-24 of SEQ ID NO: 4), which is encoded by nucleic acids of SEQ ID NO: 7 (i.e., nucleic acids 1-78 of SEQ ID NO: 1).

In some embodiments, a HSA sequence is a functional fragment of SEQ ID NO: 6, for example, or at least 23, or at least 22, or at least 21, or at least 20, or at least 19, or at least 18, or at least 17, or at least 16, or at least 15, or at least 14, or at least 13, or at least 12, or at least 11, or at least 10, or less than 10 consecutive or non-consecutive amino acids of SEQ ID NO:6. Modified versions of HSA leader sequence are also encompassed for use in the present invention and are disclosed in U.S. Pat. No. 5,759,802 which is incorporated herein in its entirety by reference. In some embodiments, a functional fragment of HSA leader sequence is MKWVTFISLLFLFSSAYS (SEQ ID NO: 9) or variations therefor, which are disclosed in EP patent EP2277889 which is incorporated herein in its entirety. Variants of the pre-pro region of the HSA signal sequence (e.g., MKWVTFISLLFLFSSAYSRGVFRR, SEQ ID NO: 6) include fragments, such as the pre region of the HSA signal sequence (e.g., MKWVTFISLLFLFSSAYS, SEQ ID NO:9) or variants thereof, such as, for example, MKWVSFISLLFLFSSAYS, (SEQ ID NO: 10).

In some embodiments, the leader sequence is a leader sequence is at least about 60%, or at least about 70%, or at least about 80%, or at least about 90%, or at least about 95%, or at least about 96%, or at least about 97%, or at least about 98%, or at least about 99% identical to amino acid residues of SEQ ID NO: 6.

The HSA leader sequence as used herein has been demonstrated to produce an unexpected increased yield (both higher concentration and higher production) of the recombinant human MIS protein (see FIGS. 2 and 3 of PCT/US14/024101). However, the presence of the HSA leader sequence also resulted in a surprising and unexpected increase in cleavage from the primary cleavage site (corresponding to cleavage at 450/451 of SEQ ID NO: 3. This increased yield and increased cleavage was surprising because with an increased yield (and therefore more protein produced by the cell), one would expect a decreased cleavage as the activity of the available cleavage enzymes becomes saturated and overextended. However, this was not the case—in fact the exact opposite occurred where with increased protein production there was increased cleavage from the primary cleavage site.

Other leader sequences are encompassed for use in a recombinant human MIS protein as disclosed herein, e.g., to replace amino acids 1-25 of SEQ ID NO: 3. Such leader sequences are well known in the art, and include the leader sequences comprising an immunoglobulin signal peptide fused to a tissue-type plasminogen activator propeptide (IgSP-tPA), as disclosed in US 2007/0141666, which is incorporated herein in its entirety by reference. Numerous other signal peptides are used for production of secreted proteins. One of them is a murine immunoglobulin signal peptide (IgSP, EMBL Accession No. M13331). IgSP was first identified in 1983 by Loh et al. (Cell. 33:85-93). IgSP is known to give a good expression in mammalian cells. For example. EP patent No. 0382762 discloses a method of producing horseradish peroxidase by constructing a fusion polypeptide between IgSP and horseradish peroxidase.

Other leader sequences include, for example, but not limited to, the MPIF-1 signal sequence (e.g., amino acids 1-21 of GenBank Accession number AAB51134) MKVSVAALSCLMLVTALGSQA (SEQ ID NO: 11); the stanniocalcin signal sequence (MLQNSAVLLLLVISASA, SEQ ID NO: 12); the invertase signal sequence (e.g., MLLQAFLFLLAGFAAKISA, SEQ ID NO: 13); the yeast mating factor alpha signal sequence (e.g., K. lactis killer toxin leader sequence); a hybrid signal sequence (e.g., MKWVSFISLLFLFSSAYSRSLEKR, SEQ ID NO:14); an HSA/MFα-1 hybrid signal sequence (also known as HSA/kex2) (e.g., MKWVSFISLLFLFSSAYSRSLDKR, SEQ ID NO: 15); a K. lactis killer/MFα-1 fusion leader sequence (e.g., MNIFYIFLFLLSFVQGSLDKR, SEQ ID NO: 16); the Immunoglobulin Ig signal sequence (e.g., MGWSCIIL-FLVATATGVHS, SEQ ID NO: 17); the Fibulin B precursor signal sequence (e.g., MERAAPSRRVPLPLLLLGGLAL-LAAGVDA, SEQ ID NO: 18); the clustering precursor signal sequence (e.g., MMKTLLLFVGLLLTWESGQVLG, SEQ ID NO: 19); and the insulin-like growth factor-binding protein 4 signal sequence (e.g., MLPLCLVAALL-LAAGPGPSLG, SEQ ID NO: 20).

Where it is desirable to produce recombinant MIS in a bacterial system, leader sequences can include bacterial leader sequences as disclosed in US Application 2011/0020868. A number of other secretion signals have been described for use in expressing recombinant polypeptides or proteins. See, for example, U.S. Pat. Nos. 5,914,254; 4,963, 495; European Patent No. 0 177 343; U.S. Pat. No. 5,082, 783; PCT Publication No. WO 89/10971; U.S. Pat. Nos. 6,156,552; 6,495,357; 6,509,181; 6,524,827; 6,528,298; 6,558,939; 6,608,018; 6,617,143; 5,595,898; 5,698,435; and 6,204,023; 6,258,560; PCT Publication Nos. WO 01/21662, WO 02/068660 and U.S. Application Publication 2003/0044906; U.S. Pat. No. 5,641,671; and European Patent No. EP 0 121 352, which are incorporated herein in their entirety by reference.

In further embodiments, a MIS protein or a nucleic acid sequence encoding the same for use in the method, compositions and kits as disclosed herein also comprises a tag to aid purification. Tags are well know in the art and disclosed in PCT application PCT/US14/024010, which is incorporated herein in its entirety by reference. Protein tags are useful to aid the purification of the C-terminal domain without the need for complicated methods using wheat-germ lectin affinity or size chromatography columns. The inventors also previously added a tag (e.g., a Flag tag) at the N-terminus of the C-terminal domain, to produce a "LRF-MIS" variant corresponding to SEQ ID NO: 5. Any protein tag is encompassed for use herein, and are disclosed in PCT/US14/024010, which is incorporated herein in its entirety by reference.

In some embodiments, a recombinant MIS protein comprises at least one internal label or "tag". In some embodiments the tag can be, for example, a c-myc, poly histidine, or FLAG tag. In some embodiments, the tag is a FLAG tag, for example, a FLAG tag of SEQ ID NO: 8. A FLAG tag can be encoded by the nucleic acid of SEQ ID NO: 8. A flag tag can be removed from a recombinant MIS protein, for example, by use of an enterokinase that facilitates site specific proteolytic cleavage of FLAG peptide from N-terminal and Met-N-terminal fusion proteins (Item No: E5144; Millipore-Sigma, St. Louis, Mo.). In one embodiment, the recombinant MIS protein does not comprise a FLAG tag.

In some embodiments, the tag on the recombinant human MIS protein is internal at the carboxy terminus immediately downstream from the cleavage site. As it is the most flexible part of the C-terminus and not involved in binding to receptor and rendering specificity, as are the "fingertips" of the C-terminus (Papakostas et al, 2010, Lorenzo et al, 2002). In some embodiments, the labeling at this site is most likely to preserve biologic activity. In some embodiments, a tag, e.g., a FLAG tag is located after the primary cleavage site, e.g., after amino acid 450 of SEQ ID NO: 3 (corresponding to amino acid residue 425 of conventional protein nomenclature). In some embodiments, a tag is located between amino acid residues 452 and 453 of SEQ ID NO: 3 (which corresponds with amino acid residues 427 and 428 under normal amino acid nomenclature of MIS protein).

In alternative embodiments, the tag or label is located at any position between sequence 450 and 560 of SEQ ID NO: 3. In some embodiments, the tag is inserted 2 amino acid residues after the modified amino acid at position 450 of SEQ ID NO: 3. However, a position of the tag at the N-terminus of the C-terminal domain of MIS is preferred, as it location at the C-terminus of the C-terminal domain renders the C-terminal domain totally inactive, significantly reducing the bioactivity of the MIS protein.

In some embodiments, a recombinant MIS protein comprises more than one tag, e.g., for example, at least 2 or at least 3, or at least 4 or more than 4 tags. In some embodiments, the tags are sequential (e.g., one after another) and in some embodiments, they are dispersed (e.g., intermittent) in the recombinant human MIS protein. Preferably, the tags do not interfere or substantially affect the bioactivity of the recombinant MIS protein function at binding and activating MISRII. In some embodiments, where the recombinant MIS protein comprises more than one tag, the tags are the same tag. In alternative embodiments, where the recombinant MIS protein comprises more than one tag, the tags are different tags, for example, a recombinant MIS protein can comprise a FLAG tag and a histidine tag. The small size of the Flag tag allows it to be contained in the flexible, non binding N-terminal domain of the C-terminus. Accordingly, in some embodiments, any tag known to a person of ordinary skill in the art can be used in place of the Flag Tag, for example a tag of between about 5-10 amino acids, or between about 10-15 amino acids, or a tag between about 15-20 amino acids, or a tag between 20-30 amino acids, or a tag between about 30-50 amino acids. In some embodiments, a tag greater than 50 amino acids in length is not recommended, as the tag may sterically hinder the flexible N-terminus of the C-terminal domain, and thus inhibit the bioactivity of the recombinant MIS protein.

In some embodiments, a tag-labeled, e.g., FLAG tagged recombinant human MIS protein, such as the LRF recombinant human MIS protein as disclosed herein can be eluted by a single step to produce highly purified efficiently cleaved preparation with full bioactivity. When scaled-up, this purification of recombinant human MIS protein will be suitable for clinical applications; furthermore it will be useful for various binding assays in both clinical and experimental settings. Internal labeling of MIS during translation has proved to be more effective than labeling after purification of the protein as iodination or biotinylation greatly reduced MIS bioactivity. Surprisingly, the inventors have discovered that the LRF recombinant human MIS protein construct is more bioactive than the wild-type MIS. Inserting the FLAG tag sequence has several other distinct advantages. First, its unique amino acid domain is not present in any other gene (except for mouse brain phosphatase), thus making the anti-FLAG antibody very specific. Second, the elution of the protein with the 3× FLAG peptide is specific for the FLAG MIS and not other proteins that bind non-specifically to the agarose beads.

In some embodiments, a labeled recombinant human MIS protein, e.g., a MIS with an internal FLAG is useful in an efficient method for producing a highly pure and biologically active internally labeled form of MIS, which can be used for scale-up for preclinical and clinical use, for the study of MIS binding proteins and for tracking in pharmacokinetic studies.

As discussed above, MIS proteins useful in the methods as disclosed herein can be wild-type MIS, or MIS variants, such as LR-MIS, LRF-MIS and the like. Such LR-MIS and LRF-MIS protein variants are non-naturally occurring proteins and produced by recombinant means, e.g., by expression from a nucleic acid in vitro expression system as disclosed herein.

Therapeutic Uses of Recombinant MIS Protein

MIS for Ovarian Protection

In one embodiment, a recombinant MIS protein described herein is administered to a female subject as a method of ovarian protection. As used herein, "ovarian protection" refers to the protection against deleterious or adverse effects on one or both ovaries as a result of trauma, damage or the effect of an exogenous agent, e.g., a therapeutic agent or treatment. In some embodiments, an exogenous agent can be a chemotherapeutic agent or cytotoxic agent. "Ovarian protection" can also refer to the protection against any insult or trauma to the ovaries (e.g., an engraftment, or an injury). Ovarian protection can refer to the protection of one or both ovaries. "Ovarian protection" refers to protecting the function of the ovaries (e.g., produce reproductive hormones, maintain proper levels of follicle stimulating hormone, or follicle production), and the histology of the ovaries (e.g., size, and tissue health). Ovarian protection maintains at least 99%, at least 95%, at least 90%, at least 80%, at least 70%, at least 60%, at least 50%, at least 40%, at least 30%, at least 20%, at least 10% of the ovarian function following administration of a therapeutic agent of treatment, as compared to the ovarian function prior to said administration. Ovarian protection also encompasses protection of the ovaries due to damage during a cancer treatment, i.e., a MIS protein described herein can be used for oncoprotection.

Accordingly, in some embodiments, a recombinant MIS protein described herein is administered to a female subject as a method of oncoprotection. The term "oncoprotection" as used herein refers to the protection of an ovary or both ovaries during a treatment for cancer. Non-limiting examples of treatments for cancer include administration of a chemotherapeutic, radiotherapy, chemo-radiotherapy, targeted-cancer therapies, e.g., immunotherapy, CART cells, immune checkpoint inhibitors, recession surgery, or a combination thereof.

In some embodiments, ovarian protection can be a reduction of folliculogenesis. Folliculogenesis is the maturation of the ovarian follicle which contains the immature oocyte, and is the progression of a number of small primordial follicles into large preovulatory follicles as part of the menstrual cycle. Depletion of the primordial follicles or primordial follicles that respond to hormonal cues, signals the beginning of menopause. By reducing folliculogenesis, the primordial follicles are preserved. Ovarian protection can reduce folliculogenesis in the female subject, or reduce the number of primordial follicles being recruited by at least 10%, at least 20%, at least 30%, at least 40%, at least 50%, at least 60%, at least 70%, at least 80%, at least 90%, at least 99%, or more as compared to in the absence of the recombinant MIS protein. Ovarian protection can slow the rate of primordial follicle activation by at least 10%, at least 20%, at least 30%, at least 40%, at least 50%, at least 60%, at least 70%, at least 80%, at least 90%, at least 99%, or more as compared to in the absence of the recombinant MIS protein. "Completed arrest" of folliculogenesis refers to a reduction of 100% of primordial follicles being recruited and/or activation compared to in the absence of the recombinant MIS protein.

In some embodiments, ovarian protection can be an inhibition of premature ovarian failure. As used herein, "premature ovarian failure" refers to the cessation of the ovarian function prior to the age of 40. Clinically, premature ovarian failure is diagnosed by high levels of follicle stimulating hormone and luteinizing hormone in the blood. Causes of premature ovarian failure include, but are not limited to, chemotherapy, radiotherapy, PCOS, autoimmune disease, thyroid disease, diabetes, and surgically induced menopause (e.g., hysterectomy, or oophorectomy).

In one embodiment, a female subject in need of ovarian protection is selected prior to administration of recombinant MIS protein. A clinician can readily identify a subject in need of ovarian protection, for example, a female who will undergo a therapy that increases her risk of premature ovarian failure (e.g., chemotherapy), or a female who exhibits risk factors for premature ovarian failure.

MIS for Uterine Protection

In one embodiment, a recombinant MIS protein as disclosed herein, e.g., a LR-MIS protein, or a recombinant MIS protein produced from processing of the LR-MIS protein, is administered to a female subject as a method of uterine protection. As used herein, "uterine protection" refers to the protection against deleterious or adverse effects on the uterus as a result of a therapeutic agent or treatment, e.g. a chemotherapeutic agent or cytotoxic agent. "Uterine protection" refers to protecting the function of the uterus (e.g., embryo implantation, development of placenta, and capacity to carry a pregnancy to term (e.g., without miscarriage or premature birth)), and the histology of the uterus (e.g., uterine lining health). "Uterine protection" can also refer to the protection against any insult to the ovaries (e.g., surgery, e.g., caesarian section, or an injury). As used herein, "premature birth" is defined as a live birth before 37 weeks of gestation. Uterine protection maintains at least 99%, at least 95%, at least 90%, at least 80%, at least 70%, at least 60%, at least 50%, at least 40%, at least 30%, at least 20%, at least 10% of the uterine function following administration of a therapeutic agent of treatment, as compared to the uterus function prior to said administration.

Uterine protection can maintain physiological or endogenous levels of MIS in the uterus during the removal of an ovary, part of an ovary, or both ovaries. Loss of an ovary, part of an ovary, or both ovaries can lead to a reduction of MIS in the uterus, which can result in damage to the uterus and loss of uterine function. Administration of recombinant MIS can increase the levels in the uterus to maintain uterine health and function.

Uterine protection can be an increase in the uterine lining. A thin uterine lining can lead to a hinder the capacity for an embryo to implant into the uterine lining. Non-invasive imaging, e.g., pelvic ultrasound or sonogram, can be used to assess the thickness of the uterine lining in a subject. During menstruation, the lining of the uterus is 2-4 mm; less than 2 mm indicates a thin uterine lining. Uterine protection can increase the uterine lining in the female subject at least 10%, at least 20%, at least 30%, at least 40%, at least 50%, at least 60%, at least 70%, at least 80%, at least 90%, at least 99%, or more as compared to in the absence of the recombinant MIS protein.

Uterine protection can inhibit or reduce the likelihood of endometriosis in a female subject. Endometriosis is condition that results in the uterine lining growing outside of the uterus, e.g., on the reproductive organs (e.g., ovaries, fallopian tubes, or the tissue surrounding the uterus). Endometriosis hinder the function of the ovaries, fallopian tubes, or the uterus, and can result in infertility. A clinician can assess a subject's risk of having endometriosis, e.g., by family history of the condition, or diagnose a subject with having endometriosis, e.g., by ultrasound or laparoscopic imaging of the reproductive organs.

Uterine protection can be a reduction in uterine dystocia. As used herein, "uterine dystocia" refers to the uncoordinated uterine function, e.g., coordinated uterine contractions during labor, that can result in difficult delivery.

Uterine protection can reduce the incidence, or risk of, pregnancy-induced hypertension or preeclampsia. Hypertension, or high blood pressure in a pregnant woman can lead to pregnancy complication, such as preeclampsia. Preeclampsia can be diagnosed by a skilled clinician, e.g., by a finding of high blood pressure after 20 weeks of gestation and the presence of protein in a urine sample from the patient. Current treatments for pregnancy-induced hypertension or preeclampsia include life style changes (e.g., exercise), bed rest, and therapeutics that reduce blood pressure. A woman who has experienced pregnancy-induced hypertension or preeclampsia in a previous pregnancy is at a higher risk for these conditions in subsequent pregnancies.

Uterine protection can reduce fetal growth restriction during pregnancy. Fetal growth restriction can be caused, e.g., by uterine dysfunction or abnormalities, high blood pressure of the mother, infection in the mother, or environmental factors, and can be diagnosed by a skilled clinician, e.g., by ultrasound.

In one embodiment, a female subject in need of uterine protection is selected prior to administration of recombinant MIS protein. A clinician can readily identify a subject in

MIS for Treatment of PCOS

In one embodiment, a recombinant MIS protein is administered to a female subject as a method of treatment for PCOS. Polycystic ovarian syndrome (PCOS) is associated with elevated levels of androgen secreted from the ovaries, resulting in symptoms including, but not limited to, infertility or difficulty conceiving, no menstruation or irregular menstruation, excess body/facial hair, acne, pelvic pain, and patches of thick, dark skin. PCOS can be diagnosed, e.g., based on anovulation (absence of ovulation), high androgen levels in the blood, and the presence of ovarian cysts. Administration of MIS to a subject who is at risk or having, or who has been diagnosed with having PCOS due to its anti-androgen effects. Genetic and environmental factors increase the likelihood of a subject acquiring PCOS. Risk factors include obesity, having at one of the following conditions: type 2 diabetes, obstructive sleep apnea, heart disease, mood disorders, or endometrial cancer, or if a family member has PCOS. Current treatment of PCOS includes lifestyle changes (e.g., weight loss), hormonal contraceptive therapy to regulate menstrual cycle, metformin, and anti-androgens. Agents that promote ovulation, e.g., clomifene, are used to increase fertility in a subject having been diagnosed with PCOS. In one embodiment, recombinant MIS protein is administered in combination with a second treatment for PCOS, e.g., an anti-androgen. In one embodiment, recombinant MIS is administered prophylactically to a subject at risk of having PCOS.

In one embodiment, a recombinant MIS protein is administered to a subject having been diagnosed with, or at risk of having, PCOS to preserve the fertility of the subject during treatment for PCOS. In another embodiment, a recombinant MIS protein is administered to a subject having been diagnosed with, or at risk of having, PCOS for ovarian and/or uterine. In yet another embodiment, treating PCOS can reduce folliculogenesis in the female subject, or reduce the number of primordial follicles being recruited by at least 10%, at least 20%, at least 30%, at least 40%, at least 50%, at least 60%, at least 70%, at least 80%, at least 90%, at least 99%, or more as compared to in the absence of the recombinant MIS protein. PCOS treatment via administration of recombinant MIS protein can slow the rate of primordial follicle activation by at least 10%, at least 20%, at least 30%, at least 40%, at least 50%, at least 60%, at least 70%, at least 80%, at least 90%, at least 99%, or more as compared to in the absence of the recombinant MIS protein. "Completed arrest" of folliculogenesis refers to a reduction of 100% of primordial follicles being recruited compared to in the absence of the recombinant MIS protein.

In one embodiment, a female subject is need of treatment of PCOS is selected prior to administration of recombinant MIS protein. In one embodiment, a female subject that has previously been diagnosed with PCOS is selected prior to administration of recombinant MIS protein. In one embodiment, a female subject is diagnosed with PCOS prior to administration of recombinant MIS protein. A clinician can diagnose PCOS, or can assess the subject's risk of having PCOS, using standard methods, e.g., measuring androgen levels in the blood of a subject.

In one embodiment, a recombinant MIS protein is administered to a subject how has been diagnosed with, or is at risk of having, PCOS and has been identified as having reduced (e.g., sub-physiological levels of MIS. Administration recombinant MIS can be used as a replacement therapy for individuals with sub-physiological levels of MIS. A clinician can assess the level of MIS in a subject, e.g., by measuring MIS levels in a blood sample from said subject.

In one embodiment, a recombinant MIS protein is administered to a subject who will undergo, or has undergone an ovarian tissue graft or cortical ovarian tissue graft. In one embodiment, recombinant MIS protein is administered to a subject who will undergo, or has undergone an ovarian tissue graft or cortical ovarian tissue graft to prevent ovarian damage (e.g., damage to the primordial follicles, or ovary function) during said ovarian tissue graft or cortical ovarian tissue graft. An ovarian tissue engraftment (e.g., ovarian cortical transplant) comprises the removal of a piece of an ovary, or the ovarian cortex from a subject or a donor, and the engraftment of the piece of the ovary near the fallopian tube. The engraftment can be orthotopic (e.g., in the natural place) or heterotopic (e.g., on the abdominal wall). The engrafted piece of the ovary will produce new egg, secrete reproductive hormones, and allow for conception. Optionally, the piece of the ovary removed can be cryopreserved or preserved heterotopically (e.g., engrafted in arm of a subject). In one embodiment, the whole ovary, or a piece of the ovary removed is maintained or stored in a medium comprising recombinant MIS protein. In another embodiment, the piece of the ovary removed is cryopreserved in a medium comprising recombinant MIS protein. The cryopreserved ovaries are will be thawed prior to engraftment. In one embodiment, cryopreserved ovaries are thawed in a medium comprising recombinant MIS protein.

In one embodiment, recombinant MIS protein is administered to prevent a female from becoming pregnant. Recombinant MIS protein can serve as a contraceptive agent, meaning it halts the ability or decreases the likelihood of conception. Recombinant MIS protein provides short-term or temporary contraception during its administration; a female can become pregnant after administration of recombinant MIS protein has stopped. Administration of recombinant MIS protein to a female subject allows said female to control menstrual cycling, and reproductive hormone secretion, and slows down, or prevents primordial follicle recruitment and/or activation (e.g., administration of recombinant MIS protein stops menstrual cycling).

In one embodiment, recombinant MIS protein is administered to prevent a decline in the functional ovarian reserve (FOR), or reduces folliculogenesis in a female subject. The subject can between the ages of 15 and 55 years of age and will, or is being treated with, a treatment selected from chemotherapy, radiotherapy or chemo-radiotherapy. The subject can have cancer or an autoimmune disease. The subject will, or is undergoing treatment with a cytotoxic drug. Reducing folliculogenesis in the female subject can be a reduction in the number of primordial follicles being recruited by at least 10% as compared to in the absence of the recombinant MIS protein, or a reduction in the number of primordial follicles being recruited by between 10% and 99%, or a complete arrest in folliculogenesis as compared to in the absence of the recombinant MIS protein.

Subjects in Need of Treatment

In one embodiment, the female subject has cancer and will be treated with, or is currently being treated with, or has been treated with a chemotherapy or anti-cancer agent. "Cancer" is a hyperproliferation of cells that have lost normal cellular control, resulting in unregulated growth, lack of differentiation, local tissue invasion, and metastasis. Cancers are classified based on the histological type (e.g., the tissue in which they originate) and their primary site (e.g., the location of the body the cancer first develops).

There are 6 major histological types of cancer: carcinoma, sarcoma, myeloma, leukemia, lymphoma, and mixed types (cancer that comprises various components within one histological type, or from two or more histological types). As used herein, an "anti-cancer agent" can refer to any therapeutic that has an intended use for the treatment of cancer (e.g., an immune checkpoint inhibitor, CART cells, or targeted therapies) that has been shown to have adverse effects on the uterus and/or ovaries. Damage to the ovaries and/or uterus can be measured by, e.g., the presence of cell death, tissue defects or decay, or abnormal function of the ovary or uterus (e.g., abnormal hormone secretion, increased folliculogenesis, or desensitization of follicle to hormone stimulation).

In some embodiments, the technology described herein relates to a recombinant MIS protein as described herein, e,g., a LR-MIS protein as described herein (e.g., amino acids 25-559 of SEQ ID NO: 4), or a recombinant MIS protein produced from processing of the LR-MIS protein (i.e., where the produced protein is a recombinant MIS variant homodimer protein of comprising two monomers, each monomer comprising (i) a N-terminal domain of the recombinant MIS protein comprising amino acids 26-451 of SEQ ID NO: 3 (MIS) or a variant having at least 85% sequence identity thereto, wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS) or a variant having at least 85% sequence identity thereto), for use in a method for any of: ovarian protection, oncoprotection, uterine protection, treatment and/or prevention of PCOS.

By way of example, the method of ovarian protection encompasses methods for protecting the female reproductive system against natural or artificial insults by administering a composition a recombinant MIS protein as described herein, e,g., a LR-MIS protein as described herein (e.g., amino acids 25-559 of SEQ ID NO: 4), or a recombinant MIS protein produced from processing of the LR-MIS protein as described herein. In some embodiments, this invention relates to a method of protecting ovaries from cancer therapy regimens, chemotherapy and radiotherapy (i.e., in a method of oncoprotection), by administering to a female a composition comprising a recombinant MIS protein as described herein, e,g., a LR-MIS protein as described herein (e.g., amino acids 25-559 of SEQ ID NO: 4), or a recombinant MIS protein produced from processing of the LR-MIS protein as described herein. Methods to enhance ovarian functions, ameliorate symptoms of menopause, and improve the success of in vitro fertilization are also disclosed.

As disclosed herein, an artificial insult comprises chemical insult, radiation insult, surgical insult, or a combination thereof. Natural insults to the reproductive system occur as a consequence of aging, genetic background, physiological factors, environmental factors, or other developmental and genetic factors. The artificial and natural insults treated by the methods of the present invention encompass insults that occur in vivo, as opposed to, e.g., insults that occur to isolated tissues or cells.

According to an embodiment of the invention, the artificial insult comprises chemical insults, including for example, cytotoxic factors, chemotherapeutic drugs, hormone deprivation, growth factor deprivation, cytokine deprivation, cell receptor antibodies, and the like. Chemotherapeutic drugs include SFU, vinblastine, actinomycin D, etoposide, cisplatin, methotrexate, doxorubicin, among others.

In accordance with another embodiment of the invention, the artificial insult comprises radiation insult, including ionization radiation, x-ray, infrared radiation, ultrasound radiation, heat, or a combination thereof. Radiation is administered to a patient through an invasive radiation therapy, a non-invasive radiation therapy, or both.

Ovarian protection, including oncoprotection, uterine protection and PCOS according to the methods and compositions as disclosed herein is applicable to females in all age groups consisting of pre-reproductive age, reproductive age and post-reproductive age group.

Yet still another embodiment of the invention, a composition comprising a recombinant MIS protein as described herein, e,g., a LR-MIS protein as described herein (e.g., amino acids 25-559 of SEQ ID NO: 4), or a recombinant MIS protein produced from processing of the LR-MIS protein as described herein can be used in a method of protecting a female's ovaries and/or reproductive system from damage caused by a treatment for a disease, disorder, or condition comprising administering to a mammalian female a treatment effective to treat a disease, disorder, or condition, wherein said treatment is selected from the group consisting of chemical treatment, radiological treatment, surgical treatment, and combinations thereof; and a composition comprising a composition a recombinant MIS protein as described herein, e,g., a LR-MIS protein as described herein (e.g., amino acids 25-559 of SEQ ID NO: 4), or a recombinant MIS protein produced from processing of the LR-MIS protein as described herein, in an amount sufficient to protect said ovaries or uterus or uterine lining, and/or reproductive system from damage and/or destruction caused by said treatment. In some embodiments, the methods described herein enable the female subject to retain the ability and/or ovary reserves to produce viable offspring. In some embodiments, the administration of the composition is terminated prior to exposure of the female subject to the cytotoxic agent or chemotherapy agent, or alternatively concomitant with the treatment and/or subsequent to the treatment with the cytotoxic agent or chemotherapy agent, or cancer treatment as disclosed herein.

Recombinant MIS Variant for Ovarian Protection or Uterine Protection

As disclosed herein, the technology described herein relates to administration of a composition comprising a recombinant MIS protein as described herein, e,g., for use in a method for ovarian protection or uterine protection against a natural or artificial insult, where the recombinant MIS protein is a LR-MIS protein as described herein (e.g., amino acids 25-559 of SEQ ID NO: 4), or a recombinant MIS protein produced from processing of the LR-MIS protein, where the produced protein is a recombinant MIS variant homodimer protein of comprising two monomers, each monomer comprising (i) a N-terminal domain of the recombinant MIS protein comprising amino acids 26-451 of SEQ ID NO: 3 (MIS) or a variant having at least 85% sequence identity thereto, wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS) or a variant having at least 85% sequence identity thereto.

In some embodiments, artificial insults are the consequence of a therapy against a disease or a disorder. The disease or disorder comprises, for example, cancer, rheumatoid arthritis, angioplasy, or restenosis.

In some embodiments, artificial insults also include, without limitation, chemical, radiation, and surgical insults. Examples of chemical insults include, cytotoxic factors, chemotherapeutic drugs, hormone deprivation, growth factor deprivation, cytokine deprivation, cell receptor antibodies and the like. Further non-limiting examples include TNF-alpha, TNF-beta, IL-1, INF-gamma, IL-2, insulin-like growth factor, transforming growth factor beta1, vascular endothelial growth factor, fibroblast growth factor, SFU, vinblastine, actinomycin D, etoposide, cisplatin, methotrexate, doxorubicin, and the like.

In accordance with another embodiment of the invention, an artificial insult is a radiation insult. It is shown that the germlines of female mammals exposed to radiation are seriously damaged and administration of the composition as disclosed herein in vivo or ex vivo protects oocytes from destruction induced by a therapeutically-relevant dose of ionizing radiation.

Radiation insult, according to the invention disclosed herein, encompasses both non-invasive (external) and invasive (internal) radiation therapies. In an external radiation therapy, treatment is affected by radiation sources outside the body, whereas in an invasive radiation therapy treatment is affected by radiation sources planted inside the body. The representative diseases treated by non-invasive or invasive radiation therapy include, for example, cancer, rheumatoid arthritis, angioplasty, or restenosis.

Invasive radiation therapy encompasses, for example, selective internal radiation therapy (SIRT), incorporation of the radioactive materials into small particles, microspheres, seeds, wires and the like. These objects are directly implanted into the various tissue, organs, or their respective arterial blood supply within the body. Various methods for introducing radiation into an area treated for stenosis are known. Some methods deliver radiation in a solid medium, while others utilize liquid sources. For example, a procedure in reducing the restenosis rate is the introduction of radiation energy into the interior of the vessel. This procedure, known as "intravascular radiation therapy" (IRT) has been shown to inhibit fibroblast and smooth muscle cell hyperplasia. For example, U.S. Pat. No. 5,059,166, discloses an IRT method that relies on a radioactive stent that is permanently implanted in the blood vessel after completion of the lumen opening procedure. U.S. Pat. No. 5,302,168, discloses use of a radioactive source contained in a flexible catheter. U.S. Pat. No. 5,503,613, discloses uses a liquid filled balloon to guide a solid source wire to a treatment site. U.S. Pat. No. 5,616,114, discloses an apparatus and method for delivering liquid radiation into a balloon-tipped catheter. Radiation therapies disclosed by aforementioned patents, are disclosed merely as examples of radiotherapeutic regimens used to treat patients and are non-limiting.

The use of radioactive material in connection with therapies, such as those disclosed above, creates a risk of harmful exposure, both to the medical personnel and to patients. Precautionary measures need to be taken to protect against the harm caused by the leakage of liquid radiation into the blood stream during these therapies. Sensitive organs, such as the ovaries, are inevitably damaged depending on the invasiveness of the procedure used. Accordingly, the present invention encompasses methods to protect the ovaries and uterus of both patients and medical personnel from a risk of harm caused by exposure to radiation during such therapies.

Radiation is emitted from a variety of radionuclides. These radionuclides encompass, for example, beta-ray emitters, gamma-ray emitters, or a radionuclide that emits both beta-ray and gamma-ray. Further examples of radionuclides include, Strontium 90, Iridium 192, Phosphorous 32, Rhenium 186, Rhenium 188, 198Au, 169Er, 166Ho, 153Sm, and 165Dy, which are chosen according to the purpose of treatment. Other radiation sources include sources used in nuclear magnetic resonance diagnosis in which the central ion of the complex salt must be paramagnetic. In particular, the radiation sources use the divalent and trivalent ions of the elements of atomic numbers 21-29, 42, 44 and 58-70. Suitable ions are, for example, the chromium(III), manganese(II), iron(II), nickel(II), copper(II), praseodymium(III), neodymium(III), samarium(III), ytterbium(III), gadolinium (III), terbium(III), dysprosium(III), holmium(III), erbium (III), and iron(III).

According to another embodiment of the invention disclosed herein, radiation insult includes ultrasound radiation. Ultrasound radiation is administered to patients, either alone or in combination with other therapies, for example, hormonal therapy, chemotherapy, or surgery. The therapeutic regimen is applied either preoperatively, i.e., to the tumor in situ or postoperatively, in the region of the tumor after removal of the primary cancerous lesion. The ultrasound therapy comprises both the invasive and non-invasive ultrasound treatments. The dosage of ultrasonic energy applied is, for example, above 22.5 watt/sec, and has a frequency in the range of, for example, about 1 KHz to about 3 MHz.

According to another embodiment of this invention, radiation insult includes, x-ray, infrared, and heat. Heat is often used to selectively induce apoptosis in intended cells or tissues. Preferably heat is used to treat inflammation. The term inflammation includes inflamed atherosclerotic plaques, restenosis, and arteritis such as that found in systemic lupus, myocarditis of the autoimmune etiology, arteriovenous fistulea, dialysis grafts or other vascular prosthesis. The phrase "treating inflammation" also includes treating a region of a vein prior to or after balloon angioplasty, or related interventions that could result in inflammation and subsequent thrombosis, acute closure or restenosis. Heat may be transferred to the target cells by a variety of methods. For example, heat is transferred into an inflamed plaque in a blood vessel by means of a catheter, stent, or liquid heat. Catheter or stents are heated electrically or with microwave or radio frequency radiation or other means. Heat is also generated from internal or external devices, such as radiofrequency sources outside the body. The present invention protects ovaries from the risk of over-exposure to heat waves or liquid heat during heat therapy.

Natural insults, as defined herein, include damages resulting from physiological, biochemical or developmental processes occurring in a female body. A manifest natural insult is apoptosis due to aging. Natural insults are influenced, for example, by genetic background of the female, environmental effects, or both. The functional life span of female gonads is defined by the size and rate of depletion of the endowment of oocytes enclosed within follicles in the ovaries at birth. This continuous loss of oocytes throughout life, referred to by many as the female biological clock, is driven by a genetic program of cell death that is controlled by physiological and biochemical pathways and players and is conserved from worms to humans (Morita & Tilly (1999) id.). In some embodiments, the methods as disclosed herein relate to the administration of a MIS variant protein, e.g., LR-MIS or a protein produced therefrom, in a method to reduce normal or pre-mature germ cell depletion in a female mammal.

Examples of disease and disorders resulting from a natural insult include, disturbances in menstruation, abnormal uterine bleeding, abnormal ovulatory cycles, amenorrhea, pelvic pain, sexual dysfunction, in fertility, menstrual cyclicity, and pre-mature menopause among others.

Other insults include surgical insults wherein a woman's reproductive system, in part or in whole, is surgically removed. In particular, hormonal imbalance, resulting from the removal of one ovary, is fully or partially restored by administration of the therapeutic agent of the invention.

Included within the scope of this invention are methods to protect women's ovaries from natural and artificial insults, not only to keep them fertile, but also to preserve enough ovarian function to prevent or delay menopause and its associated disorders. Women are subject to natural or artificial insult in any age group. These age groups are pre-reproductive, reproductive or post-reproductive age groups. Pre-mature menopausal syndromes are initiated by a wide variety of artificial or natural conditions. Menopausal disorders, include, for example, somatic disorders such as osteoporosis, cardiovascular disease, somatic sexual dysfunction, loss of libido; cognitive disorders, such as loss of memory; emotional disorders, such as depression, and the like.

Recombinant MIS Variant in a Method for Oncoprotection

As disclosed herein, the technology described herein relates to administration of a composition comprising a recombinant MIS protein as described herein, e,g., for use in a method for oncoprotection, e.g., protection of the ovaries prior to, during or after a cancer treatment.

Cancer includes, for example, colon carcinoma, pancreatic cancer, breast cancer, ovarian cancer, fibrosarcoma, myxosarcoma, liposarcoma, chondrosarcoma, osteogenic sarcoma, chrondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, acute lymphocytic leukemia and acute myelocytic leukemia, chronic leukemia and polycythemia vera, lymphoma (Hodgkin's disease and non-Hodgkin's disease), multiple myeloma, Waldenstrom's macroglobulinemia, or immunoglobulin heavy chain diseases.

A carcinoma is a cancer that originates in an epithelial tissue. Carcinomas account for approximately 80-90% of all cancers. Carcinomas can affect organs or glands capable of secretion (e.g., breasts, lung, prostate, colon, or bladder). There are two subtypes of carcinomas: adenocarcinoma, which develops in an organ or gland, and squamous cell carcinoma, which originates in the squamous epithelium. Adenocarcinomas generally occur in mucus membranes, and are observed as a thickened plaque-like white mucosa. They often spread easily through the soft tissue where they occur. Squamous cell carcinomas can originate from any region of the body. Examples of carcinomas include, but are not limited to, prostate cancer, colorectal cancer, microsatellite stable colon cancer, microsatellite instable colon cancer, hepatocellular carcinoma, breast cancer, lung cancer, small cell lung cancer, non-small cell lung cancer, lung adenocarcinoma, melanoma, basal cell carcinoma, squamous cell carcinoma, renal cell carcinoma, ductal carcinoma in situ, invasive ductal carcinoma.

Sarcomas are cancers that originate in supportive and connective tissues, for example bones, tendons, cartilage, muscle, and fat. Sarcoma tumors usually resemble the tissue in which they grow. Non-limiting examples of sarcomas include, Osteosarcoma or osteogenic sarcoma (originating from bone), Chondrosarcoma (originating from cartilage), Leiomyosarcoma (originating from smooth muscle), Rhabdomyosarcoma (originating from skeletal muscle), Mesothelial sarcoma or mesothelioma (originate from membranous lining of body cavities), Fibrosarcoma (originating from fibrous tissue), Angiosarcoma or hemangioendothelioma (originating from blood vessels), Liposarcoma (originating from adipose tissue), Glioma or astrocytoma (originating from neurogenic connective tissue found in the brain), Myxosarcoma (originating from primitive embryonic connective tissue), or Mesenchymous or mixed mesodermal tumor (originating from mixed connective tissue types).

Myelomas are cancers that originate in plasma cells of bone marrow. Non-limiting examples of myelomas include multiple myeloma, plasmacytoma and amyloidosis.

Leukemias (also known as "blood cancers") are cancers of the bone marrow, which is the site of blood cell production. Leukemia is often associated with the overproduction of immature white blood cells. Immature white blood cells do not function properly, rendering the patient prone to infection. Leukemia additionally affects red blood cells, and can cause poor blood clotting and fatigue due to anemia. Leukemia can be classified as being acute myeloid leukemia (AML), Chronic myeloid leukemia (CML), Acute lymphocytic leukemia (ALL), and Chronic lymphocytic leukemia (CLL). Examples of leukemia include, but are not limited to, Myelogenous or granulocytic leukemia (malignancy of the myeloid and granulocytic white blood cell series), Lymphatic, lymphocytic, or lymphoblastic leukemia (malignancy of the lymphoid and lymphocytic blood cell series), and Polycythemia vera or erythremia (malignancy of various blood cell products, but with red cells predominating).

Lymphomas develop in the glands or nodes of the lymphatic system (e.g., the spleen, tonsils, and thymus), which purifies bodily fluids and produces white blood cells, or lymphocytes. Unlike leukemia, lymphomas form solid tumors. Lymphoma can also occur in specific organs, for example the stomach, breast, or brain; this is referred to as extranodal lymphomas). Lymphomas are subclassified into two categories: Hodgkin lymphoma and Non-Hodgkin lymphoma. The presence of Reed-Sternberg cells in Hodgkin lymphoma diagnostically distinguishes Hodgkin lymphoma from Non-Hodgkin lymphoma. Non-limiting examples of lymphoma include Diffuse large B-cell lymphoma (DLBCL), Follicular lymphoma, Chronic lymphocytic leukemia (CLL), Small lymphocytic lymphoma (SLL), Mantle cell lymphoma (MCL), Marginal zone lymphomas, Burkitt lymphoma, hairy cell leukemia (HCL).

In one embodiment, the cancer is a solid tumor. Non-limiting examples of solid tumors include Adrenocortical Tumor, Alveolar Soft Part Sarcoma, Chondrosarcoma, Colorectal Carcinoma, Desmoid Tumors, Desmoplastic Small Round Cell Tumor, Endocrine Tumors, Endodermal Sinus Tumor, Epithelioid Hemangioendothelioma, Ewing Sarcoma, Germ Cell Tumors (Solid Tumor), Giant Cell Tumor of Bone and Soft Tissue, Hepatoblastoma, Hepatocellular Carcinoma, Melanoma, Nephroma, Neuroblastoma, Non-Rhabdomyosarcoma Soft Tissue Sarcoma (NRSTS), Osteosarcoma, Paraspinal Sarcoma, Renal Cell Carcinoma, Retinoblastoma, Rhabdomyosarcoma, Synovial Sarcoma, and Wilms Tumor. Solid tumors can be found in bones, muscles, or organs, and can be sarcomas or carcinomas.

In one in embodiment, the cancer is metastatic.

In one embodiment, the female subject has autoimmune disease and will be treated with, or is currently being treated with, or has been treated with an immunotherapy. As used herein, an "autoimmune disease or disorder" is characterized by the inability of one's immune system to distinguish between a foreign cell and a healthy cell. This results in one's immune system targeting one's healthy cells for programmed cell death. Non-limiting examples of an autoimmune disease or disorder include oophoritis, inflammatory arthritis, type 1 diabetes mellitus, multiples sclerosis, psoriasis, inflammatory bowel diseases, SLE, and vasculitis, allergic inflammation, such as allergic asthma, atopic dermatitis, and contact hypersensitivity, rheumatoid arthritis, multiple sclerosis (MS), systemic lupus erythematosus, Graves' disease (overactive thyroid), Hashimoto's thyroiditis (underactive thyroid), chronic graft v. host disease, hemophilia with antibodies to coagulation factors, celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/giant cell arteritis, chronic fatigue syndrome CFS), psoriasis, autoimmune Addison's Disease, ankylosing spondylitis, Acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis and fibromyalgia (FM).

In one embodiment, the female subject will be treated with, or is currently being treated with, or has been treated with, a cytotoxic drug or cytotoxic agent that causes cell death or cell damage to cells in the uterus or ovary. A cytotoxic drug or agent has the capacity to directly damage DNA (e.g., alkylating agent), inhibit synthesis and/or replication of DNA (e.g., an antimetabolite or topoisomerase inhibitor), and/or arrest the cell cycle (a mitosis inhibitor). Cytotoxic drugs or agents can be specific for a cell type (e.g., a cancer cell) or can target a broad range of cell (e.g., all actively dividing cells). Exemplary alkylating agents include cisplatin (Platinol), daunorubicin (Cerubidine), doxorubicin (Adriamycin, Doxil), etoposide (Toposar, Etopophos). Exemplary antimetabolite include methotrexate (Trexall, Otrexup), fluorouracil (Adrucil, Efudex), hydroxyurea (Hydrea, Droxia), and mercaptopurine (Purinethol). Exemplary mitosis inhibitors include vinblastine, vincristine (Vincasar PFS, Marqibo) and pacitaxel (Abraxane, Onxol). Exemplary topoisomerase inhibitors include etoposide (Etopophos), teniposide (Vumon), and mitoxantrone.

In one embodiment, the female subject will be treated with, or is currently being treated with, or has been treated with a long-term therapeutic regime, i.e., treatment for a chronic condition, relapse in chronic condition, human immunodeficiency virus (HIV), viral hepatitis, viral or bacterial meningitis, malaria, or a neurodegenerative disease. In one embodiment, the female subject will be treated with, or is currently being treated with, or has been treated with a long-term therapeutic regime that does not result in damage to the uterus and/or ovaries. For example, a subject who is undergoing treatment for human immunodeficiency virus (HIV) may wish to delay or slow the recruitment and/or activation of primordial follicle recruitment, or preserve their fertility. The subject may wish to preserve her fertility and/or prevent pregnancy during a long-term treatment for reasons including, but not limiting to, because the therapeutic being administered has adverse effects on a fetus, or a pregnancy would not be ideal during the treatment due to side effects of the treatment (e.g., fatigue, or nausea).

A female subject may wish to delay or slow the recruitment of primordial follicle recruitment, or preserve their fertility, for reasons other than ovarian or uterine protection during treatment. For example, a female subject may wish to delay having children due to external factors, such as schooling, a career, financial constraints, age of current children, or relationship status. In one embodiment, a female subject is in need of preserving fertility. In one embodiment, a female subject is administered a recombinant MIS protein described herein to preserve fertility, and is not undergoing additional treatment or receiving additional therapeutics. As used herein, "fertility preservation" refers to maintaining the fertility potential (the likelihood of conceiving a child based as factors e.g., age of eggs, regularity of menstrual cycle, ovarian reserve, ovarian function, ovarian hormone secretion) a subject in its existing state, e.g., at the time in which a recombinant MIS protein is first administered to a patient. "Fertility preservation" can refer to extended fertility beyond its natural limit, e.g., past child-bearing age. "Fertility preservation" can refer to maintaining the same number of primordial follicles present in the ovary of a subject prior to administration of recombinant MIS protein. Recombinant MIS protein can be administered to a female subject to inhibit age-related fertility decline. "Age-related fertility decline" refers to a decrease in likelihood of conceiving due to the age of the female. The peak biological age for a female to have a child is in the late teens and early twenties; the rate of infertility increases with the age of the female, and subsequently her eggs, and children born to older females have a higher incidence of genetic disorders and birth defects. In one embodiment, recombinant MIS protein is administered to a pre-pubescent female subject at risk of having, or has premature ovarian failure.

Alternatively, a female subject may wish to delay or slow the recruitment of primordial follicle recruitment, or preserve their fertility, if the subject has, or is pre-disposed diminished ovarian reserve (DOR), premature ovarian aging (POA), primary ovarian insufficiency (POI), endometriosis, polycystic ovarian syndrome (PCOS), one or more FMR1 premutations or 55-200 GCC FMR1 repeats, BRAC1 mutations, Turner syndrome, an autoimmune disease, an ovarian autoimmune disease (e.g., oophoritis) thyroid autoimmunity, adrenal autoimmunity or autoimmunity polyglandular syndromes. A skilled clinician can determine if a subject has, or is pre-disposed to having any of these conditions, e.g., using standard tests known in the art.

Kits

In one aspect, described herein is a kit for use in ovarian protection or oncoprotection of a female subject comprising a pump or infusion device comprising a recombinant MIS protein, wherein the recombinant MIS protein comprises amino acid residues 25-559 of SEQ ID NO: 4 (LR-MIS) or a polypeptide which has at least 85% sequence identity to the amino acid sequence of amino acid residues 25-559 of SEQ ID NO: 4 (LR-MIS); or a recombinant MIS protein, wherein the recombinant MIS protein is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS), wherein optionally, amino acid residue 452 of SEQ ID NO: 1 is changed from S to R, and instructions for implanting the pump or infusion device into the female subject for the treatment of a subject with one or more of: a diminished ovarian reserve (DOR), premature ovarian aging (POA), primary ovarian insufficiency (POI), endometriosis, polycystic ovarian syndrome (PCOS), one or more FMR1 premutations or 55-200 GCC FMR1 repeats, or where the subject is undergoing, has, or will undergo a cancer treatment. A kit is any manufacture (e.g., a package or container) comprising at least one reagent, e.g., recombinant MIS protein, the manufacture being promoted, distributed, or sold as a unit for performing the methods described herein.

In another aspect, described herein is a kit for use in uterine protection of a female subject comprising a pump or infusion device comprising a recombinant MIS protein, wherein the recombinant MIS protein comprises amino acid residues 25-559 of SEQ ID NO: 4 (LR-MIS) or a polypeptide which has at least 85% sequence identity to the amino acid sequence of amino acid residues 25-559 of SEQ ID NO: 4 (LR-MIS); or a recombinant MIS protein, wherein the recombinant MIS protein is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS), wherein optionally, amino acid residue 452 of SEQ ID NO: 1 is changed from S to R, and instructions for implanting the pump or infusion device into the female subject for the treatment of a subject with one or more of: a diminished ovarian reserve (DOR), premature ovarian aging (POA), primary ovarian insufficiency (POI), endometriosis, polycystic ovarian syndrome (PCOS), one or more FMR1 premutations or 55-200 GCC FMR1 repeats, or where the subject is undergoing, has, or will undergo a cancer treatment. A kit is any manufacture (e.g., a package or container) comprising at least one reagent, e.g., recombinant MIS protein, the manufacture being promoted, distributed, or sold as a unit for performing the methods described herein.

In another aspect, described herein is a kit for use in treatment of polycystic ovarian syndrome (PCOS) of a female subject comprising a pump or infusion device comprising a recombinant MIS protein, wherein the recombinant MIS protein comprises amino acid residues 25-559 of SEQ ID NO: 4 (LR-MIS) or a polypeptide which has at least 85% sequence identity to the amino acid sequence of amino acid residues 25-559 of SEQ ID NO: 4 (LR-MIS); or a recombinant MIS protein, wherein the recombinant MIS protein is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS), wherein optionally, amino acid residue 452 of SEQ ID NO: 1 is changed from S to R, and instructions for implanting the pump or infusion device into the female subject for the treatment of a subject with one or more of: polycystic ovarian syndrome (PCOS), one or more FMR1 premutations or 55-200 GCC FMR1 repeats, and/or where the subject is undergoing, has, or will undergo a cancer treatment. A kit is any manufacture (e.g., a package or container) comprising at least one reagent, e.g., recombinant MIS protein, the manufacture being promoted, distributed, or sold as a unit for performing the methods described herein.

The kits described herein can optionally comprise additional components useful for performing the methods described herein. By way of example, the kit can comprise fluids (e.g., buffers) suitable for composition comprising an recombinant MIS protein as described herein, an instructional material which describes performance of a method as described herein, and the like. A kit can further comprise devices and/or reagents for delivery of the composition as described herein. Additionally, the kit may comprise an instruction leaflet and/or may provide information as to the relevance of the obtained results.

Administration

An effective amount or dosage of the composition comprising a MIS protein or MIS variant protein (e.g., LR-MIS protein), or nucleic acid encoding the same is administered to, for example, arrest folliculogenesis. For example, an effective amount is the amount of MIS protein or MIS variant protein (e.g., LR-MIS protein), or nucleic acid encoding the same to reduce the number of primordial follicles being recruited by at least 10%, at least 20%, at least 30%, at least 40%, at least 50%, at least 60%, at least 70%, at least 80%, at least 90%, or at least 99% compared to when the composition is not administered. An amount of the composition comprising a MIS protein or MIS variant protein (e.g., LR-MIS protein), or nucleic acid encoding the same administered to a female subject is considered effective when the amount is sufficient to reduce the number of primordial follicles being recruited to a desirable number, or decrease the probability of a primordial being recruited to a desirable value. In some embodiments, the amount of composition administered is sufficient to achieve contraception.

In some embodiments, a composition comprising a MIS protein or MIS variant protein (e.g., LR-MIS protein), or nucleic acid encoding the same is can be administered at one time or divided into subdoses, e.g., 2-4 subdoses and administered over a period of time, e.g., at appropriate intervals through the day or other appropriate schedule. In some embodiments, a composition comprising a MIS protein or MIS variant (e.g., LR-MIS) as described herein, or a vector expressing such a MIS variant protein is administered at superphysiological levels, such that the levels in the blood are superphysiological relative to normal levels, but is sufficient to achieve physiological MIS levels in the ovary. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. The dosage should not be so large as to cause adverse side effects.

In some embodiments, the composition as described herein is administered on a continuous or semi-continuous, or temporary basis, depending on the type of insult and objectives intended (e.g., for ovarian and/or uterine protection in general, for oncoprotection or for the treatment of PCOS). For example, if protection of the ovaries and uterus from long term natural insults is intended, administration of the composition of this invention on a continuous or semi-continuous basis is preferred. In a continuous administration, the composition is generally administered regularly, on a predetermined interval, for an indefinite period of time.

Predetermined intervals comprise daily, weekly, biweekly, or monthly, or yearly intervals.

If protection from artificial insults is intended, both short term and long term administration are encompassed herein, depending on the type of insult and the objective of the therapy intended. An example of a short term administration is the administration to protect ovaries from radiation or chemical insults, or cancer treatment as described herein. In short term administration, the composition is administered, at least once, in a period of from about thirty days prior to immediately prior to exposure to the insult. More preferably the composition is administered from about fifteen days to about two days, and most preferably from about seven days to about two hours prior to exposure to the insult. In some embodiments, the administration of the composition is terminated prior to ovarian exposure to the insult, or it is continued during exposure or after the exposure is terminated.

The dosage of the amount of MIS protein as disclosed herein is adjusted according to, for example, the duration and the objective of the treatment intended. A lower dosage of the MIS protein may be required in a more prolonged and continuous administration.

In some embodiments, the administration is achieved in vitro, in vivo or ex vivo. In some embodiments, the in vivo administration encompasses orally, intravascularly, intraperitoneally, intra-uterine, intra-ovarian, subcutaneously, intramuscularly, rectally, topically, or a combination thereof. In embodiments were intra-ovarian administration is desired, intra-ovarian administration can be achieved by several methods, including, for example, by direct injection into the ovary. The injection is made to the ovary in vivo or ex vivo, for example, where ex-vivo administration is desired where the ovary is removed (e.g., ovarian tissue graft or cortical ovarian tissue graft) and the like. In some embodiments, the ovarian tissue graft or cortical ovarian tissue graft is stored in a media comprising the recombinant MIS protein as disclosed herein (e.g., a LR-MIS protein as described herein (e.g., amino acids 25-559 of SEQ ID NO: 4), or a recombinant MIS protein produced from processing of the LR-MIS protein), either prior to, during, or after cryopreservation of the ovarian tissue graft or cortical ovarian tissue graft.

In particular embodiments, the MIS is a recombinant protein or a functional fragment or derivative or variant thereof. In some embodiments, the MIS is a recombinant human MIS protein or a functional fragment or derivative or variant thereof (e.g., SEQ ID NO: 4, or SEQ ID NO: 5). In some embodiments, the recombinant MIS protein is a LR-MIS protein as described herein (e.g., amino acids 25-559 of SEQ ID NO: 4), or a recombinant MIS protein produced from processing of the LR-MIS protein, where the produced protein is a recombinant MIS variant homodimer protein of comprising two monomers, each monomer comprising (i) a N-terminal domain of the recombinant MIS protein comprising amino acids 26-451 of SEQ ID NO: 3 (MIS) or a variant having at least 85% sequence identity thereto, wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS) or a variant having at least 85% sequence identity thereto. In some embodiments, the MIS is a natural (i.e., wild type) human MIS that corresponds to SEQ ID NO: 3.

A recombinant human MIS protein, MIS variant protein or derivative or functional fragment thereof can be administered by any route known in the art or described herein, for example, oral, parenteral (e.g., intravenously or intramuscularly), intraperitoneal, rectal, cutaneous, nasal, vaginal, inhalant, skin (patch), or ocular. The recombinant human MIS protein or derivative or functional fragment protein may be administered in any dose or dosing regimen.

With respect to the therapeutic methods of the invention, it is not intended that the administration of a recombinant human MIS protein or polynucleotide encoding such a recombinant human MIS protein or functional fragment thereof be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to treat an autoimmune disease or immune-related disorder as disclosed herein. An effective amount, e.g., a therapeutically effective dose of a recombinant human MIS protein may be administered to the patient in a single dose or in multiple doses. When multiple doses are administered, the doses may be separated from one another by, for example, one hour, three hours, six hours, eight hours, one day, two days, one week, two weeks, or one month. For example, a composition comprising a recombinant human MIS protein agent can be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

Administration of the compositions comprising a recombinant human MIS protein or MIS protein variant, or nucleic acid encoding the same as disclosed herein may be by parenteral or nonparenteral means, but is preferably oral or intravenous. Treatment may be for short periods of time, e.g., pulsed or continuous throughout the lifetime of the patient. In all aspects of the embodiments as disclosed herein, the agents and compositions as disclosed herein are administered by pulse administration. In some embodiments, they are administered orally to the subject. In some embodiments, the subject is a mammal, e.g., a human. In some embodiments, the subject is undergoing, or will undergo chemotherapeutic treatment or cancer treatment. In some embodiments, the subject is undergoing, or will undergo immunotherapy.

In some embodiments, the amount of a MIS protein or MIS protein variant is administered to a subject (in pulses, as continuous treatment or as a one-time administration (e.g., via gene therapy expression of the MIS protein or MIS protein variants)) such that the blood levels of the MIS protein or MIS protein variant in the treated subject are above about 20%, or above about 30%, or above about 40%, or above about 50%, or between about 50-100% or above about 2-fold, or above about 3-fold, or above about 4-fold, or above about 5-fold or more than 5-fold the blood levels of the endogenous MIS protein in an age-matched female subject are generally considered to be sufficient to arrest follicularogeneis in the subject, and thus therefore are sufficient amounts of the MIS protein or MIS variant protein for use in methods for contraception, or to preserve ovarian reserve (e.g., to prevent a decline in functional ovarian reserve (FOR)), or to preserve fertility as disclosed herein.

The recombinant MIS protein can be administered at a high level sufficient to arrest follicularogenesis or keep the ovary in a quiescent state. The high levels of recombinant MIS protein can be sufficient to elicit in any of the following: (a) a concentration of MIS protein in the blood of the subject that is 10% to 50% higher as compared to the absence of administration of the recombinant MIS protein; (b) a concentration of MIS protein in the blood of the subject that is 50% to 100% higher as compared to the absence of administration of the recombinant MIS protein; (c) a concentration of MIS protein in the blood of the subject that is 2 to 5-fold higher or more than 5-fold higher as compared to the absence of administration of the recombinant MIS protein; or (d) a concentration of MIS protein in the blood of the subject of between 1 µg/ml-5 µg/ml. The high levels of recombinant MIS protein is administered between 0.001 mg/kg per hour and 0.1 mg/kg per hour, or between 0.2 µg/hr and 10.0 µg/hr.

In one embodiment, the levels of MIS in the ovary and/or uterus are maintained at physiological or endogenous levels. Super-physiological levels of MIS in the blood can be required to maintain physiological of MIS in the ovary and/or uterus. In one embodiment, the levels of MIS in the blood, the ovary, and/or the uterus are at physiological or endogenous levels. In another embodiment, the levels of MIS in the blood, the ovary, and/or the uterus are at super-physiological levels. In another embodiment, the levels of MIS in the blood, the ovary, and/or the uterus are at sub-physiological levels.

In some embodiments, administration of a MIS protein or MIS variant protein, or nucleic acid encoding the same, as disclosed herein can be a one-time administration, e.g., via a vector e.g., viral vector or gene therapy where it is desirable for permanent arrest of follicular genesis, e.g., for permanent contraception of animal such as dogs and cats.

In an alternative embodiment, administration of a MIS protein or MIS variant protein as disclosed herein is by pulsed administration, e.g., for temporary arrest of follicularogeneis, e.g., to temporary arrest follicularogeneis or temporary contraception of subjects, e.g., human subjects where the subject has a desire to preserve fertility during administration of a cytotoxic drug or therapeutic.

In some embodiments, pulsed administration of a composition comprising a MIS protein or MIS protein variant as disclosed herein is more effective than continuous treatment because total pulsed doses are often lower than would be expected from continuous administration of the same composition. Each pulse dose can be reduced and the total amount of drug administered over the course of treatment is minimized. Each pulse dose can be reduced and the total amount of drug administered over the course of treatment to the patient can be minimized. With pulse therapy, in vivo levels of a MIS protein or MIS protein variant as disclosed herein can drop below that level required for effective continuous treatment. Pulsed administration can reduce the amount of a composition comprising a MIS protein or MIS protein variant as disclosed herein administered to the patient per dose, and/or per total treatment regimen with an increased effectiveness. Pulsed administration can provide a saving in time, effort and expense and a lower effective dose can lessen the number and severity of complications that can be experienced by a subject. As such, pulsing can be more effective than continuous administration of the same composition.

In traditional forms of therapy, repeated administration is designed to maintain a desired level of an active ingredient in the body. Very often, complications that develop can be attributed to dosage levels that, to be effective, are near toxic or otherwise harmful to normal cells. In contrast, with pulse therapy, in vivo levels of drug drop below that level required for effective continuous treatment. Therefore, pulsing is not simply the administration of a sufficiently large bolus such that there will be therapeutically sufficient high concentration of a MIS protein or MIS protein variant in the blood of the subject for a long period of time sufficient to arrest folliculogenesis for the desired time period. Pulsed administration can substantially reduce the amount of the composition comprising a MIS protein or MIS protein variant administered to the patient per dose or per total treatment regimen with an increased effectiveness. This represents a significant saving in time, effort and expense and, more importantly, a lower effective dose substantially lessens the number and severity of complications that may be experienced by the patients.

In certain embodiments, a pulsed administration comprises administering one or more MIS protein or MIS variant protein for about 4 weeks, followed by not administering a MIS protein or MIS variant protein for about 1 weeks. In some embodiments, the pulsed administration comprises administering at least one MIS protein or MIS variant protein for about 6 weeks, followed by not administering a MIS protein or MIS variant protein for about 2 weeks. In certain embodiments, the pulsed administration comprises administering at least one MIS protein or MIS variant protein for about 4 weeks, followed by not administering a MIS protein or MIS variant protein for about 2 weeks. In some embodiments, the pulsed administration comprises administering at least one MIS protein or MIS variant protein for about 2 weeks, followed by not administering a MIS protein or MIS variant protein for about 2 weeks. In some embodiments, pulsed administration comprises pulses of administering at least MIS protein or MIS variant protein for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months or longer than 12 months. In certain embodiments, pulsed administration comprises intervals of not administering a MIS protein or MIS variant protein for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months or longer than 12 months. In some embodiments, administration is continuous. In certain embodiments, administration of a MIS protein or MIS variant protein is for the lifetime of the subject, where permanent contraception is warranted or desired.

Individual pulses of a composition comprising a MIS protein or MIS protein variant as disclosed herein can be delivered to the patient continuously over a period of several hours, such as about 2, 4, 6, 8, 10, 12, 14 or 16 hours, or several days, such as 2, 3, 4, 5, 6, or 7 days, or more than 7 days, e.g., about 7-14 days, or 14 days to 3 weeks, or 3-4 weeks, or 4-6 weeks or more than 6 weeks. For example, a composition comprising a MIS protein or MIS protein variant can been administered over a period of about 10 to 20 days or 10 to 30 days, followed by a period of 7 days of no treatment.

In one embodiment, a composition comprising a MIS protein or MIS protein variant as disclosed can be administered to a subject for about 2, or about 3, or about 4, or about five weeks, or more than five weeks, e.g., about 2, or about 3, or about 4, or about 5, or about 6 or about 7 or more months, and then a subsequently administered after an appropriate interval for an additional period of time, for example, for about 2, or about 3, or about 4, or about five days, or more than five days. Cycles of treatment may occur in immediate succession or with an interval of no treatment between cycles. Typically, where the subject is administering a composition comprising a MIS protein or MIS variant protein as disclosed herein for the preservation of fertility (e.g., in a method to arrest folliculogenesis), a subject can be administered the composition for a period of between about 3-4 months, or a period of between about 4-6 months, or a period of between about 6-8 months, or a period of between about 8-12 months, or a period of between about 12-24 months, or a period of between about 24-36 months or more than about 36 months, followed by an interval of no delivery, as discussed herein. In some embodiments, where the subject is administering a composition comprising a MIS protein or MIS variant protein as disclosed herein in a method for contraception, a subject can be administered the composition for a period of between about 3-4 months, or a period of between about 4-6 months, or a period of between about 6-8 months, or a period of between about 8-12 months, or a period of between about 12-24 months, or a period of between about 24-36 months or more than about 36 months, or for as long as the subject desires not to become pregnant, followed by an interval of no delivery.

In some embodiments, where pulse therapy is used, the interval between pulses or the interval of no delivery is greater than 24 hours and preferably greater than 48 hours, and can be for even longer such as for 3, 4, 5, 6, 7, 8, 9 or 10 days, two, three or four weeks or even longer. In some embodiments, the interval between pulses can be determined by one of ordinary skill in the art, for example, as demonstrated herein in the Examples, by measuring the level of MIS protein in the blood in the subject after administration of the composition (e.g., the pulse dose), and administering a pulse when the MIS mRNA or MIS protein level reaches a certain pre-defined low threshold limit. Such pre-defined low threshold limits can be determined by one of ordinary skill in the art, and can be, for example, about baseline level, or about 100% or about 200%, or about 300%, or about 400%, or about 500% or more than 500% above the baseline level of exogenous MIS protein levels in an age-matched female subject.

Alternatively, in some embodiments, the interval between pulses can be calculated by administering another dose of a composition comprising a MIS protein or MIS protein variant as disclosed herein, and when the active component of the composition is no longer detectable in the patient prior to delivery of the next pulse. Alternatively, intervals can also be calculated from the in vivo half-life of the composition. For example, intervals can also be calculated from the in vivo half-life of the composition, or the levels of MIS protein or MIS variant protein in the blood. Intervals may be calculated as greater than the in vivo half-life, or 2, 3, 4, 5 and even 10 times greater the composition half-life. For compositions with fairly rapid half lives, intervals may be 25, 50, 100, 150, 200, 250 300 and even 500 times the half life of the chemical composition. The number of pulses in a single therapeutic regimen may be as little as two, but is typically from about 5 to 10, 10 to 20, 15 to 30 or more. In some embodiments, patients receive a composition comprising a MIS protein or MIS protein variant as disclosed herein for life, or a desired timespan where the subject does not wish to become pregnant, according to the methods of this invention without the problems and inconveniences associated with current therapies.

In certain embodiments, a composition comprising a MIS protein or MIS protein variant as disclosed herein can be administered by most any means, but are preferable delivered to the patient as an injection (e.g. intravenous, subcutaneous, intraarterial), infusion or instillation, and more preferably by oral ingestion or intravaginal administration.

In some embodiments, administration of a composition comprising a MIS protein or MIS protein variant as disclosed herein can be intermittent; for example, administration can be once every two days, every three days, every five days, once a week, once or twice a month, and the like. The amount, forms, and/or amounts of the different forms of a composition comprising a MIS protein or MIS protein variant as disclosed herein can be varied at different times of administration.

In some embodiments, a composition comprising a MIS protein or MIS protein variant as disclosed herein can be administered to a subject before a chemotherapeutic treatment, immunotherapy, cytotoxic therapeutic, surgery, or radiation treatment is administered to the subject. In alternative embodiments, a composition comprising a MIS protein or MIS protein variant as disclosed herein can be co-administered to a subject concurrently with another agent or treatment regimen, e.g., concurrently with a chemotherapeutic treatment, immunotherapy, cytotoxic therapeutic, surgery, or radiation treatment. In some embodiments, a composition comprising a MIS protein or MIS protein variant as disclosed herein can be co-administered with a pharmaceutical composition comprising an comprising one or more addition agents. The pharmaceutical compositions can be provided by pulsed administration. For example, a composition comprising a MIS protein or MIS protein variant as disclosed herein can be administered to a subject, followed by a chemotherapeutic treatment, or radiation treatment after an interval of time has passed, and this order of administration the same or similar time interval can be repeated, for example, at least 1, 2, 3, 4, 5, 6, 7, 8, 9, or 10 or more times. Pulsed administration of one or more pharmaceutical compositions comprising a MIS protein or MIS protein variant as disclosed herein can be used for prophylactic treatment, for example, a subject who will, or has or is currently undergoing chemotherapy and chemoradiation therapy, to avoid chemotherapy or radiotherapy-induced premature ovarian failure.

In some embodiments, a subject can receive one or more compositions comprising a MIS protein or MIS protein variant as disclosed for life according to the methods of this invention, for example, where the subject has a desire to permanently prevent pregnancy, e.g., for animal subjects such as cats and dogs. Compositions can be administered by most any means, and can be delivered to the subject as an oral formulation, or injection (e.g. intravenous, subcutaneous, intraarterial), infusion or instillation. Various methods and apparatus for pulsing compositions by infusion or other forms of delivery to the patient are disclosed in U.S. Pat. Nos. 4,747,825; 4,723,958; 4,948,592; 4,965,251 and 5,403, 590, which are incorporated herein in their entirety by reference.

While the attending physician ultimately will decide the appropriate amount and dosage regimen, an effective amounts of a recombinant human MIS protein or derivative or functional fragment thereof can be provided at a dose of 0.0001, 0.01, 0.01 0.1, 1, 5, 10, 25, 50, 100, 500, or 1,000 mg/kg. Effective doses may be extrapolated from dose-response curves derived from in vitro or animal model test bioassays or systems. In some embodiments, doses of a recombinant human MIS protein are about 1 pg/kg to 10 mg/kg (body weight of patient) although lower and higher doses can also be administered.

In some embodiments, reference ranges for doses of recombinant human MIS are estimated from reference groups in the United States, and are disclosed in Antimullerian Hormone (AMH), Serum from Mayo Medical Laboratories. Retrieved April 2012. In some embodiments, female subjects can be administered the following doses of recombinant human MIS: females 13-45 years: 1 to 10 ng/mL; females older than 45 years: Less than 1 ng/mL. It is noted that MIS measurements may be less accurate if the person being measured is vitamin D deficient.

Dosages for a particular patient or subject can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of a recombinant human MIS protein or functional derivatives or functional fragments thereof as disclosed herein, and the condition of the patient, the autoimmune disease to be treated, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising a recombinant human MIS protein or functional derivatives or functional fragments thereof are optionally tested in one or more appropriate in vitro and/or in vivo animal models of disease, such as an Mullerian duct regression bioassay as disclosed herein in the Examples, and known to persons of ordinary skill in the art, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of a recombinant human MIS protein or functional derivatives or functional fragments thereof at various concentrations, e.g., as applied to the mass and overall health of the patient. Administration can be accomplished via single or divided doses.

In determining the effective amount of a recombinant human MIS protein, MIS variant protein (e.g., LR-MIS protein) or functional derivatives or functional fragments thereof, or nucleic acids encoding the same, to be administered in the treatment or prophylaxis of a disease, the physician evaluates circulating plasma levels of MIS proteins, formulation toxicities, and progression of the disease. The selected dosage level will also depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

In some embodiments, a recombinant human MIS protein or MIS variant protein (e.g., LR-MIS protein), or nucleic acid encoding the same, as disclosed herein can be administered at a dose in accordance with good medical practice, taking into account the clinical condition of the individual patient, the site and method of administration, scheduling of administration, patient age, sex, body weight and other factors known to medical practitioners.

Dosage regimens of a composition comprising a recombinant human MIS protein, MIS variant protein (e.g., LR-MIS protein) or functional fragment or variant thereof, or nucleic acid encoding the same, as disclosed herein can be adjusted to provide the optimum desired response (e.g. a therapeutic or prophylactic response). For example, a single bolus can be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage.

Furthermore, actual dosage levels of a recombinant human MIS protein or MIS variant protein (e.g., LR-MIS protein) in a pharmaceutical composition can be varied so as to obtain an amount of the active ingredient which is effective to achieve the desired therapeutic response for a particular subject, composition, and mode of administration, without being toxic to the subject. A pharmaceutical composition comprising a recombinant human MIS protein or functional fragment or variant thereof as disclosed herein can be a "therapeutically effective amount" and/or a "prophylactically effective amount". In general, a suitable daily dose of a composition comprising a recombinant human MIS protein or functional fragment or variant thereof as disclosed herein will be that amount of the a recombinant human MIS protein which is the lowest dose effective to produce a therapeutic effect, such as a reduction of a symptom of a proliferative disorder or cancer as disclosed herein. Such an effective dose will generally depend upon the factors described above.

If desired, the effective daily dose of a composition comprising a recombinant human MIS protein or functional fragment or variant thereof can be administered as two, three, four, five, six or more sub-doses administered separately at appropriate intervals throughout the day, optionally, in unit dosage forms.

The dosage level administered to a subject can be constant over a desired period of time, for example, at least 1 week, at least 2 weeks, at least 3 weeks, at least 1 month, at least 2 months, at least 3 months, at least 6 months, at least 1 year, or at least 5 years or more than 5 years. Alternatively, the dosage level administered to a subject can vary depending on the progression of the condition being treated, e.g., depending the FOR (functional ovarian reserve) of the subject, or severity of the POA or DOR (diminished ovarian reserve).

It is to be noted that dosage values may vary depending on, for example, the females FOR (functional ovarian reserve), or severity of the POA or DOR (diminished ovarian reserve) to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. An appropriate experimental model which can be used includes determining a the dose can be use of the mullerian duct regression bioassay as disclosed herein in the examples, or a in vivo cancer model which is commonly known by ordinary skill in the art. In vivo cancer models are discussed in Frese et al., "Maximizing mouse cancer models" Nat Rev Cancer. 2007 September; 7(9):645-58 and Santos et al., Genetically modified mouse models in cancer studies. Clin Transl Oncol. 2008 December; 10(12):794-803, and "Cancer stem cells in mouse models of cancer", 6th Annual MDI Stem Cell Symposium, MDI Biological Lab, Salisbury Cove, Me., Aug. 10-11, 2007" which are incorporated herein in their entirety by reference.

For example, a therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is dependent of the desired therapeutic effect. For example, the therapeutically effective amount of a recombinant human MIS protein can be assessed in a mouse model of fertility.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. It is also noted that humans are treated generally longer than the mice or other experimental animals exemplified herein, which treatment has a length proportional to the length of the disease process and drug effectiveness. The doses may be single doses or multiple doses over a period of several days, but single doses are preferred.

In some embodiments, a recombinant human MIS protein (e.g., proteins or nucleic acids encoding a recombinant human MIS protein or fragments thereof) can be administered to humans and other animals for therapy by any suitable route of administration, including orally, nasally, as by, for example, a spray, rectally, intravaginally, parenterally, intracisternally and topically, as by powders, ointments or drops, including buccally and sublingually.

After formulation with an appropriate pharmaceutically acceptable carrier in a desired dosage, a pharmaceutical composition comprising a recombinant human MIS protein or functional fragment or variant thereof as disclosed herein can be administered to a subject. A pharmaceutical a composition comprising a recombinant human MIS protein, or MIS variant protein (e.g., LR-MIS protein), or functional fragment or variant thereof can be administered to a subject using any suitable means. In general, suitable means of administration include, but are not limited to, topical, oral, parenteral (e.g., intravenous, subcutaneous or intramuscular), rectal, intracisternal, intravaginal, intraperitoneal, ocular, or nasal routes.

In a specific embodiment, it may be desirable to administer the pharmaceutical composition comprising a recombinant human MIS protein locally to the area in need of treatment (e.g., the ovary); this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes. In some embodiments, a recombinant human MIS protein as disclosed herein can be applied to the muscle using topical creams, patches, intramuscular injections and the like. Alternatively, recombinant MIS can be administered to an area in need treatment by viral delivery of MIS (e.g., the use of a virus comprising MIS and an ovarian-specific promoter for MIS delivery to the ovary).

In some embodiments, a recombinant human MIS protein as disclosed herein can be administered vaginally, e.g., using including hydrogels, vaginal tablets, pessaries/suppositories, particulate systems, and intravaginal rings, as known to one of ordinary skill in the art and disclosed in Woolfson et al., "Drug delivery by the intravaginal route" Crit Rev. Ther. Drug Carrier Syst., 2000 (17(5); 509-599, which is incorporated herein in its entirety by reference. In some embodiments, a recombinant human MIS protein as disclosed herein can be administered vaginally using vaginal mucoadhesive drug delivery systems (DDS), as disclosed in Maurya S K et al., "Therapeutic potential of mucoadhesive drug delivery systems—an updated patent review" Recent Pat Drug Deliv Formul. 2010 November; 4(3):256-65; Balaglu et al., "Strategies to prolong the intravaginal residence time of drug delivery systems" J Pharm Pharm Sci. 2009; 12(3): 312-36 and de Araújo Pereira; "Vaginal mucoadhesive drug delivery systems" Drug Dev Ind Pharm. 2012 June; 38(6): 643-52, which are incorporated herein in their entirety by reference. In some embodiments, a recombinant human MIS protein as disclosed herein can be administered vaginally using mucoadhesive microspheres, as disclosed in Krutik et al., "Mucoadhesive microspheres: a promising tool in drug delivery" Patil et al., Curr Drug Deliv 2008 October; 5(4): 312-8.

In some embodiments, a recombinant human MIS protein can be administered to a subject orally (e.g., in capsules, suspensions or tablets) or by parenteral administration. Conventional methods for oral administration include administering a recombinant human MIS protein in any one of the following; tablets, suspensions, solutions, emulsions, capsules, powders, syrups and the like are usable. Known techniques that deliver a recombinant human MIS protein orally or intravenously and retain the biological activity are preferred. Parenteral administration can include, for example, intramuscular, intravenous, intraarticular, intraarterial, intrathecal, subcutaneous, or intraperitoneal administration. A recombinant human MIS protein can also be administered orally, transdermally, topically, by inhalation (e.g., intrabronchial, intranasal, oral inhalation or intranasal drops) or rectally. Administration can be local or systemic as indicated. Agents, e.g., nucleic acid agents which encode a recombinant human MIS protein or functional fragment thereof can also be delivered using a vector, e.g., a viral vector by methods which are well known to those skilled in the art.

When administering a composition comprising a recombinant human MIS protein or functional fragment or variant thereof as disclosed herein parenterally, it will generally be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol), suitable mixtures thereof, and vegetable oils.

The term "Dosage unit" form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the a recombinant human MIS protein or functional fragment or variant thereof as disclosed herein and the particular therapeutic or prophylactic effect to be achieved, and (b) the limitations inherent in the art of compounding a recombinant human MIS protein an active agent for the treatment of sensitivity in individuals.

The pharmaceutically acceptable compositions comprising a recombinant human MIS protein or functional fragment or variant thereof as disclosed herein can be suspended in aqueous vehicles and introduced through conventional hypodermic needles of a infusion pumps or cannula of an on-body injectors.

Pharmaceutical Compositions

In some embodiments, a composition comprising a recombinant human MIS protein, or MIS variant protein or functional fragment or variant thereof as disclosed herein can be formulated in any suitable means, e.g., as a sterile injectable solution, e.g., which can be prepared by incorporating the recombinant human MIS protein in the required amount of the appropriate solvent with various of the other ingredients, as desired.

A pharmacological formulation of a composition comprising a recombinant human MIS protein, or MIS variant protein (e.g., LR-MIS) or nucleic acid encoding the same as disclosed herein can be administered to the patient in an injectable formulation containing any compatible carrier, such as various vehicles, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those presented in U.S. Pat. Nos. 5,225, 182; 5,169,383; 5,167,616; 4,959,217; 4,925,678; 4,487, 603; 4,486,194; 4,447,233; 4,447, 224; 4,439,196 and 4,475, 196. Other such implants, delivery systems, and modules are well known to those skilled in the art.

Proper fluidity can be maintained, for example, by the use of a coating such as lecithin, by the maintenance of the required particle size in the case of dispersion and by the use of surfactants. Non-aqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, e.g., parabens, chlorobutanol, phenol and sorbic acid. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

In another embodiment, a composition comprising a recombinant human MIS protein, or MIS variant protein or nucleic acid encoding the same as disclosed herein can comprise lipid-based formulations. Any of the known lipid-based drug delivery systems can be used in the practice of the invention. For instance, multivesicular liposomes, multilamellar liposomes and unilamellar liposomes can all be used so long as a sustained release rate of the encapsulated active compound can be established. Methods of making controlled release multivesicular liposome drug delivery systems are described in PCT Application Publication Nos: WO 9703652, WO 9513796, and WO 9423697, the contents of which are incorporated herein by reference.

In some embodiments, the composition used in the methods described herein can be in a controlled release form. A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008, 719; 5,674,533; 5,059,595; 5,591,767; 5,120,548; 5,073, 543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The composition of the synthetic membrane vesicle is usually a combination of phospholipids, usually in combination with steroids, especially cholesterol. Other phospholipids or other lipids may also be used. Examples of lipids useful in synthetic membrane vesicle production include phosphatidylglycerols, phosphatidylcholines, phosphatidylserines, phosphatidylethanolamines, sphingolipids, cerebrosides, and gangliosides, with preferable embodiments including egg phosphatidylcholine, dipalmitoylphosphatidylcholine, distearoylphosphatidyleholine, dioleoylphosphatidylcholine, dipalmitoylphosphatidylglycerol, and dioleoylphosphatidylglycerol.

In preparing lipid-based vesicles containing a recombinant human MIS protein or functional fragment or variant thereof, such variables as the efficiency of active compound encapsulation, lability of the active compound, homogeneity and size of the resulting population of vesicles, active compound-to-lipid ratio, permeability, instability of the preparation, and pharmaceutical acceptability of the formulation should be considered.

In another embodiment, a recombinant human MIS protein, or MIS variant protein (e.g., LR-MIS) can be delivered in a vesicle, in particular a liposome (see Langer (1990) Science 249:1527-1533). In yet another embodiment, a recombinant human MIS protein can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a recombinant human MIS protein, or MIS variant protein (e.g., LR-MIS), the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

Prior to introduction, a composition comprising a recombinant human MIS protein, or MIS variant protein (e.g., LR-MIS) or functional fragment or variant thereof as disclosed herein can be sterilized, by any of the numerous available techniques of the art, such as with gamma radiation or electron beam sterilization.

In another embodiment of the invention, a composition comprising a recombinant human MIS protein, or MIS variant protein (e.g., LR-MIS) or functional fragment or variant thereof as disclosed herein, can be administered and/or formulated in conjunction (e.g., in combination) with any other therapeutic agent. For purpose of administration, a recombinant human MIS protein or functional fragment or variant thereof as disclosed herein is preferably formulated as a pharmaceutical composition. Pharmaceutical compositions of the present invention comprise a compound of this invention and a pharmaceutically acceptable carrier, wherein the compound is present in the composition in an amount which is effective to treat the condition of interest. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds of this invention in an appropriate manner, and in accordance with accepted practices, such as those disclosed in Remington's Pharmaceutical Sciences, Gennaro, Ed., Mack Publishing Co., Easton, Pa. 1990.

The compositions of the present invention can be in any form. These forms include, but are not limited to, solutions, suspensions, dispersions, ointments (including oral ointments), creams, pastes, gels, powders (including tooth powders), toothpastes, lozenges, salve, chewing gum, mouth sprays, pastilles, sachets, mouthwashes, aerosols, tablets, capsules, transdermal patches, that comprise one or more resolvins and/or protectins or their analogues of the invention.

The composition can be in the form of a pill intended for continuous administration (e.g., sustained-release pill or capsule). "Sustained-release", "sustained-action", "extended-release", "time-release or timed-release", "controlled-release", "modified release", or "continuous-release" refer to formulations that allow the active ingredient (e.g., recombinant MIS protein) to be released over time, and are used to maintain a more consistent level of the active ingredient in the body (e.g., in the bloodstream), and are known in the art.

Formulations of a composition comprising a recombinant human MIS protein, or MIS variant protein (e.g., LR-MIS) or functional fragment or variant thereof as disclosed herein can be prepared by a number or means known to persons skilled in the art. In some embodiments the formulations can be prepared for administration as an aerosol formulation, e.g., by combining (i) a recombinant human MIS protein, or MIS variant protein (e.g., LR-MIS) or functional fragment or variant thereof as disclosed herein in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

In certain embodiments, a composition comprising a recombinant human MIS protein, or MIS variant protein (e.g., LR-MIS) as disclosed herein can be administered to a subject as a pharmaceutical composition with a pharmaceutically acceptable carrier. In certain embodiments, these pharmaceutical compositions optionally further comprise one or more additional therapeutic agents. Of course, such therapeutic agents are which are known to those of ordinary skill in the art can readily be identified by one of ordinary skill in the art.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Formulations of the invention suitable for oral administration of a MIS protein, or MIS variant protein (e.g., LR-MIS) may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), of a MIS protein or, or MIS variant protein (e.g., LR-MIS) is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some instances, a composition comprising a recombinant human MIS protein or functional fragment or variant thereof as disclosed herein can be in a formulation suitable for rectal or vaginal administration, for example as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore release the active compound. Suitable carriers and formulations for such administration are known in the art.

Dosage forms for the topical or transdermal administration of a recombinant human MIS protein of this invention, e.g., for muscular administration include powders, sprays, ointments, pastes, creams, lotions, gels, solutions, patches and inhalants A recombinant human MIS protein or functional fragment or variant thereof as disclosed herein may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a recombinant human MIS protein of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In certain embodiments, a recombinant human MIS protein, or MIS variant protein (e.g., LR-MIS) or functional fragment or variant thereof can be isolated and/or purified or substantially purified by one or more purification methods described herein or known by those skilled in the art. Generally, the purities are at least 90%, in particular 95% and often greater than 99%. In certain embodiments, the naturally occurring compound is excluded from the general description of the broader genus.

In some embodiments, the composition comprises at least one a recombinant human MIS protein, or MIS variant protein (e.g., LR-MIS) in combination with a pharmaceutically acceptable carrier. Some examples of materials which can serve as pharmaceutically acceptable carriers include, without limitation: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, a composition comprising a recombinant human MIS protein, or MIS variant protein (e.g., LR-MIS) or functional fragment or variant thereof as disclosed herein can contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention.

These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs" are salts or prodrugs that are, within the scope of sound medical judgment, suitable for use in contact with the tissues of patients without undue toxicity, irritation, allergic response, and the like, commensurate with a reasonable benefit/risk ratio, and effective for their intended use. These compounds include the zwitterionic forms, where possible, of r compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "prodrug" refers to compounds or agents that are rapidly transformed in vivo to yield the active recombinant human MIS protein, e.g., a biologically active or functional active MIS protein or nucleic acid (e.g., mRNA, DNA, MOD-RNA) which encodes a functionally active MIS protein. In some embodiments, a recombinant human MIS protein prodrug can be activated by hydrolysis in blood, e.g., via cleavage of a leader sequence, and or cleavage at the primary cleavage site to result in the N-terminal and C-terminal domains for production of a bioactive MIS protein, similar to how insulin is activated from its proprotein into an active insulin protein. A thorough discussion is provided in T. Higachi and V. Stella, "Pro-drugs as Novel Delivery Systems," Vol. 14 of the A.C.S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. The prodrug may be designed to alter the metabolic stability or the transport characteristics of a recombinant human MIS protein, to mask side effects or toxicity, or to alter other characteristics or properties of the recombinant human MIS protein.

By virtue of knowledge of pharmacodynamic processes and drug metabolism or post-translational protein processing of MIS in vivo, once a pharmaceutically active compound is identified, those of skill in the pharmaceutical art generally can design a recombinant human MIS protein prodrug which can be activated in vivo to increase levels of a bioactive MIS protein in the subject (see, e.g., Nogrady (1985) Medicinal Chemistry A Biochemical Approach, Oxford University Press, N.Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

As discussed herein, in some embodiments a composition comprising a recombinant human MIS protein, or MIS variant protein (e.g., LR-MIS) or functional fragment or variant thereof as disclosed herein can be conjugated or covalently attached to a targeting agent to increase their tissue specificity and targeting to a cell, for example a muscle cells. Targeting agents can include, for example without limitation, antibodies, cytokines and receptor ligands, as discussed in the section entitled "targeting." In some embodiments, the targeting agent is overexpressed on the cells to be targeted, for example the muscle cells as compared to non-muscle cells.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Combination Therapy

In one embodiment, a recombinant MIS protein is administered as a monotherapy. In one embodiment, the recombinant MIS protein is administered in combination with a chemotherapeutic agent, an anti-tumor agent, radiation, or surgery. Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzumab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®). Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel R, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®). Exemplary mTOR inhibitors include, e.g., temsirolimus; ridaforolimus (formally known as deferolimus, (1R,2R,45)-4-[(2R)-2[(1R, 95,125,15R,16E,18R,19R,21R,235,24E,26E,28Z,305,325, 35R)-1,18-dihydroxy-19,30-dimethoxy-15,17,21,23,29,35-hexamethyl-2,3,10,14,20-pentaoxo-11,36-dioxa-4-azatricyclo[30.3.1.04'9] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor R or RADOO1); rapamycin (AY22989, Sirolimust); simapimod (CAS 164301-51-3); emsirolimus, (5-{2,4-Bis[(35)-3-methylmorpholin-4-yl]pyrido[2,3-(i]pyrimidin-7-yl}-2-methoxyphenyl)methanol (AZD8055); 2-Amino-8-[iraw5,-4-(2-hydroxyethoxy)cyclohexyl]-6-(6-methoxy-3-pyridinyl)-4-methyl-pyrido[2,3-JJpyrimidin-7(8H)-one (PF04691502, CAS 101310]-36-4); and N2-[1,4-dioxo-4-[[4-(4-oxo-8-phenyl-4H-1-benzopyran-2-yl)morpholinium-4-yl]methoxy]butyl]-L-arginylglycyl-L-a-aspartylL-serine- (SEQ ID NO: 21), inner salt (SF1126, CAS 936487-67-1), and XL765. Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics). Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin. Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary proteosome inhibitors include bortezomib (Velcade®); carfilzomib (PX-171-007, (5)-4-Methyl-N-05)-1-4(5)-4-methyl-1-((R)-2-methyloxiran-2-yl)-1-oxopentan-2-yl)amino)-1-oxo-3-phenylpropan-2-yl)-2-((5)-2-(2-morpholinoacetamido)-4-phenylbutanamido)-pentanamide); marizomib (NPT0052); ixazomib citrate (MLN-9708); delanzomib (CEP-18770); and O-Methyl-N-[(2-methyl-5-thiazolyl)carbonyl]-L-seryl-O-methyl-N-[(11S')-2-[(2R)-2-methyl-2-oxiranyl]-2-oxo-1-(phenylmethyl)ethyl]-L-serinamide (ONX-0912).

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff s Clinical Oncology, 2013 Elsevier; and Fischer D S (ed): The Cancer Chemotherapy Handbook, 4th ed. St. Louis, Mosby-Year Book, 2003).

In one embodiment, the recombinant MIS protein is administered in combination with a checkpoint inhibitor. A checkpoint inhibitor can be a small molecule, inhibitory RNA/RNAi molecule (both single and double stranded), an antibody, antibody reagent, or an antigen-binding fragment thereof that specifically binds to at least one immune checkpoint protein. Common checkpoints that are targeted for therapeutics include, but are not limited to PD-1, CTLA4, TIM3, LAG3 and PD-L1. Inhibitors of their checkpoint regulators are known in the art.

Non-limiting examples of checkpoint inhibitors (with checkpoint targets and manufacturers noted in parentheses) can include: MGA271 (B7-H3: MacroGenics); ipilimumab (CTLA-4; Bristol Meyers Squibb); pembrolizumab (PD-1; Merck); nivolumab (PD-1; Bristol Meyers Squibb); atezolizumab (PD-L1; Genentech); galiximab (B7.1; Biogen); IMP321 (LAG3: Immuntep); BMS-986016 (LAG3; Bristol Meyers Squibb); SMB-663513 (CD137; Bristol-Meyers Squibb); PF-05082566 (CD137; Pfizer); IPH2101 (KIR; Innate Pharma); KW-0761 (CCR4; Kyowa Kirin); CDX-1127 (CD27; CellDex); MEDI-6769 (Ox40; MedImmune); CP-870,893 (CD40; Genentech); tremelimumab (CTLA-4; Medimmune); pidilizumab (PD-1; Medivation); MPDL3280A (PD-L1; Roche); MEDI4736 (PD-L1; AstraZeneca); MSB0010718C (PD-L1; EMD Serono); AUNP12 (PD-1; Aurigene); avelumab (PD-L1; Merck); durvalumab (PD-L1; Medimmune); TSR-022 (TIM3; Tesaro).

In on embodiment, the recombinant MIS proteins is administered in combination with a immunotherapy (e.g., a drug or agent used to treat a auto-immune disease). Exemplary immunotherapies include immune globulin intravenous (IGIV), azathioprine, imuran, budesonide, purinethol, mercaptopurine, mycophenolate mofetil, azasan, infliximab, methotrexate, prednisone, cyclophosphamide, cyclosporine, etanercept, anakinra, cortisone, hydrocortisone, celecoxib, diclofenac, diclofenac-misoprostol, diflunisal, etodolac, fenoprofen, flurbiprofen, indomethacin, ketorolac, ketoprofen, nabumetone, meclofenamate, mefenamic acid, meloxicam, nabumetone, oxaprozin, piroxicam, salsalate, sulindac, tolmetin, aspirin, ibuprofen, and naproxen.

The recombinant MIS protein can be administered in combination with a radiotherapy, chemo-radiotherapy, or surgery to remove all or part of a tumor and optionally, the surrounding tissue. Radiation and surgery for treatment of cancer are known in the art, and can be administered and/or performed by a skilled person.

In one embodiment, the recombinant MIS protein is administered is administered prior to administration of at least a second therapeutic drug or agent (e.g., a chemotherapeutic, or immunotherapy). The recombinant MIS protein is administered is administered after the administration of at least a second therapeutic drug or agent. Administration of the recombinant MIS protein and at least the second therapeutic drug or agent can be done at different time points, or at substantially the same time. The recombinant MIS protein can be comprised within a composition comprising at least a second therapeutic drug or agent (e.g., comprised in a composition comprising a chemotherapeutic or immunotherapy).

In some embodiments, the present invention may be defined in any of the following numbered paragraphs:

1. A method for ovarian protection in a female subject, comprising administering to the female subject a composition comprising a recombinant Mullerian Inhibiting Substance (MIS) protein, wherein the recombinant MIS protein comprises a modification of at least one amino acid between residues 448-451 of SEQ ID NO: 3 (MIS) to increase cleavage as compared to in the absence of the modification.
2. A method for uterine protection in a female subject, comprising administering to the female subject a composition comprising a recombinant Mullerian Inhibiting Substance (MIS) protein, wherein the recombinant MIS protein comprises a modification of at least one amino acid between residues 448-451 of SEQ ID NO: 3 (MIS) to increase cleavage as compared to in the absence of the modification.
3. The method of paragraph 1, wherein the ovarian protection is oncoprotection.
4. A method for treating polycystic ovarian syndrome (PCOS) in a female subject, comprising administering to the female subject a composition comprising a recombinant Mullerian Inhibiting Substance (MIS) protein, wherein the recombinant MIS protein comprises a modification of at least one amino acid between residues 448-451 of SEQ ID NO: 3 (MIS) to increase cleavage as compared to in the absence of the modification.
5. The method of any of paragraphs 1-4, wherein the recombinant MIS protein comprises amino acid residues 25-559 of SEQ ID NO: 4 (LR-MIS) or a polypeptide which has at least 85% sequence identity to the amino acid sequence of amino acid residues 25-559 of SEQ ID NO: 4 (LR-MIS).
6. The method of any of paragraphs 1-5, wherein the recombinant MIS protein is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS), wherein optionally, amino acid residue 452 of SEQ ID NO: 1 is changed from S to R.
7. The method of any of paragraphs 1-7, wherein the recombinant MIS protein does not comprise a FLAG tag.
8. The method of any of paragraphs 1-8, wherein the female subject has cancer and will be treated with, or is currently being treated with, or has been treated with, a cancer treatment selected from chemotherapy, radiotherapy, chemo-radiotherapy, or surgery.
9. The method of any of paragraphs 1-8, wherein the female subject has an autoimmune disease and will be treated with, or is currently being treated with, or has been treated with, an immunotherapy.
10. The method of any of paragraphs 1-8, wherein the female subject will be treated with, or is currently being treated with, or has been treated with, a cytotoxic drug or cytotoxic agent that causes cell death or cell damage to cells in the uterus or ovary.
11. The method of any of paragraphs 1-8, wherein the female subject will be treated with, or is currently being treated with, or has been treated with, a long-term treatment regimen.
12. The method of paragraph 1, wherein ovarian protection is reducing folliculogenesis in the female subject, or reducing the number of primordial follicles being recruited by at least 10% as compared to in the absence of the recombinant MIS protein, or reducing the number of primordial follicles being recruited by between 10% and 99%, or is a complete arrest in folliculogenesis, or is a slowing down of primordial follicle activation, as compared to in the absence of the recombinant MIS protein.
13. The method of paragraph 2, wherein uterine protection is a reduction in uterine damage or a reduction in any of: uterine dysfunction, uterine lining thinning, uterine dystocia, likelihood of premature birth, implantation failure, pregnancy loss/miscarriage, pregnancy-induced hypertension or preeclampsia, or fetal growth restriction.
14. The method of paragraph 4, wherein treating PCOS is reducing folliculogenesis in the female subject, or reducing the number of primordial follicles being recruited by at least 10% as compared to in the absence of the recombinant MIS protein, or reducing the number of primordial follicles being recruited by between 10% and 99%, or is a complete arrest in folliculogenesis, or is a slowing down of primordial follicle activation, as compared to in the absence of the recombinant MIS protein.
15. The method of any of paragraphs 1-14, wherein the recombinant MIS protein is administered as a continuous administration or via pulse administration (e.g., 1.5 mg/kg twice a day).
16. The method of paragraph 15, wherein the continuous administration is via an infusion or pump administration, transdermal patch administration, or subcutaneous injection administration.
17. The method of any of paragraphs 1-16, wherein the recombinant MIS protein is administered at a high level sufficient to arrest folliculogenesis or keep the ovary in a quiescent state.
18. The method of paragraph 17, wherein the high levels of recombinant MIS protein is sufficient to result in any of the following:
    a. a concentration of MIS protein in the blood of the subject that is 10% to 50% higher as compared to the absence of administration of the recombinant MIS protein;
    b. a concentration of MIS protein in the blood of the subject that is 50% to 100% higher as compared to the absence of administration of the recombinant MIS protein;
    c. a concentration of MIS protein in the blood of the subject that is 2 to 5-fold higher or more than 5-fold higher as compared to the absence of administration of the recombinant MIS protein; or
    d. a concentration of MIS protein in the blood of the subject of between 1 µg/ml-5 µg/ml.
19. The method of any of paragraphs 17-18, wherein the high levels of recombinant MIS protein is administered between 0.001 mg/kg per hour and 0.1 mg/kg per hour, or between 0.2 µg/hr and 10.0 µg/hr.
20. The method of any of paragraphs 1-19, wherein the female subject is a human subject.

21. The method of any of paragraphs 1-20, wherein the female subject is a pre-pubescent female subject.
22. The method of any of paragraphs 1-21, wherein the female subject is in need of preserving their ovarian reserve, or who has a need to delay reproduction to a later time point, or wherein the female subject has, or is pre-disposed to any of the following: diminished ovarian reserve (DOR), premature ovarian aging (POA), primary ovarian insufficiency (POI), endometriosis, polycystic ovarian syndrome (PCOS), one or more FMR1 premutations or 55-200 GCC FMR1 repeats, BRAC1 mutations, Turner syndrome, an autoimmune disease, an ovarian autoimmune disease (e.g., oophoritis) thyroid autoimmunity, adrenal autoimmunity or autoimmunity polyglandular syndromes.
23. The method of any of paragraphs 1-22, wherein the female subject is in need of fertility preservation.
24. The method of any of paragraphs 1-23, wherein administering the MIS protein prevents the female from getting pregnant.
25. The method of any of paragraphs 1-24, wherein administering the MIS protein is a means of temporary contraception or short-term contraception.
26. The method of any of paragraphs 1-24, wherein administering the MIS protein allows the female to control cycling and/or control of reproductive hormones, and/or slow down primordial follicle activation.
27. The method of any of paragraphs 1-26, wherein the female subject will undergo, or has undergone an ovarian tissue graft or cortical ovarian tissue graft.
28. The method of any of paragraphs 1-27, wherein the MIS protein is administered in combination with, or concurrently with a chemotherapeutic agent or anti-cancer therapy.
29. The method of any of paragraphs 1-27, wherein the MIS protein is administered prior to administration of a chemotherapeutic agent or anti-cancer therapy.
30. The method of any of paragraphs 28-29, wherein the anti-cancer therapy is radiotherapy, chemo-radiotherapy, or surgery.
31. The method of paragraphs 4, 29 and 30, wherein the chemotherapeutic agent is selected from a platinum chemotherapeutic agent, an anthracyclin therapeutic agent, or an alkylating chemotherapeutic agent.
32. The method of any of paragraphs 1-27, wherein the MIS protein is administered in combination with, or concurrently with an immunotherapy agent.
33. The method of any of paragraphs 1-27, wherein the MIS protein is administered prior to administration of a immunotherapy agent.
34. The method of any of paragraphs 1-27, wherein the MIS protein is administered in combination with, or concurrently with at least a second therapeutic agent.
35. The method of any of paragraphs 1-27, wherein the MIS protein is administered prior to administration of at least a second therapeutic agent.
36. The method of any of paragraphs 34-35, wherein the second therapeutic agent is a cytotoxic drug, or cytotoxic agent that causes cell death or cell damage to cells in the uterus or ovary.
37. The method of paragraph 1 or 3, further comprising, prior to administering, selecting a subject in need of ovarian protection or oncoprotection.
38. The method of paragraph 2, further comprising, prior to administering, selecting a subject in need of uterine protection.
39. The method of paragraph 4, further comprising, prior to administering, selecting a subject in need of treatment for PCOS.
40. The method of paragraph 4, further comprising, prior to administering, selecting a subject who has previously been diagnosed with PCOS.
41. The method of paragraph 4, further comprising, prior to administering, diagnosing a subject with PCOS.
42. A kit for use in ovarian protection or oncoprotection of a female subject comprising:
    a. a pump or infusion device comprising:
        i. a recombinant MIS protein, wherein the recombinant MIS protein comprises amino acid residues 25-559 of SEQ ID NO: 4 (LR-MIS) or a polypeptide which has at least 85% sequence identity to the amino acid sequence of amino acid residues 25-559 of SEQ ID NO: 4 (LR-MIS); or
        ii. a recombinant MIS protein, wherein the recombinant MIS protein is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS), wherein optionally, amino acid residue 452 of SEQ ID NO: 1 is changed from S to R; and
    b. instructions for implanting the pump or infusion device into the female subject for the treatment of a subject with one or more of: a diminished ovarian reserve (DOR), premature ovarian aging (POA), primary ovarian insufficiency (POI), endometriosis, polycystic ovarian syndrome (PCOS), one or more FMR1 premutations or 55-200 GCC FMR1 repeats, or where the subject is undergoing, has, or will undergo a cancer treatment.
43. A kit for use in uterine protection of a female subject comprising:
    a. a pump or infusion device comprising:
        i. a recombinant MIS protein, wherein the recombinant MIS protein comprises amino acid residues 25-559 of SEQ ID NO: 4 (LR-MIS) or a polypeptide which has at least 85% sequence identity to the amino acid sequence of amino acid residues 25-559 of SEQ ID NO: 4 (LR-MIS); or
        ii. a recombinant MIS protein, wherein the recombinant MIS protein is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS), wherein optionally, amino acid residue 452 of SEQ ID NO: 1 is changed from S to R; and
    b. instructions for implanting the pump or infusion device into the female subject for the treatment of a subject with one or more of: a diminished ovarian reserve (DOR), premature ovarian aging (POA), primary ovarian insufficiency (POI), endometriosis, polycystic ovarian syndrome (PCOS), one or more FMR1 premutations or 55-200 GCC FMR1 repeats, or where the subject is undergoing, has, or will undergo a cancer treatment.

44. A kit for use in treatment of polycystic ovarian syndrome (PCOS) of a female subject comprising:
    a. a pump or infusion device comprising:
       i. a recombinant MIS protein, wherein the recombinant MIS protein comprises amino acid residues 25-559 of SEQ ID NO: 4 (LR-MIS) or a polypeptide which has at least 85% sequence identity to the amino acid sequence of amino acid residues 25-559 of SEQ ID NO: 4 (LR-MIS); or
       ii. a recombinant MIS protein, wherein the recombinant MIS protein is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS), wherein optionally, amino acid residue 452 of SEQ ID NO: 1 is changed from S to R; and
    b. instructions for implanting the pump or infusion device into the female subject for the treatment of a subject with one or more of: polycystic ovarian syndrome (PCOS), one or more FMR1 premutations or 55-200 GCC FMR1 repeats, and/or where the subject is undergoing, has, or will undergo a cancer treatment.

45. The kit of any of paragraphs 42-44, wherein the pump is an osmotic pump.

46. The kit of any of paragraphs 42-44, wherein the infusion device is a transdermal patch.

47. The kit of any of paragraphs 42-44, wherein the infusion device is a preloaded injector or hypodermic needle.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

EXAMPLES

Example 1

Mullerian inhibiting substance (MIS) has long been appreciated for its role in sex differentiation and reproduction, and sensitive ELISAs measuring blood levels are used in fertility clinics around the world as a measure of ovarian reserve (1-5). MIS plays important roles in the development of the gonad and the differentiation of the urogenital duct. In the male fetus, MIS produced by the developing testes causes regression of the Mullerian duct (6). In the female fetus, MIS may play a role in early colonization of the gonad by primordial germ cells (not to be confused with primordial follicles) since mice overexpressing MIS do not have normal follicle assembly and are devoid of germ cells shortly after birth (7), and similarly ex vivo incubation of fetal ovaries with MIS results in inhibition of follicle assembly (8). These data highlight a role of MIS during fetal development which is distinct from its regulatory role of folliculogenesis in the adult.

In the adult, MIS is produced predominantly by the cumulus (less so by the mural) granulosa cells of secondary and early antral follicles (9). The receptor, Misr2 is expressed both in granulosa cells of follicles and in the ovarian surface epithelium (10-14).

It remains unclear how some primordial follicles can stay dormant from birth well into adulthood, and by what mechanism they are selected for activation. However, some studies suggest MIS may be an important gatekeeper of their recruitment. The default state of primordial follicles is skewed towards activation as evidenced by both transgenic mouse models and in vitro ovarian culture experiments. While MIS knockout females were initially fertile (7), young mice were found to contain more pre-antral and small antral follicles, and the window of fertility was shortened. Mice over a year old were nearly completely depleted of primordial follicles, suggesting unregulated recruitment of primordial follicles into the growing pool (15). Similarly, ex vivo cultures of ovarian cortical section, which contain only primordial and primary follicles, undergo recruitment of all primordial follicles in absence of inhibitory signals. When ovarian cortical sections are implanted in chicken embryos, which contain high levels of MIS, primordial follicle recruitment is reduced (16). In contrast, when Misr2 knockout mouse ovaries are implanted in the chicken embryos the primordial follicles are recruited at a similar rate to wild type ovaries implanted in gonadectomized chicks (16). Similarly, ovarian cultures from day 4 rat, a stage at which only primordial follicles are present, 50 ng/ml MIS was sufficient to inhibit the transition of primordial to primary follicles compared to controls, albeit modestly (17).

Until now production of recombinant human MIS (rh-MIS) protein was complicated by the low rates of activating cleavage, low expression, and high rates of unwanted secondary cleavage contributing to a heterogeneous product (18, 19). To address these concerns a new cDNA construct was generated (20), in which the Leader sequence was replaced with that of albumin, and Q425R substitution was introduced in the C-terminal cleavage site, to produce an MIS protein analog (LR-MIS, refer to herein as rhMIS), with increased activating cleavage and secretion. The LR- MIS transgene was also used to produce an optimized AAV9 gene therapy vector compatible with in vivo usage, referred to herein as AAV9-MIS (21).

Unlike other female contraceptive agents which target more mature follicles by interfering with the hypothalamic-pituitary-gonadal axis (through modulation of E2, P4, LH, FSH, and GnRH feedbacks) to inhibit ovulation, MIS acts directly on the first step of folliculogenesis, primordial follicle recruitment, which occurs acyclically from birth (22-24). Controlling this rate-limiting step has important implications to primary ovarian insufficiency (POI), a condition characterized by an early onset of menopause and a catastrophic loss of ovarian reserve (25). One of the significant causes of POI is chemotherapy. Chemotherapy can have lasting effects on female fertility, particularly for childhood cancers (26, 27), and cancers that affect women of reproductive age such as breast cancer (28). In the breast cancer population alone in the United States 26,000 women of reproductive age receive potentially fertility-impairing treatment consisting of regimens of chemotherapy which include alkylating agents, doxorubicin, and taxanes (28). From this growing medical need was borne the new field of "oncofertility", which is devoted to the preservation of fertility in cancer patients (29).

There are two ways in which chemotherapy damages the ovary: direct toxicities to follicles and indirect depletion of primordial follicles from over-recruitment or "follicular burnout" (25). The latter is thought to occur as a consequence of the loss of negative feedback normally provided by growing follicles, which are highly susceptible to chemotherapeutic agents targeting proliferative cells (25).

Ovarian suppression has been proposed as a therapeutic modality for the preservation of the ovarian reserve (30). However, strategies to date have focused on GnRH inhibition, which has had limited success (31-33), likely because gonadotropins only regulate late irreversible stages of follicular maturation rather than the recruitment of primordial follicles which are devoid of gonadotropin receptors (34). Without wishing to be bound by a particular theory, it is hypothesized that by directly inhibiting primordial follicle recruitment, MIS could provide a novel method of contraception and a therapeutic option for oncofertility. MIS is an ideal biologic for this purpose; its safety profile is benign given that its function in adults is predominantly restricted to the gonads, and MIS concentrations in baby boys (50-500 ng/ml) (35), or those found in patients with sex cord stromal tumors (3 µg/ml) (36), exceed those expected to affect folliculogenesis.

Example 2

MIS Administered as Gene Therapy or Purified Recombinant can Induce Superphysiological Blood Concentration Sufficient to Act on its Cognate Receptor (MISR2) in Primordial Follicles of the Ovary.

Figure 1B:
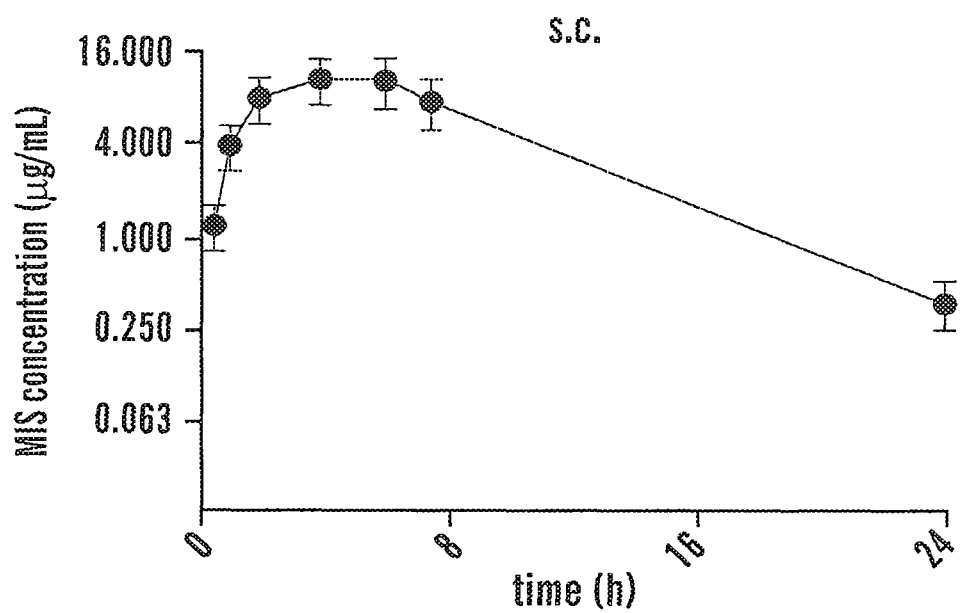
Figure 1C:
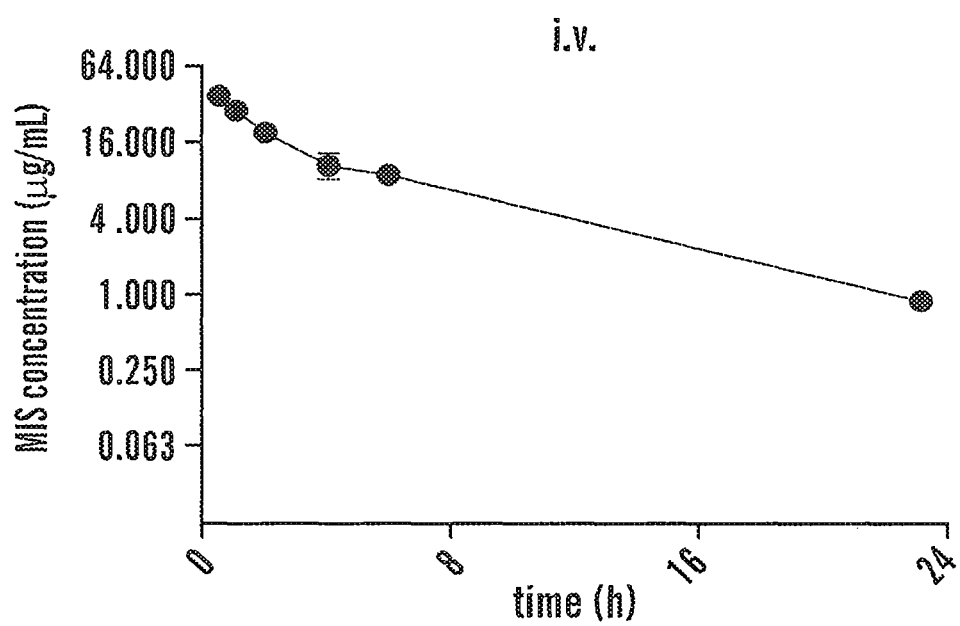

The availability of a biologically active rhMIS protein that can be produced and purified to high yields using CHO cells (20) allowed for higher and longer dosing in-vivo, which had previously been impractical with the poorly cleaved wild-type protein (37), or impossible using commercial C-terminal recombinant MIS protein, which was found to be devoid of activity. For example, incubation of fetal (E14.5) female rat urogenital ridges with 5 µg/ml of rhMIS for 72 h in ex vivo cultures resulted in near complete regression of the Mullerian duct (FIG. 1A—top row), whereas the R&D Systems (Minneapolis, Minn.) c-terminal MIS has no observable activity on the Mullerian duct bioassay (FIG. 1A—bottom row); this assay is the gold standard to test potency and specificity of the hormone (38). The rhMIS protein can be administered subcutaneously (s.c.) (FIG. 1B), intravenously (i.v.) (FIG. 1C), intraperitonealy (i.p.) (FIG. 1E), each resulting in a half-life of approximately 4 h and reaching peak concentrations (Cmax) at 4 hours, 30 mins, and 2 hours respectively. The preferred route of delivery for rhMIS protein was subcutaneously, since its absorption kinetics where most favorable; however, when osmotic pumps were employed, intraperitoneal implantation was found to be optimal, producing steady delivery of up to one week (FIG. 1F). rhMIS activity was remarkably stable, with the material recovered from pumps implanted in mice for one week conserving full biological activity in the rat urogenital ridge bioassay (FIG. 1A—middle row).

Figure 1D:
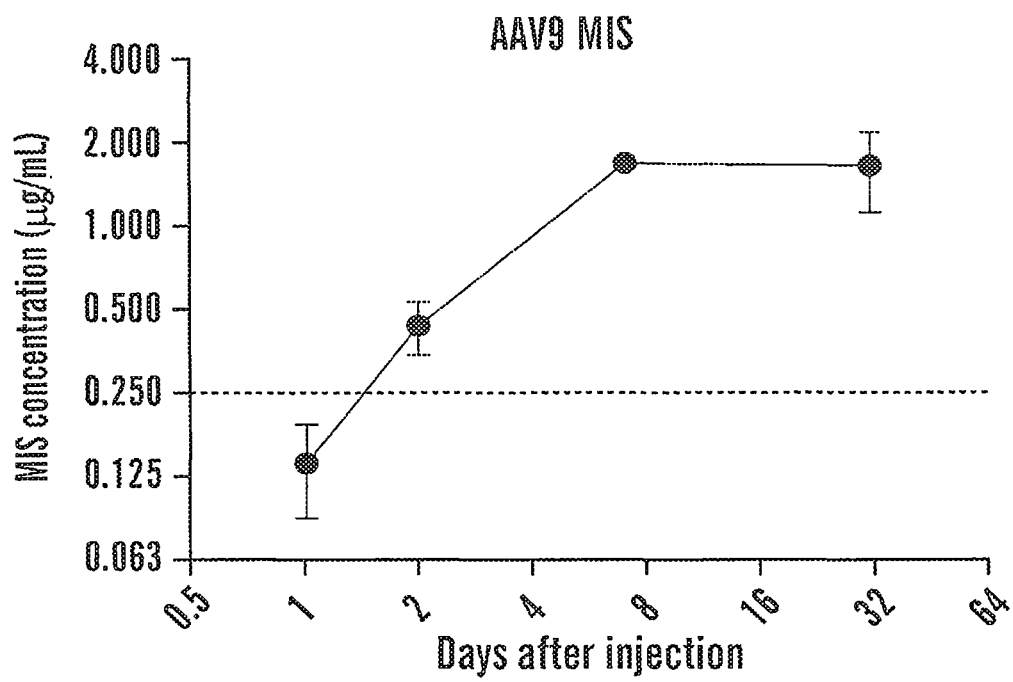
Figure 1E:
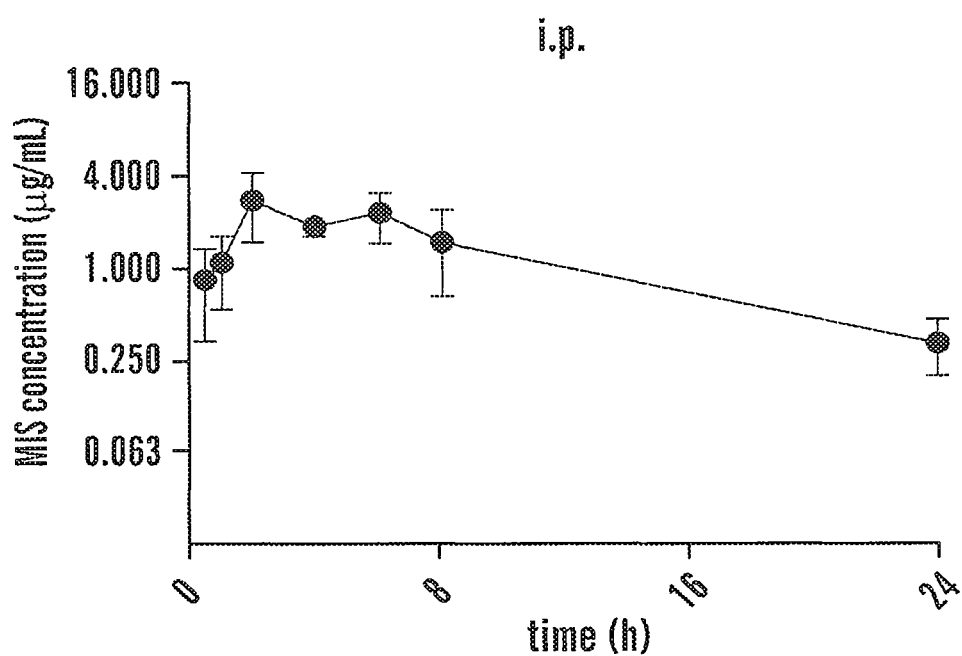

Alternatively, a single intraperitoneal (i.p.) administration of an AAV9 gene therapy vector (at 3E11/mouse) efficiently delivers the rhMIS transgene to the liver, muscles, and pancreas of adult mice (FIG. 1G), which was previously shown to persist for over a year (21). The resulting secreted rhMIS protein can then be found at high concentrations (>250 ng/ml) in the blood as early as 2 days after injection when using an ELISA specific to the human protein (FIG. 1D).

With delivery of MIS optimized, the inhibitory activity of MIS could be evaluated on ovarian primordial follicle recruitment in vivo. To confirm that the MIS receptor, MISR2, is present in the granulosa cells of primordial follicles, ovaries from newborn and adult mice where stained by immunohistochemistry (IHC) (FIGS. 7A and 7B), and immunofluorescence (IF) (FIG. 7C). Data described herein confirmed that granulosa cells of all stages of folliculogenesis expressed Misr2, including primordial follicles (FIG. 7A-7C), with their germ cells identifiable by IF based on their P63+ nucleus and MVH+ cytoplasm (representative examples in inserts).

AAV9 MIS treatment results in reversible ovarian quiescence.

Figure 2C:
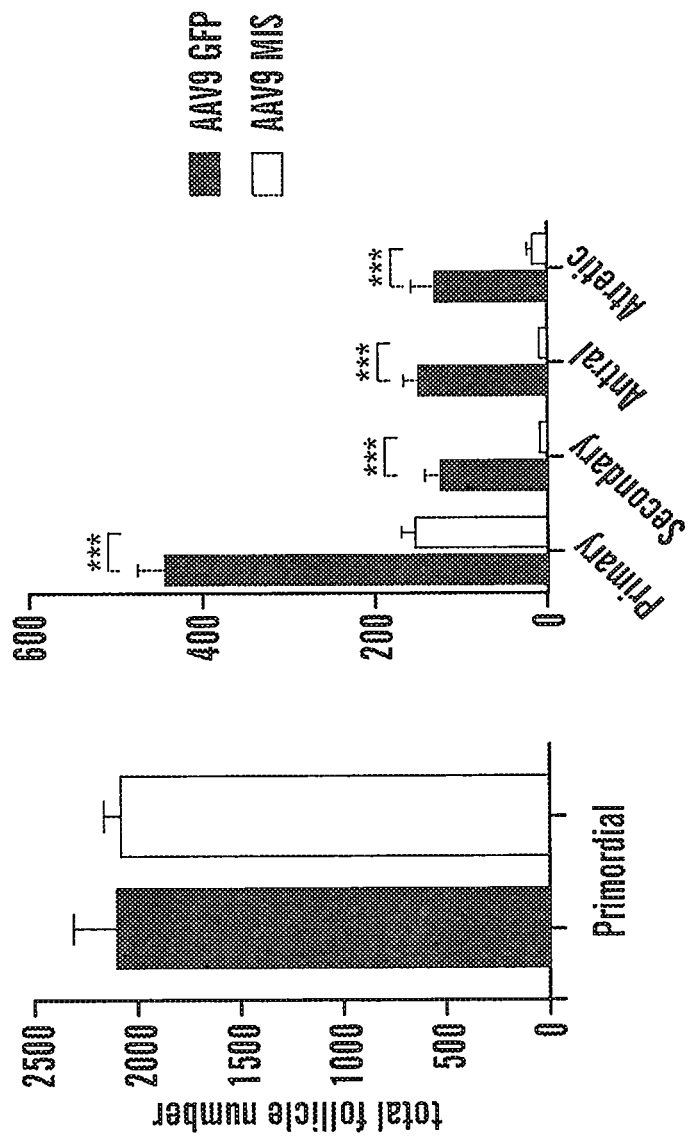

A single i.p. administration of AAV9 MIS vector in adult (7-8 weeks) female nu/nu mice induces viral titer-dependent increase in circulating MIS (FIG. 7D), which can be detected specifically by an ELISA specific to the human protein (2, 20). The circulating level of rhMIS was remarkably stable over the 60 days of the experiment (FIG. 7D); 1E12 particles generated concentrations from 1.5-2.7 µg/ml, 3E11 had 0.8-2 µg/ml, 1E11 had 0.2-0.7 µg/ml, 1E10 had 1-17 ng/ml, while AAV9-GFP control had no detectable human protein. Mice treated with doses of 1E11 viral particles or higher of AAV9 MIS had a marked reduction in growing follicles (FIG. 7E); the middle dose of 3E11 was chosen for subsequent experiments. Ovaries from mice treated with 3E11 particles of AAV9 MIS for 39 days were visibly smaller than control AAV9-GFP ovaries (FIG. 2A) as a consequence of the profound reduction in growing follicles as evidenced in representative middle sections of the ovaries (FIG. 2B). The reduced ovarian size was observed in mice treated for 1-2 months, but not earlier, suggesting gradual depletion. The ovaries from 3 control AAV9-GFP treated and 3 AAV9 MIS females treated for 39 days were sectioned in their entirety and follicle counts were performed (FIG. 2C). The AAV9 MIS ovaries were almost completely devoid of growing follicles, with marked reductions of primary follicles (−65%, p<0.001), secondary follicles (−96%, p<0.001), and antral follicles (−97%, p<0.001) (FIG. 2C). Interestingly, this reduction is unlikely to be attributed to germ cell toxicity or enhanced follicular atresia since primordial follicle counts were unchanged and atretic follicles were actually significantly reduced compared to control (–88%, p<0.001) (FIG. 2C), consistent with a blockade of primordial follicle activation.

Figure 2D:
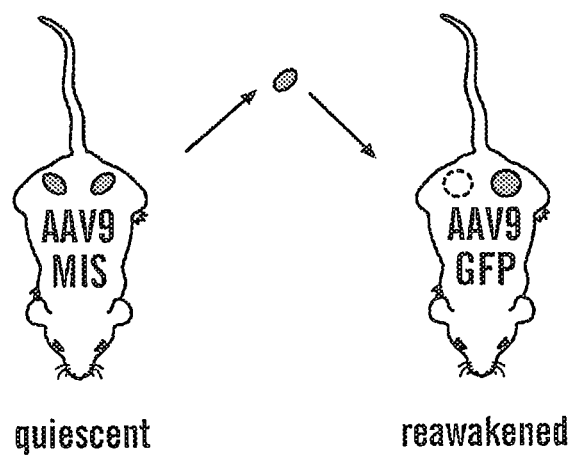
Figure 2D:
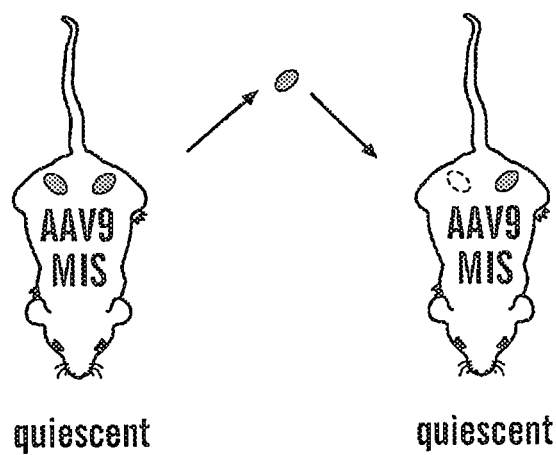
Figure 2E:
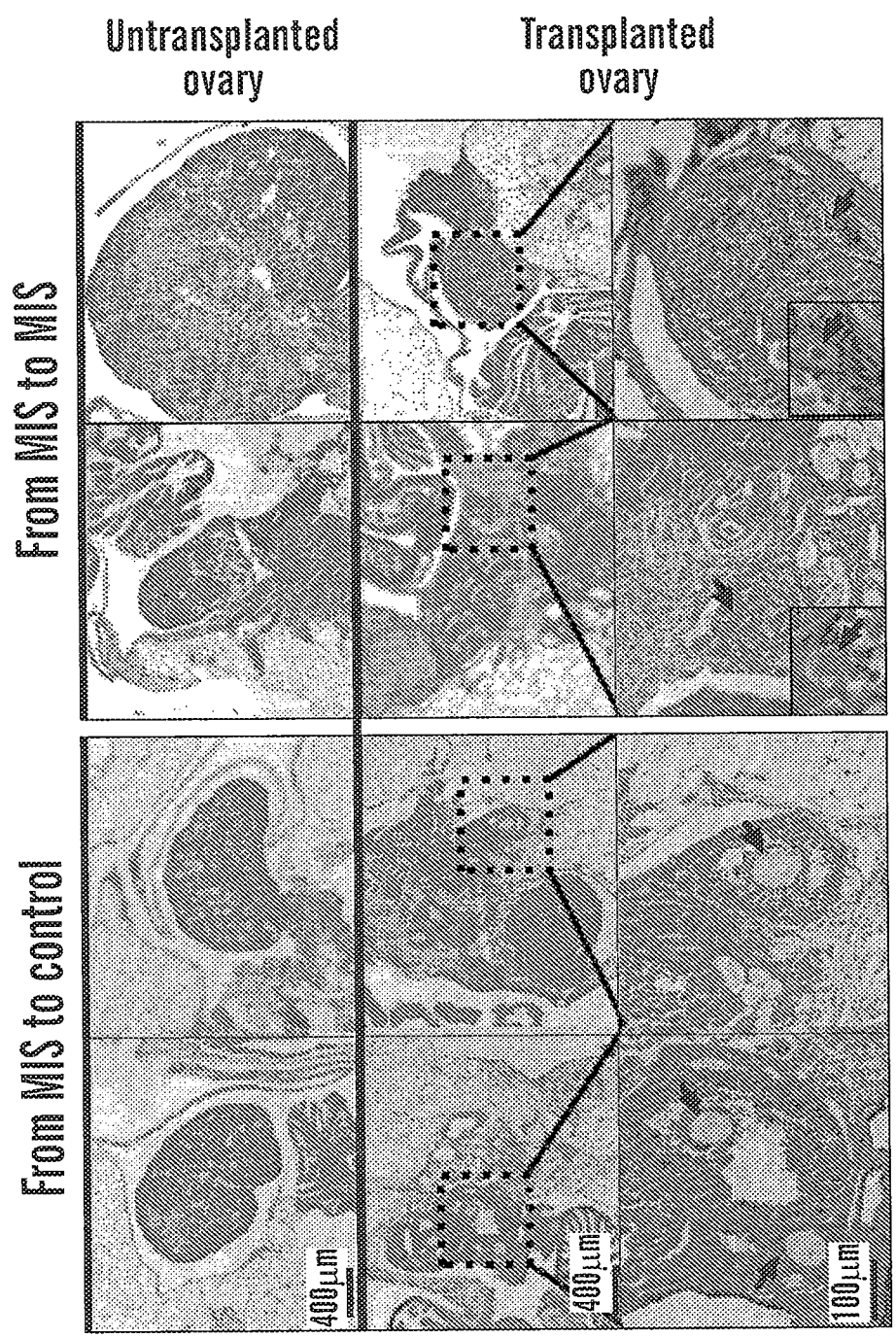

To test if the primordial follicle inhibition is reversible, mice were treated with AAV9 MIS and allowed to deplete their pool of growing follicles for 60 days, after which their ovaries were transplanted orthotopically either into the bursa of AAV9 GFP or AAV9 MIS treated recipient female that was unilaterally gonadectomized (FIG. 2D). Folliculogenesis was "re-awakened", with visible secondary and antral follicles as early as 12 days following transplantation when transplanted in AAV9 GFP recipients that do not have superphysiological levels of MIS, whereas the ovaries remain dormant when reintroduced into another AAV9 MIS treated recipient (FIG. 2E).

Treatment with rhMIS Protein Results in Reversible Ovarian Quiescence.

Figure 3A:
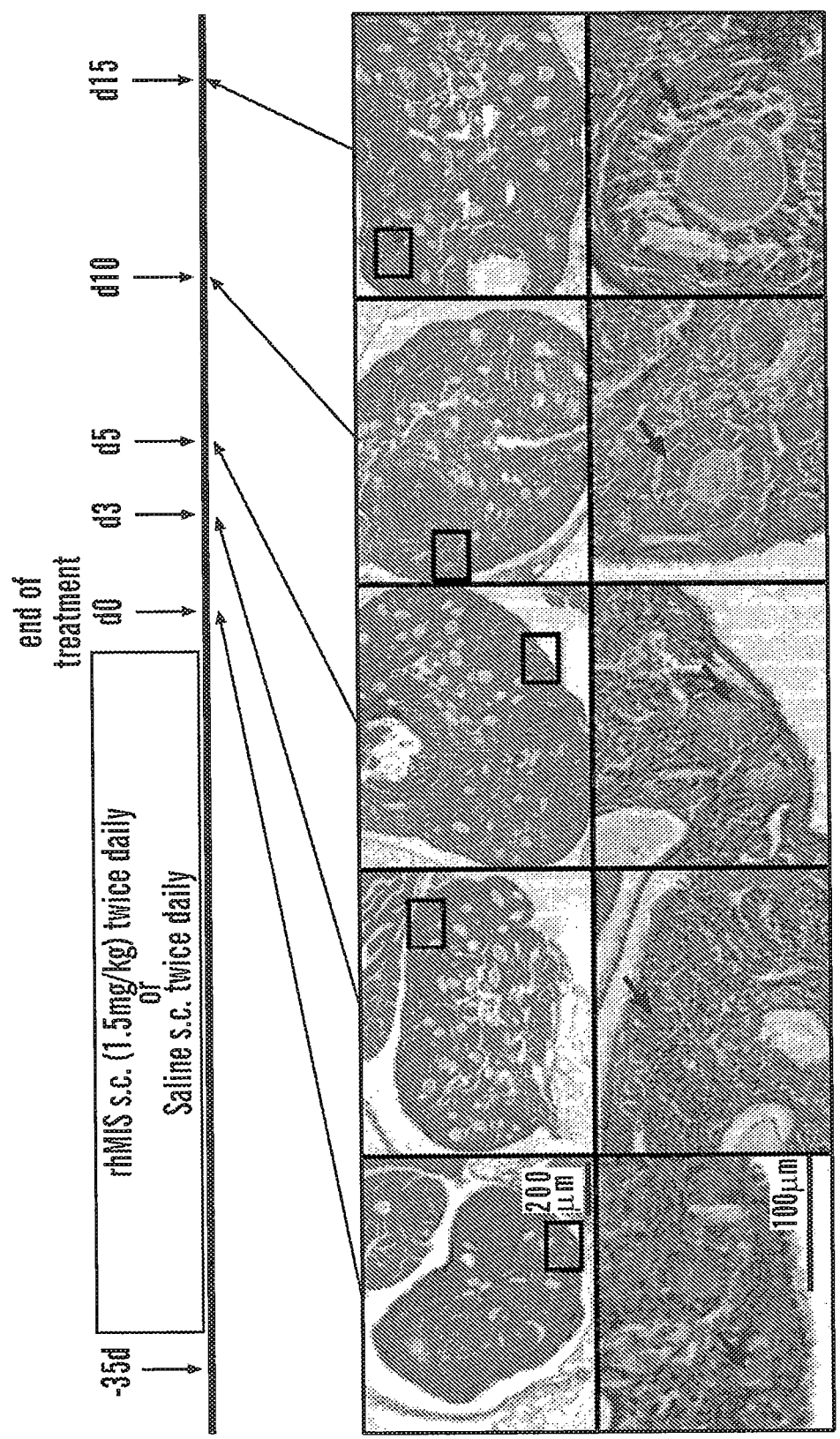
FIGS. 3A-3D present experimental data showing that treatment with rhMIS protein results in reversible ovarian quiescence. Mice were treated twice daily (every 12 h) with a s.c. injection of 1.5 mg/kg of rhMIS for 35 consecutive days, and sacrificed at d0, d3, d5, d10, and d15 post-treatment.
Figure 3B:
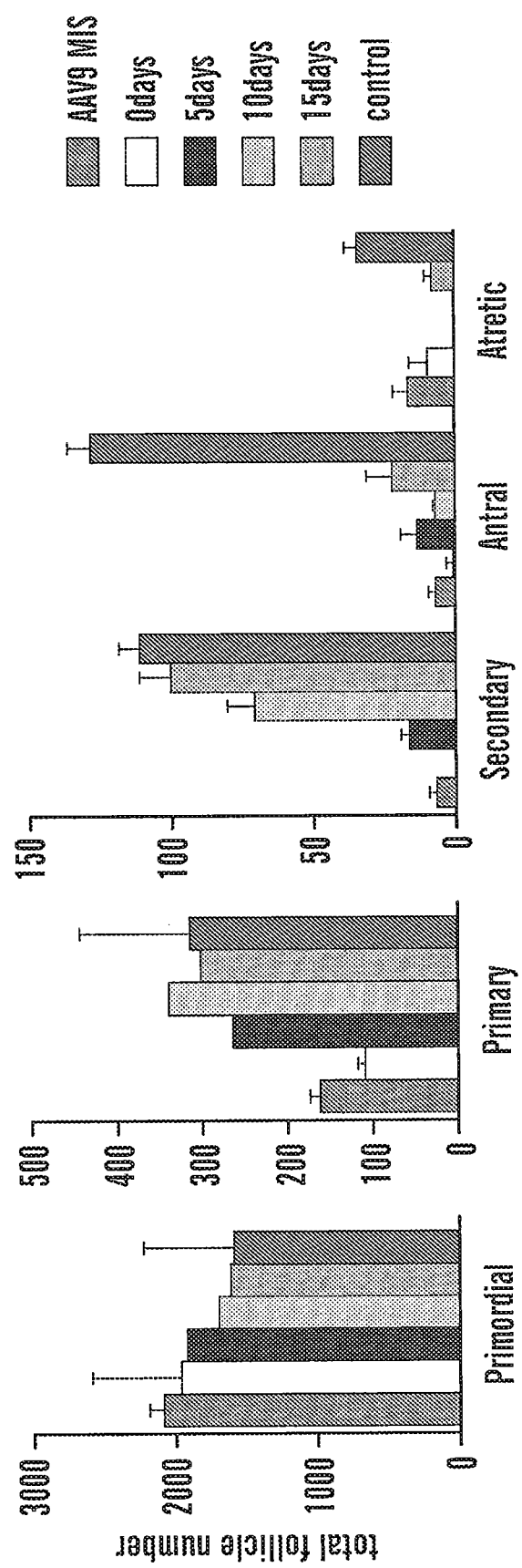
Figures 3C, 3D:
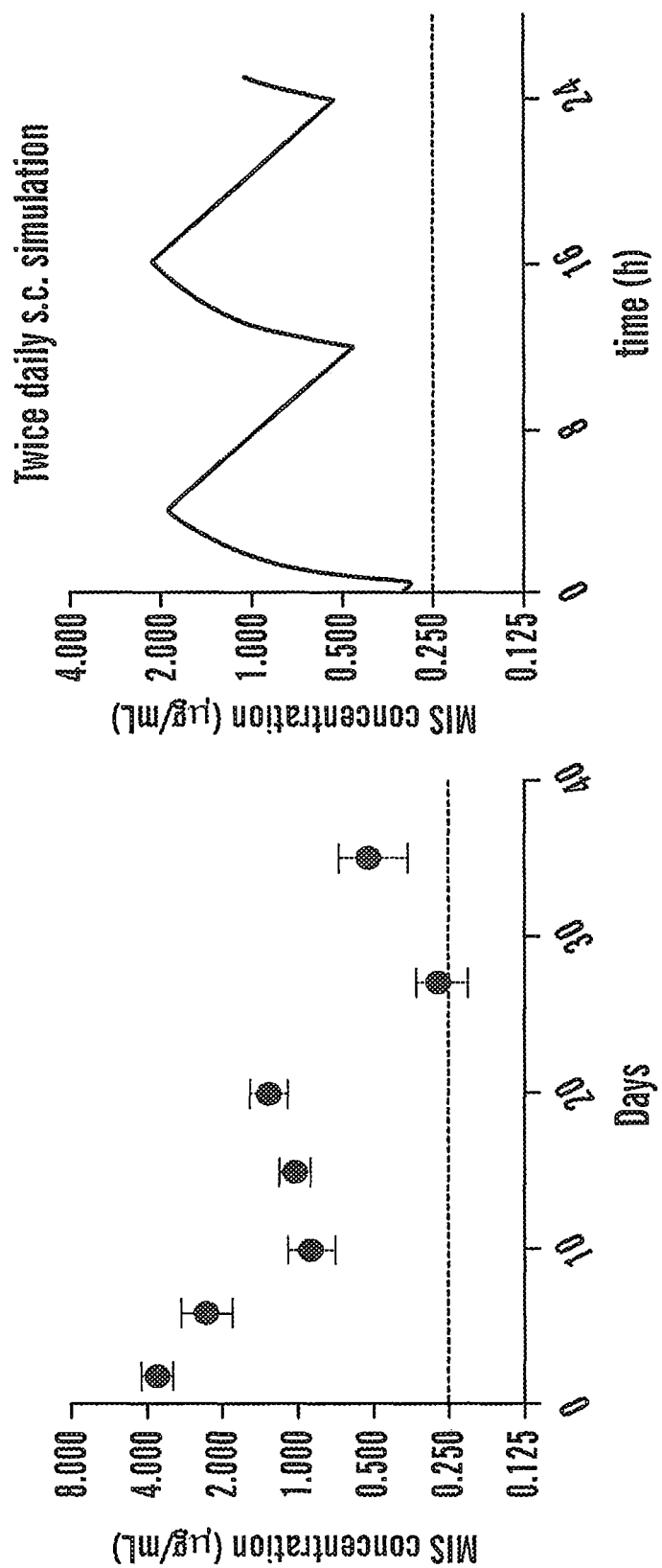
Figure 7D:
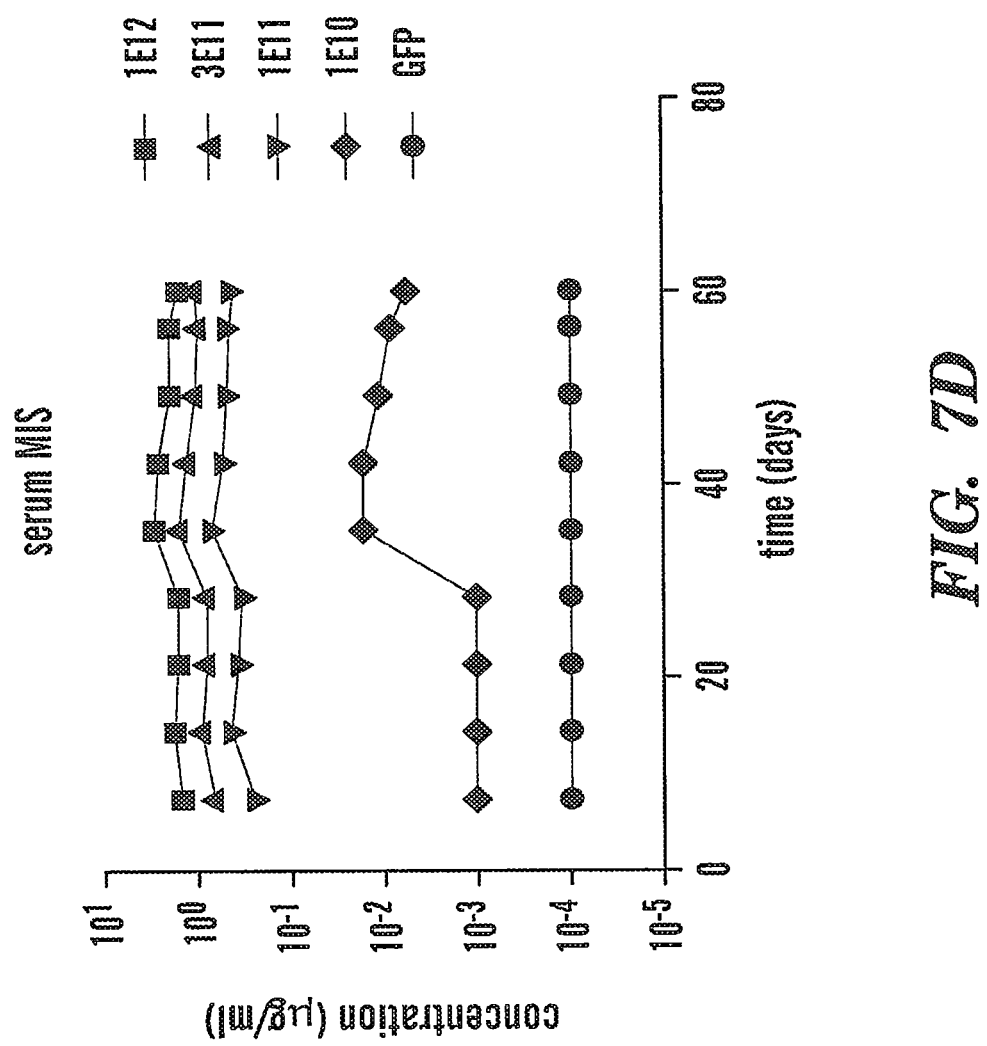
Figure 7E:
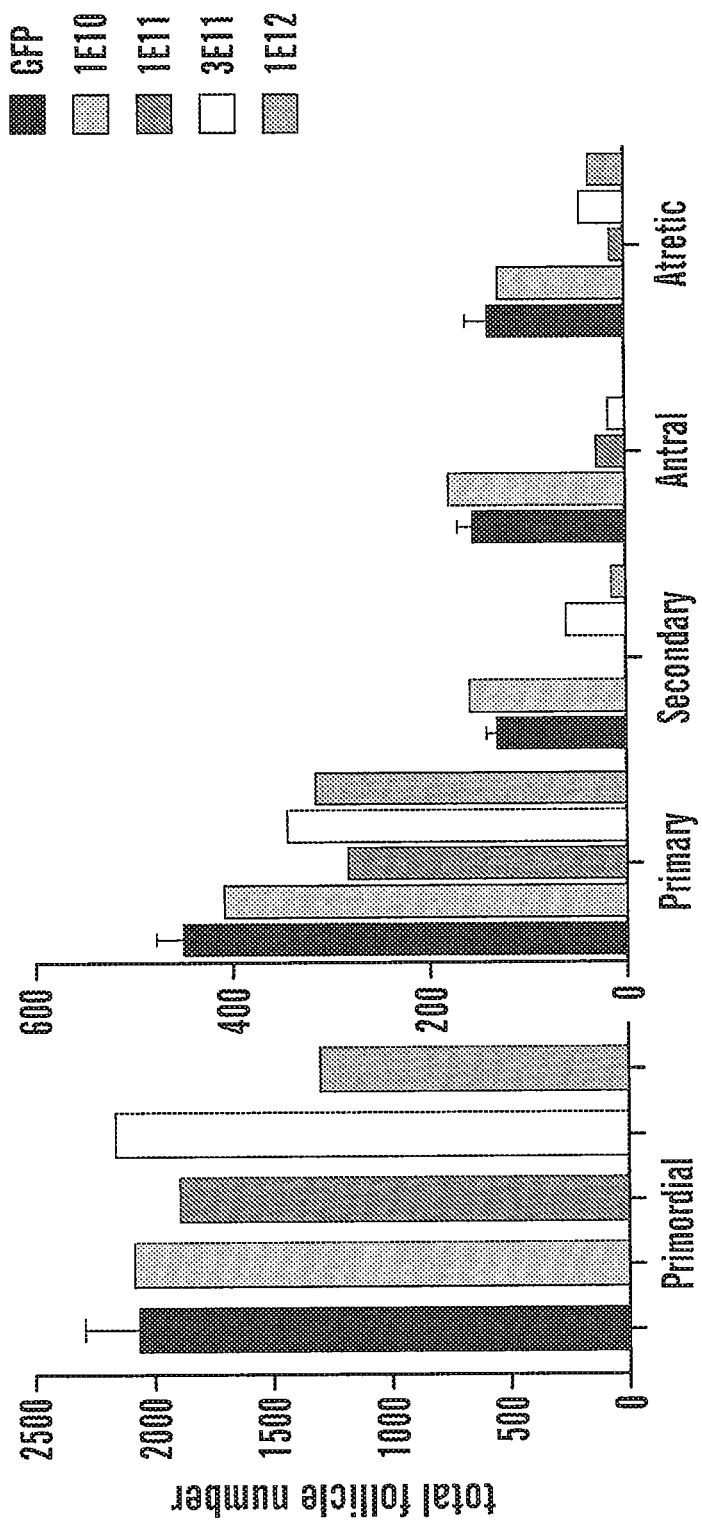
Figure 8:
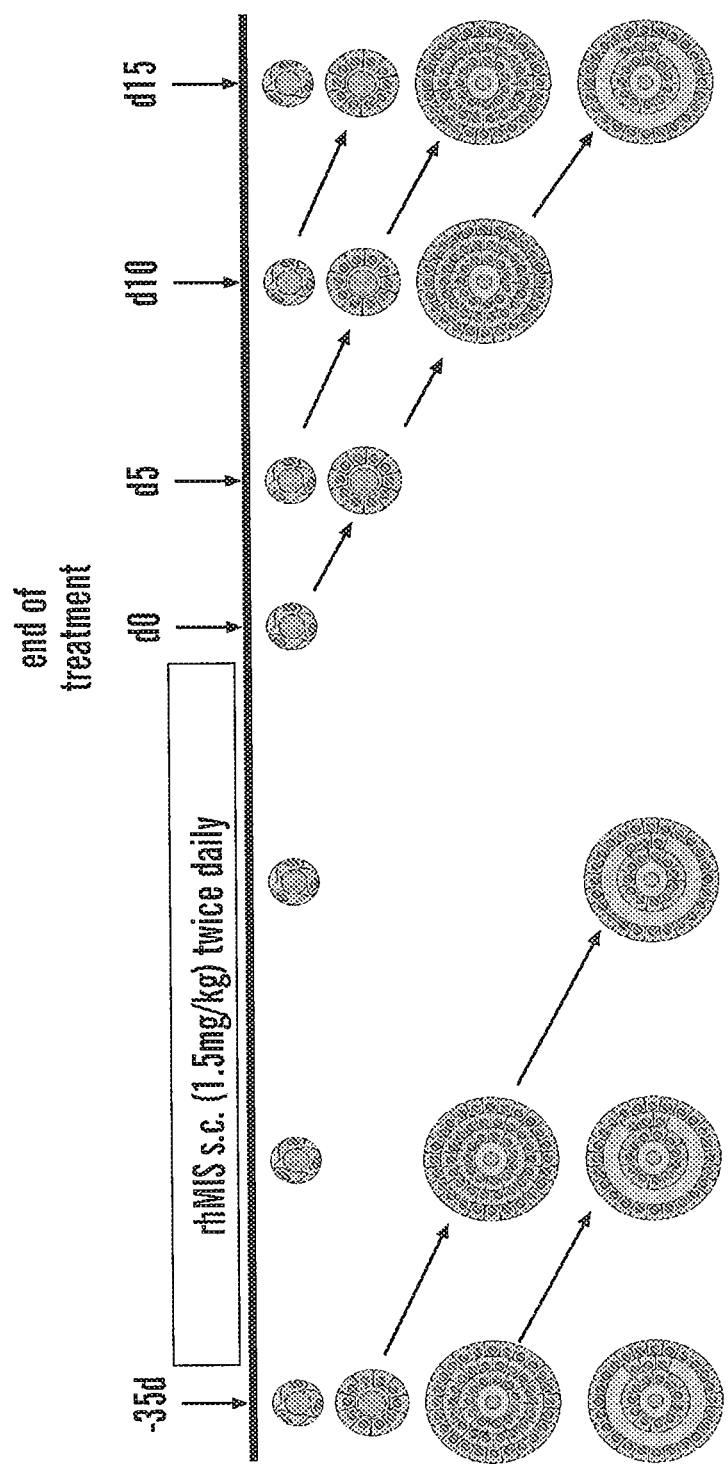
FIG. 8 presents a model of induced reversible follicle quiescence and re-awakening following temporary treatment with MIS protein. Treatment with MIS protein inhibits primordial follicle recruitment, but already recruited primary, secondary and antral follicles are committed to continue their irreversible development and are progressively depleted from the ovary. Once the ovary consists entirely of quiescent primordial follicles, disruption of treatment "re-awakens" some of the quiescent follicles which gradually progress to the primary, secondary and antral stages.

To confirm that inhibition of primordial follicles is not a unique property of gene therapy delivery, and to elucidate the kinetics of ovarian re-awakening, the effect of transient treatment with rhMIS protein was measured. The protein was administered s.c. twice daily (every 12 h), at 1.5 mg/kg (FIG. 3A—tope schematic) which in silico pharmacokinetic modeling predicted would maintain circulating levels of rhMIS above the target level of 0.25 µg/ml (FIG. 3D) (the lower range achieved using 1E11 AAV9 MIS; FIG. 7D). Actual circulating levels of rhMIS measured by ELISA 12 h after injection, representing the trough, were maintained above the target threshold of 0.25 µg/ml, albeit with diminishing concentration during the 35 days of treatment (FIG. 3C). Ovaries from treated mice were markedly reduced in size as evidenced by a representative middle section following 35 days of treatment and contained fewer primary and no secondary or antral follicles. As ovaries were released from quiescence following cessation of treatment with rhMIS protein, folliculogenesis resumed (FIG. 8; model). Ovarian volume increased over 15 days as primary follicles gradually increased from day 3 to day 10, and secondary follicles began to appear day 5 and increased to levels similar to AAV9 saline control by day 15, at which time some antral follicles were observed (FIGS. 3A and 3B).

Gene Therapy with AAV9 MIS as a Vectored Contraceptive.

Figure 4A:
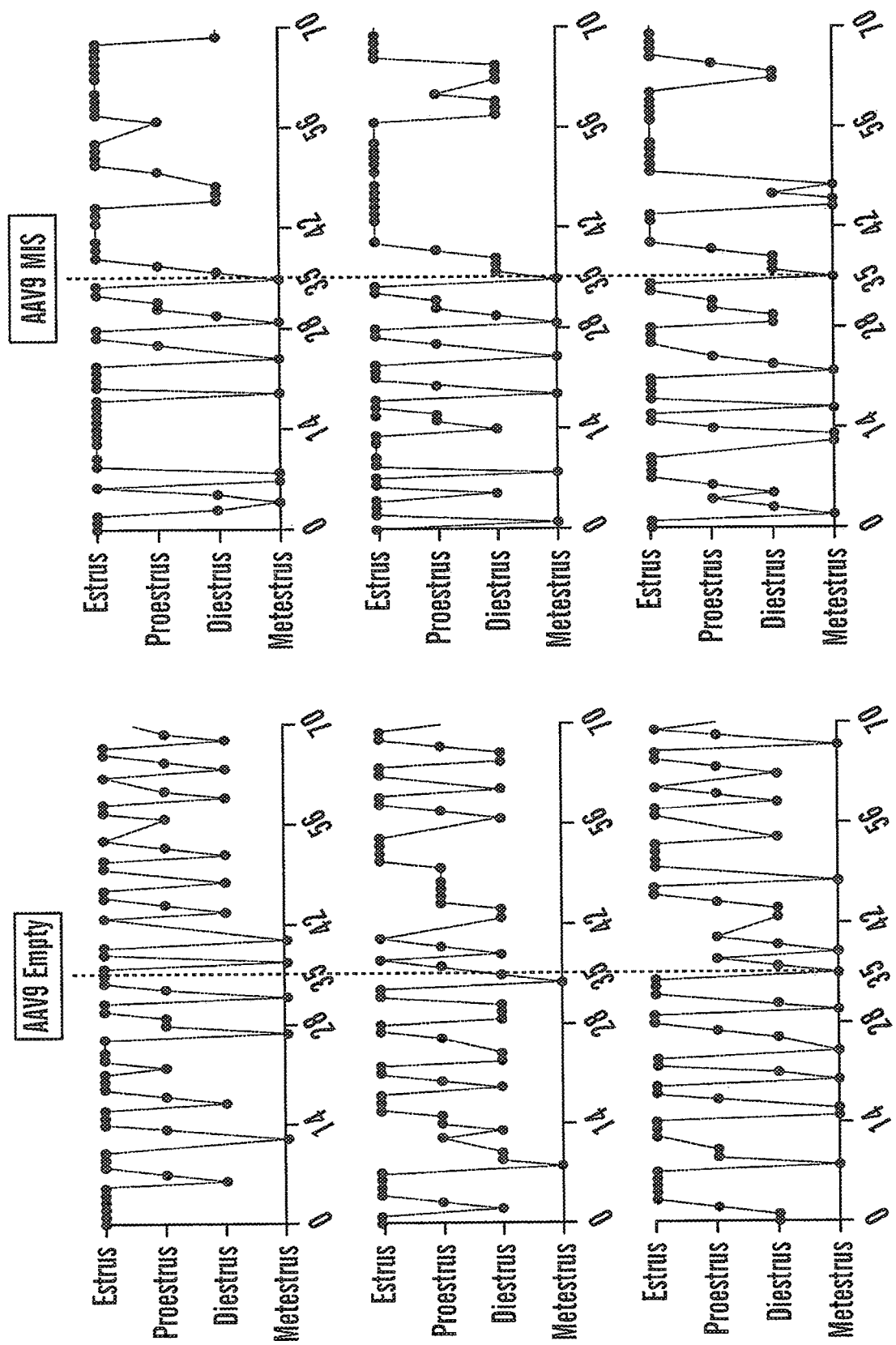
FIGS. 4A-4E present experimental data showing that treatment with AAV9 MIS results in a progressive loss of cycling and fertility and the induction of a hypergonadotropic hypogonadic hormonal profile. Mice were treated with a single injection of 3E11 particles of AAV9 MIS or AAV9 empty vector control.
Figure 4B:
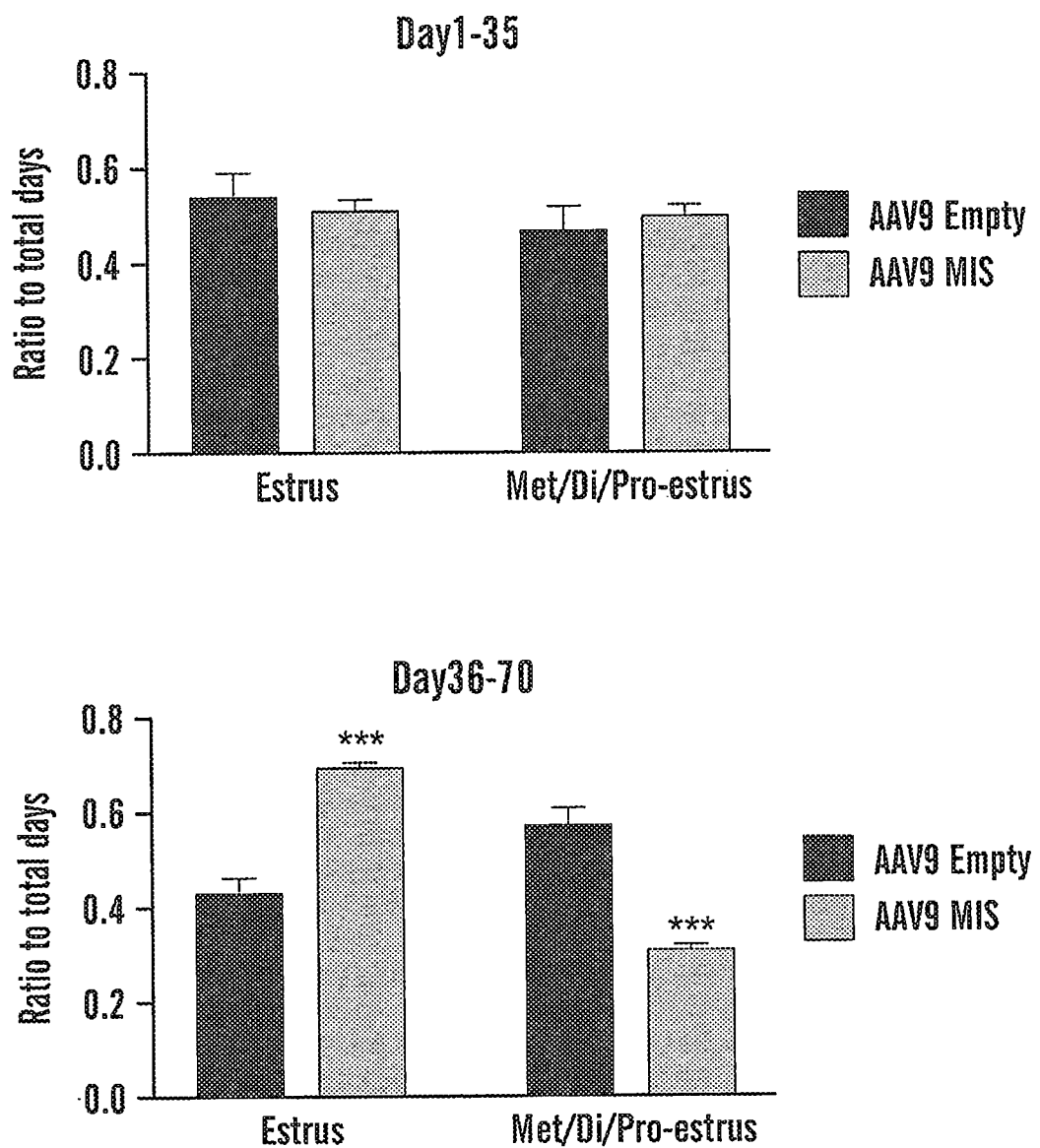
Figure 4C:
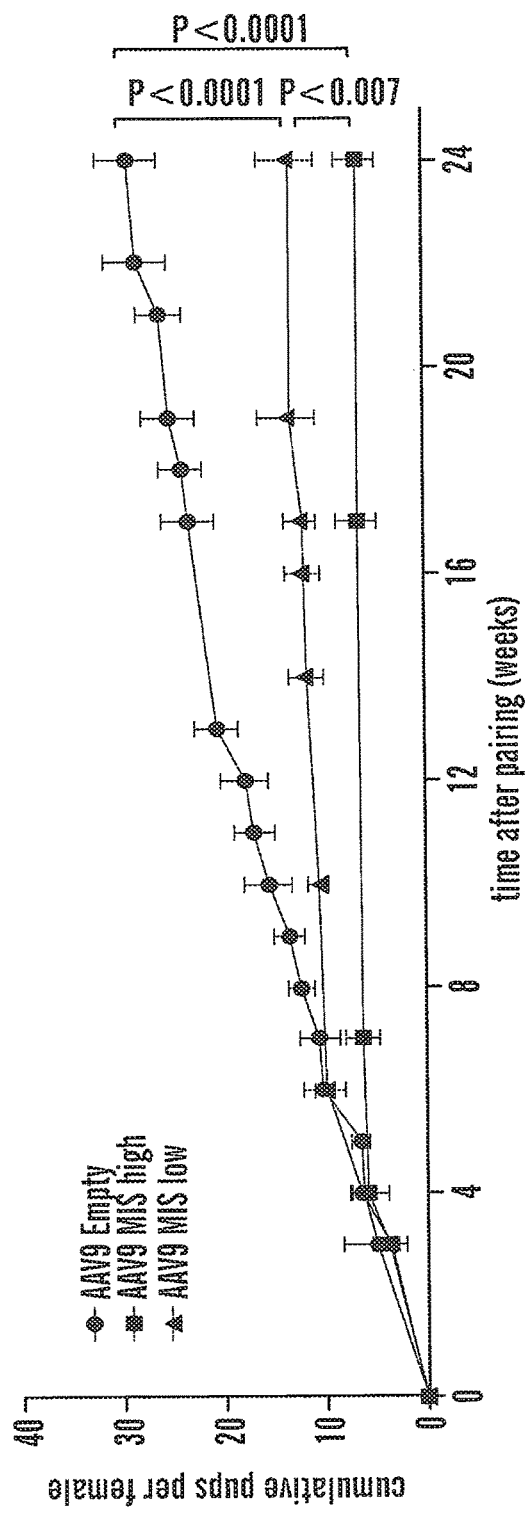
Figure 4D:
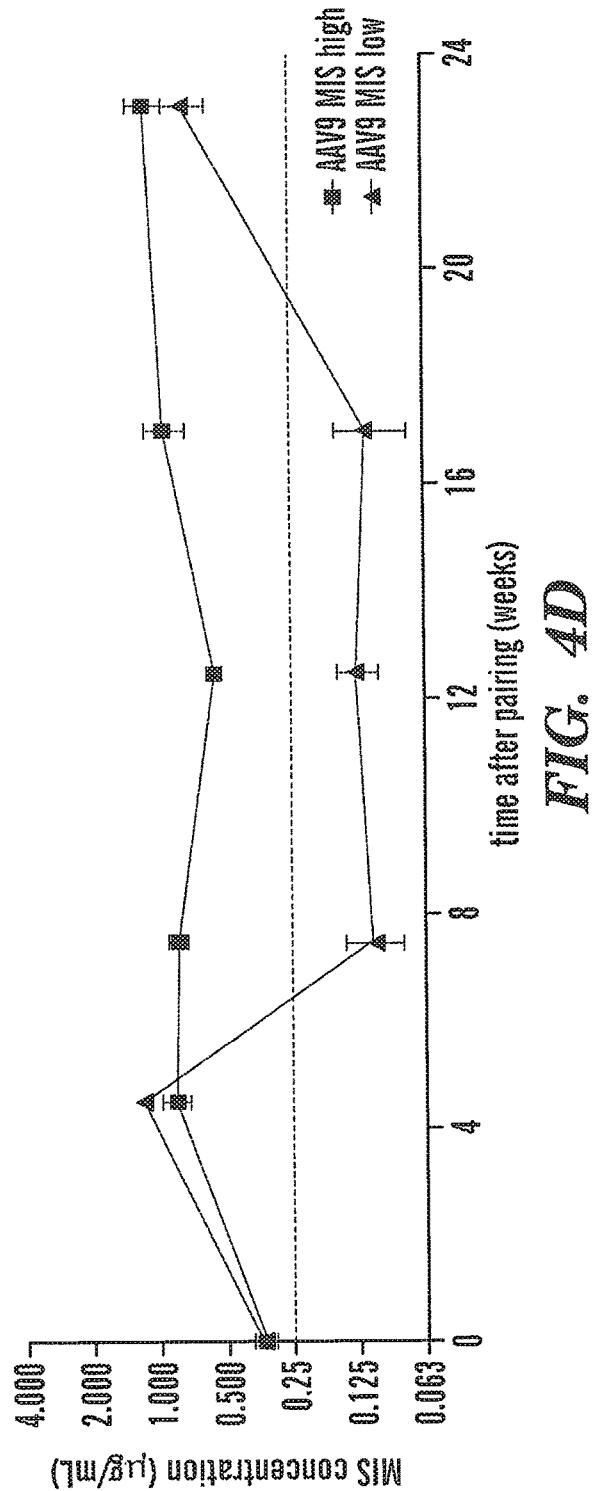
Figure 4E:
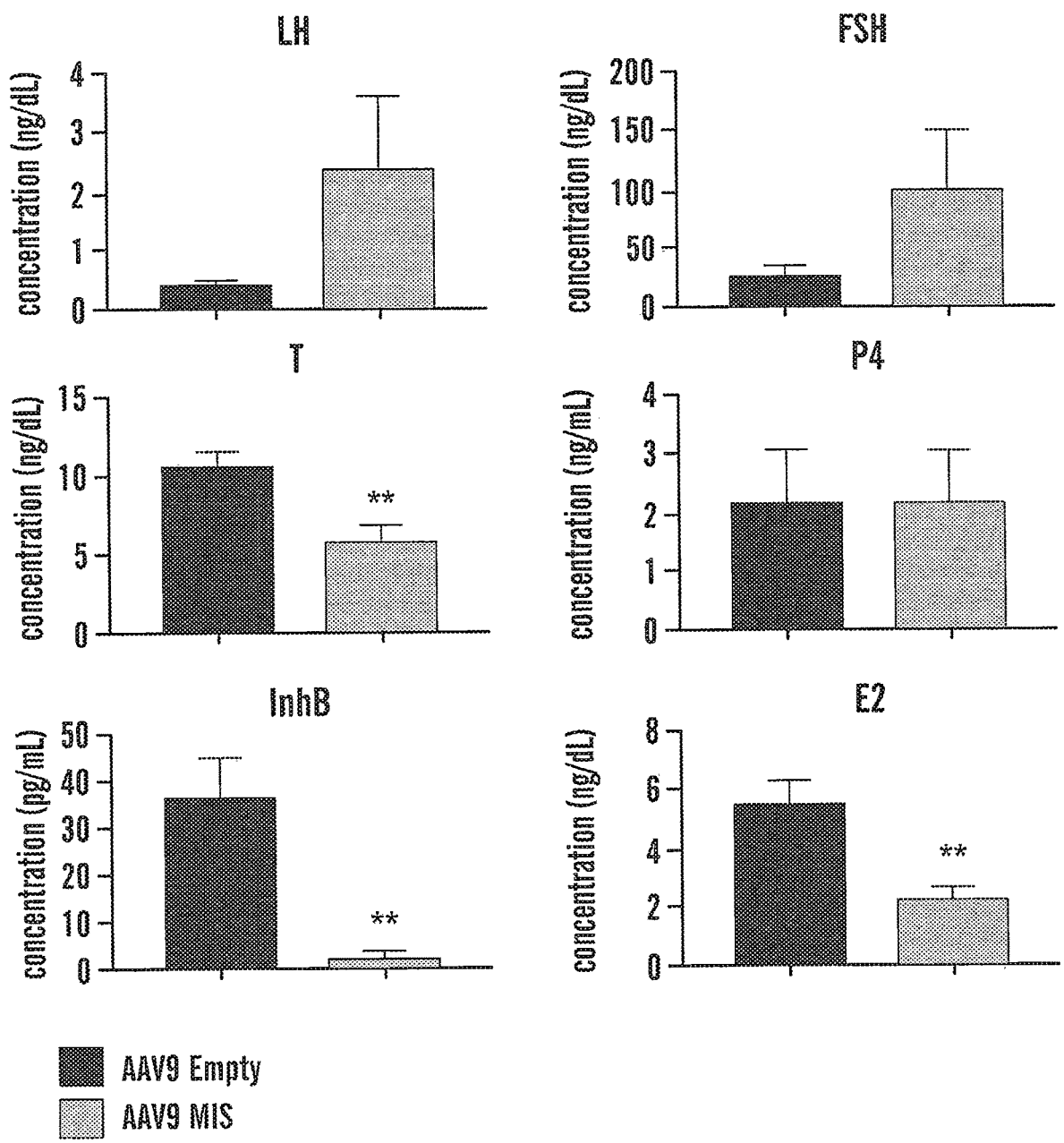
Figure 7F:
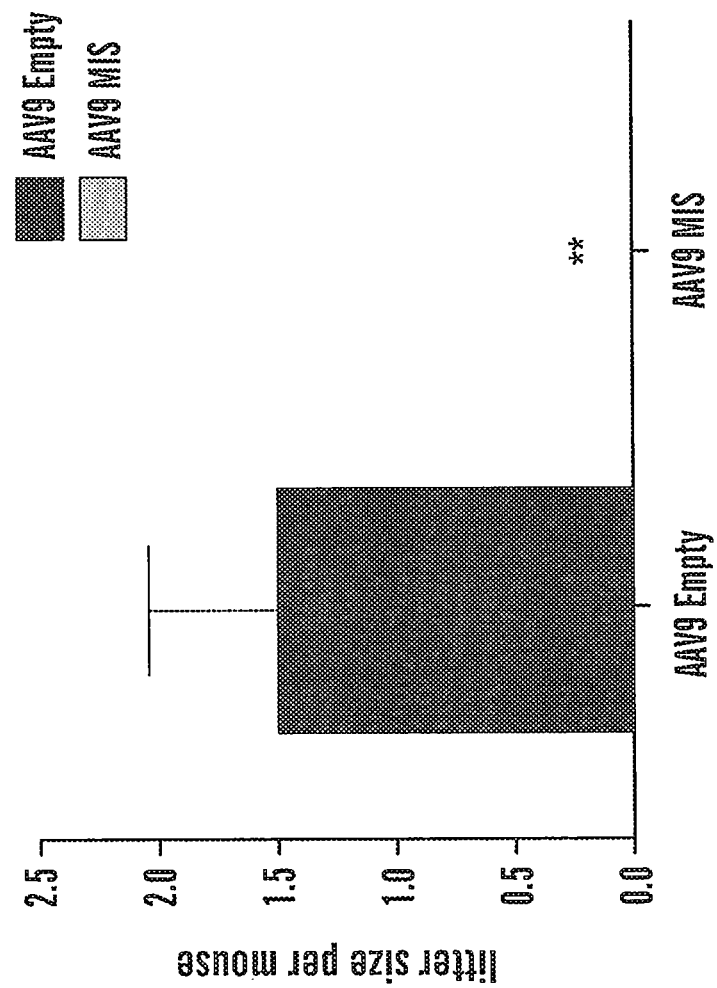

To evaluate the effectiveness of MIS as a contraceptive, the effects of AAV9 MIS treatment on various fertility endpoints were tested. The estrus cycle of AAV9 MIS treated and AAV9 control mice were monitored by daily vaginal swabs. After an initial period of regular cycling in the 35d following injection of the virus, the cycle of AAV9 MIS treated mice first became irregular at week 5 (FIG. 4A), with significantly more time spent in "estrus" from day 36 to 70 (FIG. 4B). The vaginal swabs of acyclic mice resembled the persistent "estrus" cytology typical of ovarian insufficiency, which presents as rare cornified epithelium (39). Female mice treated with AAV9 MIS (N=10) or AAV9 empty control (N=10) were paired with proven male breeders 3 days after AAV9 injection, and were continuously mated for 6 months. Consistent with the gradual depletion of growing follicles, both groups of females had similar litter sizes for their initial litters produced within the first 6 weeks interval immediately following injection (FIG. 4C). Interestingly, litters born during this time to mothers with high levels of MIS had normal sex ratios, normal Mullerian duct development, and no detectable MIS in their blood, indicating that the protein does not cross the placental barrier. For the analysis of fertility, mice which experienced any period of circulating levels of MIS below our target threshold of 0.25 µg/ml as AAV9 MIS "low" (N=4), and those which maintained MIS levels above the 0.25 µg/ml threshold as AAV9 MIS "high" (N=6) were grouped (FIG. 4D). AAV9 MIS "high" mice became completely infertile after 6 weeks, whereas AAV9 MIS "low" experienced reduced fertility with a few small litters during the course of mating experiment (FIG. 4C). Cumulative litters per female were significantly reduced both in the "high" (p<0.0001) and "low" (p<0.0001) groups (FIG. 4C). When the same females were mated for one month at 1 year of age, control females still had some residual fertility with on average 1 pup per female, whereas all the treated females remained infertile (FIG. 7). Following the 6 month mating study, blood samples were taken from both treated and control female mice to assess reproductive hormone levels. There was a significant reduction in inhibin B (INHB), 17β-estradiol (E2), and its precursor testosterone (T) in AAV9 MIS treated mice compared to controls; however, progesterone levels (P4) were unaffected (FIG. 4E). As expected, the pituitary responded with elevated gonadotropins, with trends for greater FSH and LH levels in AAV9 MIS treated females compared to controls (FIG. 4E) (40).

MIS Treatment Protects the Ovarian Reserve from Follicular Burnout Induced by Chemotherapy.

Figure 5A:
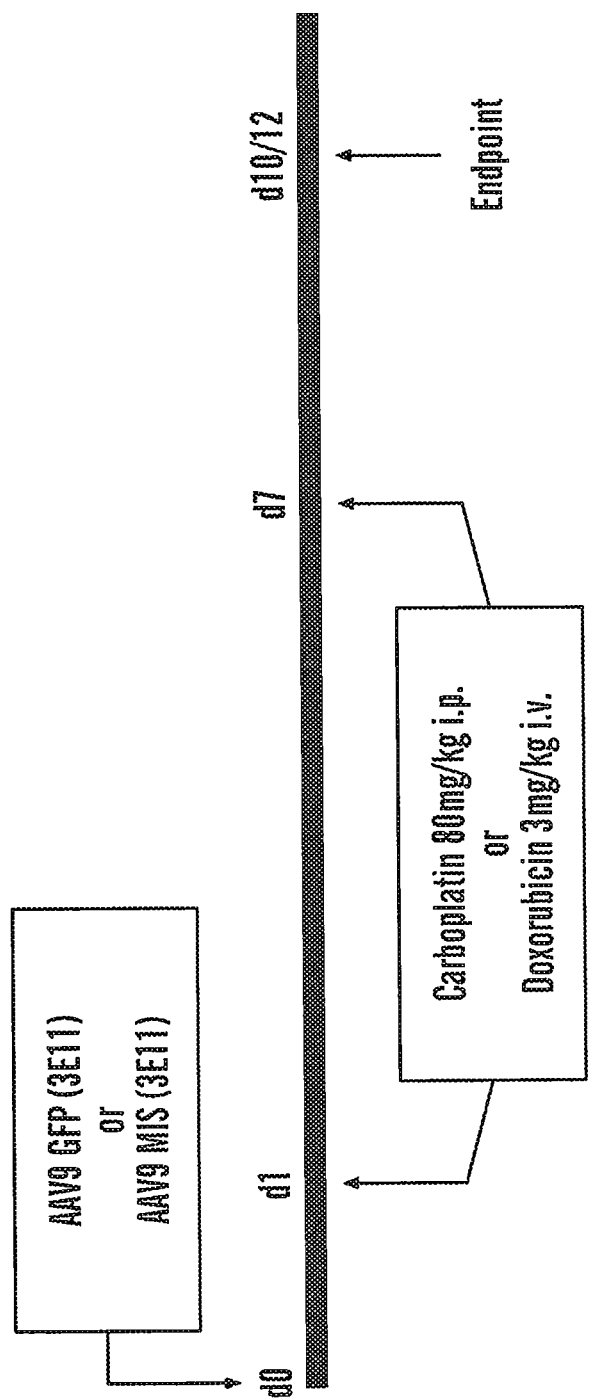
Figure 5D:
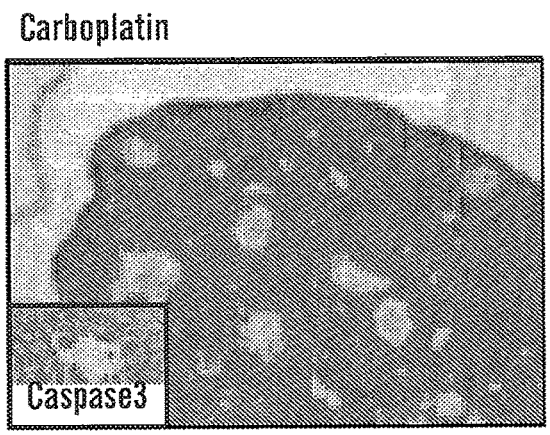

To evaluate ovarian suppression by MIS as a protective therapy against chemotherapy-induced follicular burnout, both the AAV9 MIS gene therapy and the rhMIS protein approaches were tested in mouse models of chemotherapy. For this purpose AAV9 MIS or AAV9 GFP was administered to adult (7-8 weeks) tumor bearing Nu/Nu mice, and a day later began weekly doses of Carboplatin (CBP) (N=10) at 80 mg/kg i.p. or Doxorubicin (DOX) (N=9) at 3 mg/kg i.v., until the mice were sacrificed for tumor related endpoints (volume >1 cm$^3$) at day 10 and 12 respectively (FIG. 5A). Ovaries were retrieved, serially sectioned, and follicle counts performed. Significantly higher ovarian reserves were observed in mice co-treated with AAV9 MIS compared to control AAV9 GFP, with primordial follicle counts 2.2 fold higher (p<0.001) in CBP treated mice, and 1.8 fold higher (p<0.01) in the DOX treated mice (FIGS. 5B and 5C). No differences were observed in growing follicle counts; however, an abundance of growing follicles with extensive granulosa cell apoptosis was noticed, as evidenced by pycnotic hematoxilyn staining and cleaved caspase-3 staining by IHC in all groups (FIG. 5D). Cleaved caspase-3 positive primordial follicles were not found.

Figure 1F:
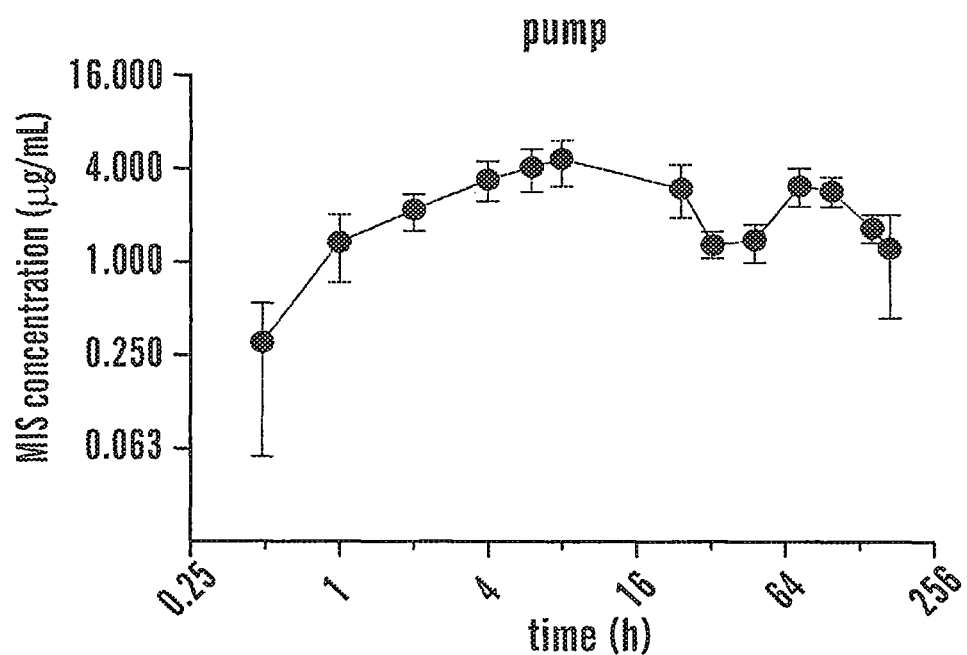
Figure 1G:
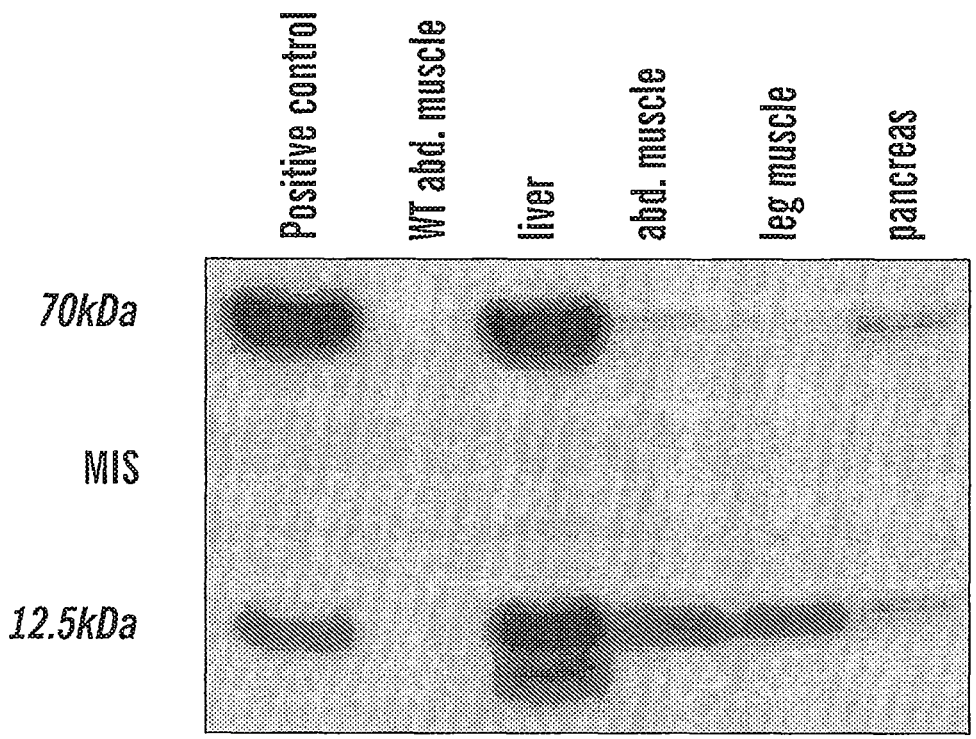
Figure 5E:
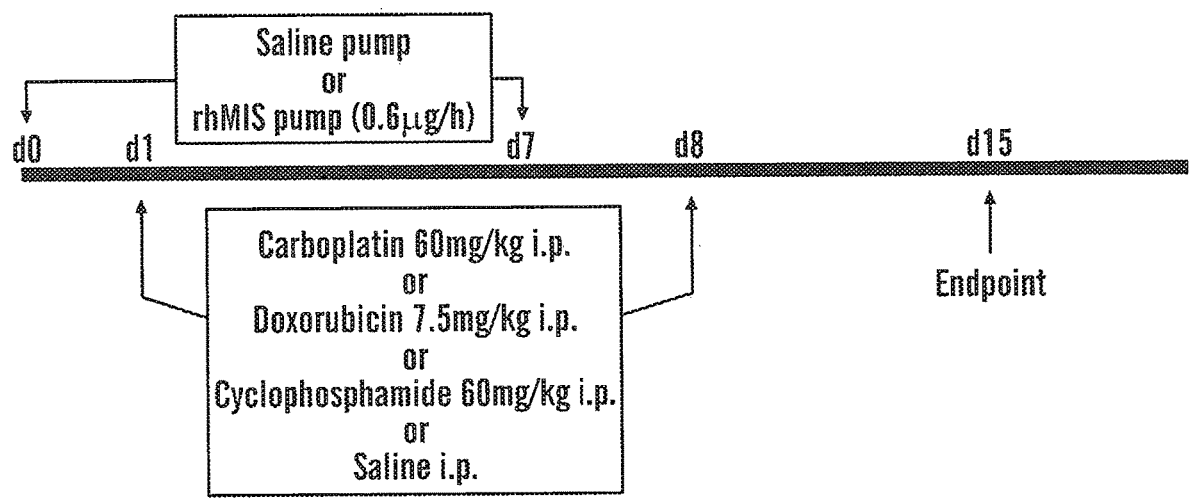
Figure 5F:
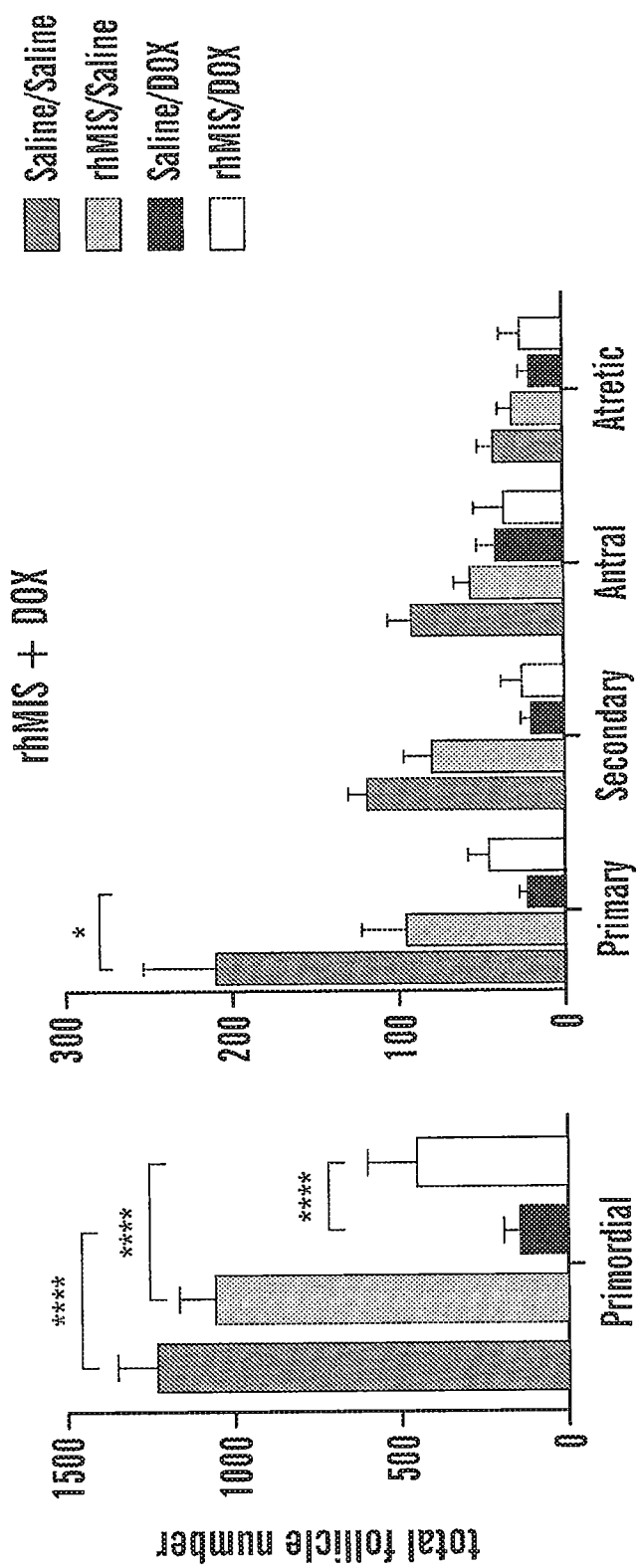
Figure 5G:
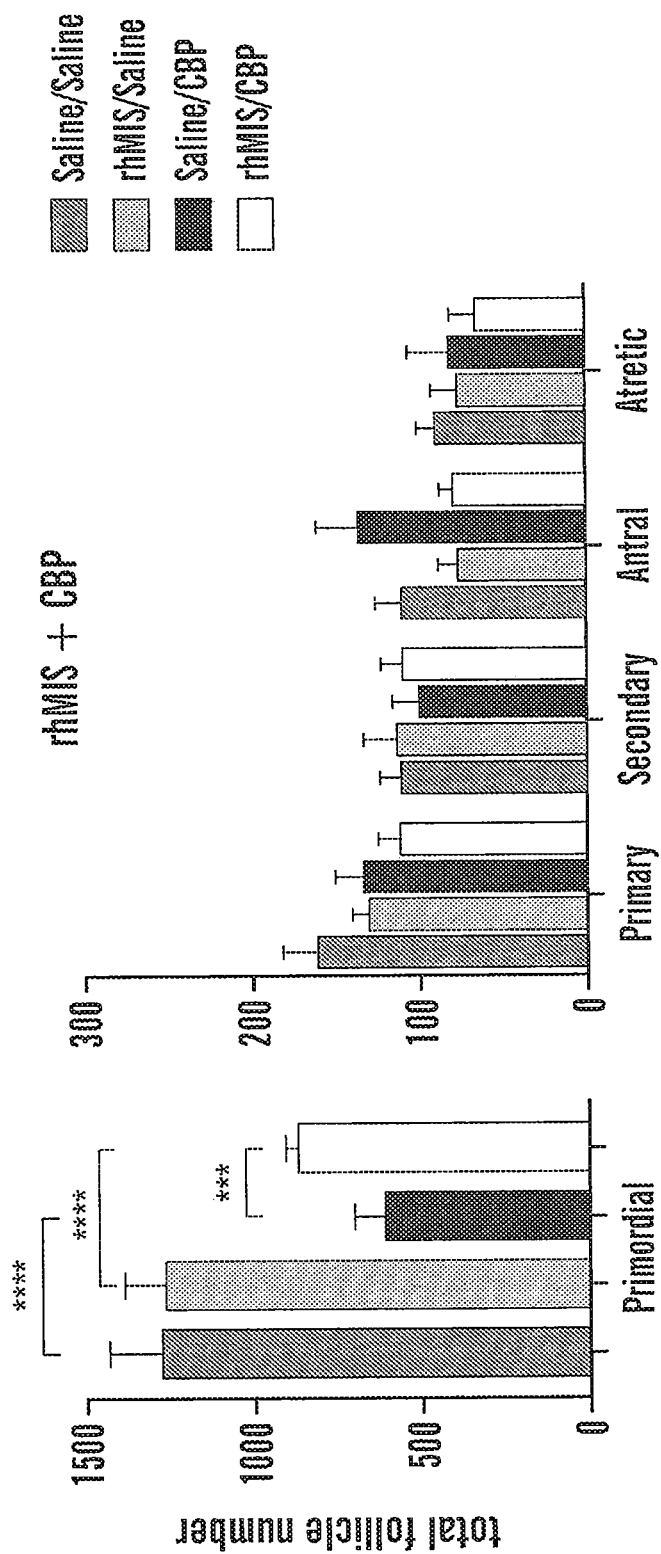
Figure 5H:
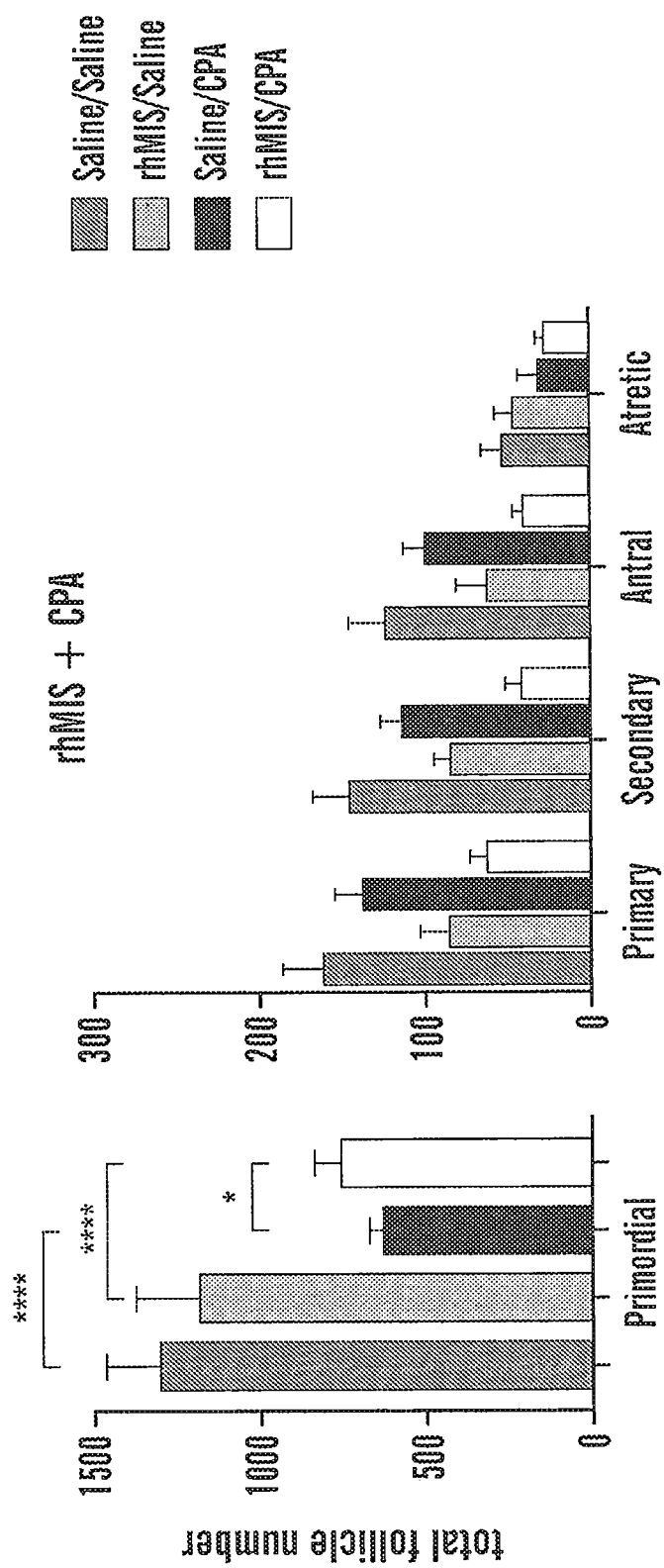

To test the efficacy of rhMIS protein for preservation of ovarian reserve, the use of osmotic pumps implanted i.p. in C57BL/6N female mice was elected, which allows for very precise delivery of MIS (FIG. 1F). In this model osmotic pumps loaded with 100 µl of a 1200 µg/ml solution of rhMIS diluted in saline, or saline loaded control pumps were implanted; the pumps were replaced every 7 or 5 days (FIG. 5E). The day after implantation of the pump, mice began their weekly treatment of i.p. chemotherapy or saline control, using doses of 60 mg/kg for CBP, 7.5 mg/kg for DOX, and 60 mg/kg for CPA (FIG. 5E). After 2 weeks of chemotherapy, mice were sacrificed, ovaries were retrieved, serially sectioned, and follicle counts performed. significantly higher ovarian reserves were observed in mice implanted with rhMIS-eluting pumps prior to receiving chemotherapy compared to controls with saline pumps receiving the same chemotherapy. Primordial follicle counts were 1.4 fold higher (p<0.0001) in CBP treated mice, 2.9 fold higher (p<0.001) in DOX treated mice, and 1.2 fold higher (p<0.05) in CPA mice (FIGS. 5F-5H). Treatment with hrMIS alone did not significantly affect either primordial follicles or growing follicles within this short timespan; however, there was a trend towards lower numbers of growing follicles compared to saline only controls (FIGS. 5F-5H).

Example 3

The MIS receptor, Misr2 has long been known to be expressed by ovarian surface epithelium and granulosa cells of the ovary (10), and its promoter is often used in the generation of conditional transgenic mice for these cell types (14). Results described herein confirm that Misr2 expression during folliculogenesis may begin as early as the primordial stage, and persist from birth to the depletion of those follicles (FIG. 1). Reports of the effect of MIS on follicles have been mixed, with some studies suggesting an activating effect (41, 42) while others imply an inhibitory effect directly on the primordial follicles (17, 43), or indirectly on gonadotropins (44, 45), or even inhibition of meiosis (46). In past studies, the described inhibitory effect size on primordial follicles in vivo and in vitro have been perceived as relatively modest, owing to the difficulties in supplying high levels of the protein. Due to the rhMIS analog LR-MIS (20) and the use of gene therapy vectors, e.g., such as AAV9 (21), the effects of superphysiological levels of MIS on the ovaries of adult mice have been tested for the first time. In contrast to previous studies, MIS was found to be capable of inducing a complete shutdown of folliculogenesis. Follicle counts suggest a specific inhibition of primordial follicle activation without inhibition of other stages or increases in rate of atresia (FIG. 2C right-most column pair). Consistent with this hypothesis, the MIS-induced ovarian quiescence takes approximately 5 weeks to manifest itself as seen by cycling and mating studies (FIGS. 4A and 4C), suggesting already growing follicles complete their irreversible development and are gradually depleted from the ovary (FIG. 8—model). Furthermore, the fact that the fertility of MIS-treated mice during the first 5 weeks of treatment is not different from controls suggests that any positive or negative effect of MIS on other stages of folliculogenesis or gonadotropins/steroids levels is biologically insignificant to fertility. Furthermore, many studies employing commercial c-terminal MIS protein in the context of fertility should be interpreted with caution given the lack of specific biological activity of that peptide in the rat fetal urogenital ridge bioassay (FIG. 1A).

Remarkably, the inhibition of primordial follicle activation by MIS was found to be reversible in ovarian transplantation from AAV9 treated animals, or in intermittent protein treatment experiments (FIGS. 2E, 3A, and 3B). The re-awakening of folliculogenesis was rapid (FIG. 8—model), with the number of secondary follicles gradually recovering within the normal range within 15 days of cessation of treatment with the rhMIS protein (FIG. 3B).

Given the near complete block of folliculogenesis, and the resulting infertility of treated mice (FIG. 4C), MIS or agonists targeting its pathway may represent a novel hormonal contraceptive approach. Unlike current hormonal contraceptive which disrupt the hypothalamus/pituitary/gonadal axis and act on already committed secondary and antral follicles, MIS inhibits the first step of activation of the dormant primordial follicle, thus sparing the germ cell. It has not escaped our notice that the chronic use of a contraceptive method sparing germ cells suggests extension of the reproductive lifespan of its user, however matters of oocyte quality associated with aging remain to be resolved. More practically, vectored contraceptives using MIS may be very useful in the veterinary setting where single injection permanent contraceptives could be used for animal population control, since AAVs are not replication competent, and have a history of safe use for that purpose (47).

Figure 6:
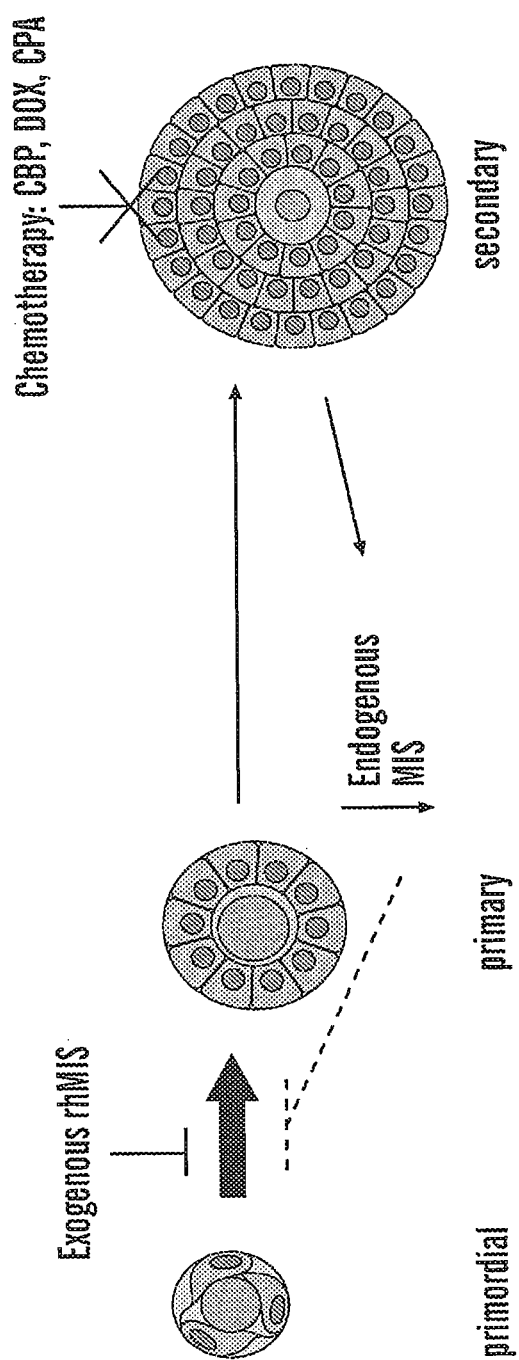
FIG. 6 presents a schematic model of hormone replacement treatment with exogenous MIS to protect the ovarian reserve from the follicular burnout induced by chemotherapy. Chemotherapeutic agents (CBP, DOX, CPA) toxic to dividing cells of growing follicles disrupt the negative feedback such follicle normally provide on primordial follicle recruitment, leading to a self-amplifying follicular "burnout". By restoring negative feedback with exogenous MIS, primordial follicle activation could be inhibited, thus lessening the depletion of the ovarian reserve.

This unique mechanism of action presents some therapeutic opportunities not afforded by current hormonal contraceptives. Limiting primordial follicle activation could lessen the premature depletion of the ovarian reserve observed in cases of primary ovarian insufficiency (POI) induced by environmental, iatrogenic, or genetic causes. This is particularly true of cases where POI may be exacerbated by follicular burnout, in which specific toxicities to growing follicles causes over-recruitment of primordial follicles (25). Without wishing to be bound by theory, it is hypothesized that the mechanism of follicular burnout may be due to the reduction in endogenous MIS, which is normally secreted by granulosa cells of growing follicles (FIG. 6—model). It is further hypothesized that this deficit could be directly addressed by supplementing exogenous MIS, as a form of hormone replacement therapy, and that follicular negative feedback could be restored (FIG. 6—model). To test these hypotheses, both gene therapy with MIS and rhMIS protein were used to create a complete arrest in primordial follicle recruitment concurrent with chemotherapy. As a proof of concept 3 commonly used chemotherapeutic classes with well described gonadotoxicities were chosen: platinums (48), anthracyclins (49), and alkylating agents (50). Both platinums (such as carboplatinum) and anthracyclins (doxorubicin) interfere with DNA replication, and as such particularly toxic to dividing cells such as granulosa cells of secondary and antral follicles, albeit with distinct toxicity profiles (49), thus representing ideal targets for MIS oncofertile therapy. Cyclophosphamide is an alkylating agent, a class that is particularly damaging to germ cells, and the most problematic gonadotoxic chemotherapeutic in the clinic, particularly since it is often used in young girls with haematological cancers (51). The protective effect of MIS was found to be particularly dramatic in the case of DNA damaging agents (FIGS. 5F and 5G), and only weakly protective for cyclophosphamide (FIG. 5H). It is speculated that the degree of protection is likely reflective of the relative amounts of direct damage to the germ cells versus the indirect damage caused by the loss of negative feedback and "follicular burnout". A recent investigation on the relative contribution of direct versus indirect damages of various chemotherapeutics agents on follicles foreshadowed the greater protection for observed for platinum compared to cyclophosphamide and predicts an even greater protection for gemcitabine (52).

Treatment with MIS is particularly compatible with short-term oncofertility usage such as during chemotherapy, since complete blockade of folliculogenesis induces a menopausal-like state of acyclicity and hypergonadotropic hypogonadism (FIG. 4E). In some cases, such as breast cancer, reduced estradiol is considered beneficial to the treatment of the tumor (28), thus representing an additional advantage of ovarian suppression. Additionally, for conditions such as polycystic ovarian syndrome (PCOS) (53), the reduction of both folliculogenesis and androgens observed with MIS may alleviate some of its most important symptoms. However, in other contexts, chronic long-term use of MIS as a contraceptive would likely have to be associated with steroid hormone replacement therapy. Alternatively, one could envision a lower dose MIS usage where primordial follicle activation could be slowed down but not completely arrested, thus tempering depletion of the ovarian reserve in patient with diminished ovarian reserve, such as FMR1 premutation carriers (54), without compromising cyclicity. Finally, another application where MIS may be useful is for the treatment of follicular burnout associated with ovarian tissue grafting (55), an experimental fertility preservation technique in which cortical ovarian grafts are frozen and re-implanted after chemotherapy (56). The relatively modest lifespan of such grafts could be expanded if the initial primordial follicle loss upon re-implantation could be moderated.

In conclusion, it is demonstrated herein that MIS is a potent inhibitor of primordial follicle activation, and an effective contraceptive in mice. Its unique mechanism of action make it particularly suited for the protection of ovarian reserve during chemotherapy and opens up many clinical possibilities for other conditions where recruitment of follicles is dysregulated. Future studies should address the quality of the eggs being preserved and evaluate ways to mitigate the long-term effects of hypergonadotropic-hypogonadism.

Materials and Methods

Animals

This study was performed in accordance with a Massachusetts General Hospital Institutional Animal Care and Use Committee approved experimental protocol (2009N000033 and 2014N000275).

For pharmacokinetic analysis, rhMIS protein was delivered to C57BL/6N female mice (Charles River Laboratories, Wilmington, Mass.) subcutaneously (3 mg/kg; n=3), intravenously (3 mg/kg; n=3), intraperitoneally (1.5 mg/kg; n=3) or by an intraperitoneally implanted osmotic pump (ALZET 1007D, DURECT Corporation, Cupertino, Calif.; flow rate 0.5 uL/hr, filled with 1200 µg/mL of LR-MIS, n=3). After the delivery of LR-MIS, their blood samples were serially collected and analyzed.

To see the effect of AAV9 MIS to the ovaries, 6 weeks old Nu/Nu (MGH, Boston, Mass.) female mice were injected intraperitoneally with 1E10, 1E11, 3E11, 1E12 of AAV9 MIS (n=1 per each) and blood samples were serially collected. After 7 weeks of treatment, the animals were euthanized, ovaries were dissected and ovarian follicles were counted as described below.

To observe the effect of releasing ovaries from exogenous MIS ovarian suppression, 3E11 viral particles of AAV9 MIS were given i.p. to 6 weeks old C57BL/6N female mice; 60 days later one ovary per mouse was surgically transplanted orthotopically into the emptied bursa of either an AAV9 MIS or AAV9 GFP treated female mice. The mice were euthanized at either 12 or 30 days after the transplantation, and ovaries were dissected.

To see the effect of rhMIS protein intermittent ovarian suppression, Nu/Nu female mice were injected subcutaneously with 750 µg/kg of rhMIS every 12 hours. After 40 days of repeated injections, the mice were released from the injection and sacrificed 0 (n=3), 5 (n=3), 10 (n=3), 15 (n=3) or 30 days (n=3) later, and ovaries examined to assess the recovery of folliculogenesis.

Histology

Dissected ovaries were fixed in 4% Paraformaldehyde overnight at 4° C. and embedded in paraffin blocks in an automated tissue processor. For hematoxylin and eosin (H&E) staining, the whole ovary was cut at a thickness of 8 µm, and serial sections were mounted on slides and deparaffinised. After the graded series of rehydration, sections were stained with Hematoxylin (Dako, Carpinteria, Calif.) and Eosin (Sigma Aldrich, Milwaukee, Wis.), cover slipped with Cytoseal 60 (Thermo Fisher Scientific, Waltham, Mass.) and examined under the light microscope for follicle counts.

For immunohistochemistry (IHC) and immunofluorescence (IF), the ovaries were cut at 5 µm thickness and mounted on slides. Slides were deparaffinised, rehydrated and heat induced antigen retrieval was performed.

For IHC, after endogenous peroxidase was inactivated by 3% Hydrogen peroxide (Thermo Fisher Scientific), sections were blocked in TBST containing 2% donkey serum (Jackson Immuno Research, West Grove, Pa.) and incubated in primary antibody overnight at 4° C. A horseradish peroxidase conjugated secondary antibody was incubated for 1.5 hr, and the DAB system (DAKO, Santa Clara, Calif.) used to visualize the signal.

For IF, sections were blocked in 2% donkey serum blocking buffer and incubated in primary antibody overnight at 4° C. Then the sections were incubated in secondary antibodies for 1.5 hr and coverslipped with VECTASHIELD mounting medium with DAPI (Vector Laboratories, Burlingame, Calif.). The slides were examined 15 min after coverslipping under a Nikon Eclipse i80 microscope. Primary antibodies included Sheep Anti-hMISR2 polyclonal antibody (R&D Systems) and Rabbit Anti-cleaved caspase3 polyclonal antibody (Cell Signaling Technology, Danvers, Mass.), Rabbit Anti-DDX4/MVH polyclonal antibody (Abcam, Cambridge, Mass.), and Mouse Anti-p63 monoclonal antibody (Biocare Medical, Concord, Calif.). Secondary antibodies included Donkey Anti-Sheep IgG conjugated to HRP (R&D Systems), Donkey Anti-Rabbit-IgG antibody conjugated to HRP (Jackson Immuno Research), Alexa Fluor 488 Donkey Anti-Sheep IgG antibody, Alexa Fluor 555 conjugated Donkey Anti-Rabbit-IgG antibody and Alexa Fluor 647 conjugated Donkey Anti Mouse-IgG antibody (Thermo Fisher Scientific).

Follicle Counts

Follicle counts were performed as previously described (57). Briefly, the total number of follicles in each ovary was estimated by counting the numbers of follicles in every fifth sections of H&E stained whole ovaries and applying a correction factor. Follicles were classified into five stages; primordial, primary, secondary, antral, and atretic follicles. Only those which had an oocyte nucleus were scored. Follicles whose oocyte was surrounded by a layer of squamous granulosa cells were classified as primordial follicles. If a single layer of cuboidal granulosa cells was observed, it was classified as primary follicles. Secondary follicles had multiple layers of cuboidal granulosa cells. If an antrum was observed in the granulosa cell layers, the follicle was classified as an antral follicle. Atretic follicles were counted only when an aberrant oocyte and multiple layers of pycnotic granulosa cells were observed.

Blood Sampling

Mouse blood was taken by pricking facial veins, or by cardiac puncture at endpoint, and collected in a EDTA2Na tube and centrifuged at 3000 rpm for 10 min. Serum was taken from the supernatant and stored at −20° C. until analysis. For frequently repeated, small volume blood sampling, lateral tail blood was collected; 10 ul was collected and diluted immediately in 90 ul of 1% BSA/PBS, centrifuged and stored as described above.

Vaginal Cycling

Female mice were co-housed in groups of 4 with male bedding, and vaginal smears were taken once a day, at least 5 days a week, between 10 am and 11 am. Dried smears were stained with Giemsa (Sigma Aldrich, Milwaukee, Wis.) for 15 minutes, rinsed with distilled water, dried at room temperature, and coverslipped with Cytoseal 60 (Thermo Fisher Scientific, Waltham, Mass.). The slides were examined by two observers under a light microscope and the stage of cycle determined according to the Allen criteria (58). To compare the time spent in estrus versus other stages the cycling period was divided in two periods: the days of estrus were counted from the day of injection (d0) to day 34, and from day 35 to day 70 and the ratio of days spent in estrus calculated.

ELISA

The ELISA to measure human MIS was performed as previously reported (20). Briefly, a 96 well plate was coated with mouse monoclonal anti human recombinant MIS antibody (6E11) overnight at 4° C. and blocked with 1% BSA/PBST (Jackson Immuno Research Laboratories, West Grove, Pa.) for 2 hours at room temperature. The standard MIS and samples were loaded and incubated overnight at 4° C. The rabbit polyclonal anti MIS antibody (MGH6) was incubated for 1 hour at room temperature and then donkey anti rabbit IgG antibody conjugated to HRP (Jackson ImmunoResearch, West Grove, Pa.) was incubated for 1 hour at 4° C. The plate was developed using TMB (SigmaAldrich, Milwaukee, Wis.) and the light absorbance was read at 595 nm in a mircoplate reader (Vector2 1420 multilabeled counter, Perkin Elmer.)

Murine MIS/P4/E2/LH/FSH/INHB serum levels were measured at the Ligand Assay & Analysis Core of the Center for Research in Reproduction at University of Virginia School of Medicine. Briefly, mouse serum was taken by cardiac puncture or facial vein and used for measuring endogenous mouse MIS, E2, testosterone, LH or FSH. ELISAs were performed under the cooperative agreement with Mouse endogenous MIS was measured with ELISA kit from AnshLabs, E2 with ELISA kit from Calbiotech, testosterone with ELISA kit from IBL-America, and LH and FSH with Endocrine multiplex assay from EMD Millipore.

Mating Experiments

The C57BL/6N mice were paired 7 days after the AAV9 virus injection. Each pair of one AAV9 Empty treated female and one AAV9 MIS treated female were caged with one experienced breeder male. Once a pregnant mother was identified it was separated until parturition, the size of the litter was recorded, the pups were removed and the mother was reintroduced to the male again. The female mice were separated for two months after five months of mating and then mated again to new experienced breeder males for one month at their $12^{th}$ month of age. While the mice were separated, blood samples and vaginal smears were taken for cycling and endocrine studies.

Chemotherapy Models

AAV9

Peri-pubertal 6-7 weeks old Nu/Nu (N=20) mice were xenografted s.c. with 1M cells of the ovcar5 ovarian cancer cell line in the right flank. Once the tumor reached a size of 500 mm$^3$, 26d after grafting, mice were injected with AAV9-MIS (N=10) or AAV9-GFP (N=10) at dose of 3E11 particles per mouse. The mice were then treated with chemotherapeutics or saline 24 h after AAV injection. A 2nd dose of chemotherapeutic agents was given 7 days after the 1st dose. The chemotherapeutic agents used for this experiment are either 3 mg/kg of doxorubicin i.v. (N=10) or 80 mg/kg of carboplatin i.p. (N=10). The animals were euthanized 3 days for doxorubicin or 5 days for carboplatin after the 2nd dose of chemotherapeutics, as the tumor exceeded 1 cm$^3$, and the ovaries were recovered and fixed for analysis.

Osmotic Pump

Peri-pubertal 6-7 week old C57BL/6N mice were surgically implanted in the peritoneal cavity with an osmotic pump (1007D) (ALZET, Cupertino, Calif.) filled with 100 µL of rhMIS (1200 µg/mL) or saline and then treated with chemotherapeutics or saline intraperitoneally a day after the implantation. A 2nd dose of chemotherapeutic agents was given 7 days after the 1st dose. The implanted pump was replaced every 7 days except for the doxorubicin experiment where the pump was replaced every 5 days. Chemotherapeutic regimens used for this experiment are as follows: 7.5 mg/kg i.p. of doxorubicin followed by 6.0 mg/kg i.p. for the second round, or 60 mg/kg of carboplatin i.p. for both rounds, or 60 mg/kg of cyclophosphamide for both rounds. The animals were euthanized 7 days after the 2nd dose of chemotherapeutic agents and the ovaries dissected for analysis.

Statistical Analysis

All analyses were performed with Prism7 (GraphPad, La Jolla, Calif.). When two groups of data with a known direction were compared an unpaired one-tailed Student's t-test was used. When the distribution of data was not normal, Mann-Whitney test was used for analysis. For four groups of chemotherapy analysis, each follicle counts were compared by two-way analysis of variance for multiple comparisons followed by Holm-Sidak's post-hoc test. The breeding experiment was assessed by one-way analysis of variance for multiple comparisons followed by Holm-Sidak's post hoc test.

Surgical Procedures

Pump Implantation

Osmotic pumps were primed prior to implantation by filling them with either 100 ul of rhMIS (1200 µg/mL) or saline and incubated in saline at 37° C. for 3 hrs. The mice were anesthesised with isoflurane and the procedure was performed on a heated pad. To implant the pump, a small incision was performed on the flank, the osmotic pump installed in peritoneal cavity, and the wound closed with metal clips. Mice were given daily dosing of (2.5 mg/ml) Carprofen analgesic by oral gavage (100 µl) prior to the surgery and 2 days post-operatively.

Ovarian Transplants.

Ovarian transplants were performed as previously described (59). Briefly, both the recipient and donor mice were anesthetized and small incisions were performed on the back wall at the level of the kidney. The ovary, oviduct, and the distal part of the uterus were exteriorized taking care not to damage it, a small incision was performed on the ovarian bursa taking care not to tear it. The ovary of the donor was carefully resected and introduced into the emptied bursa of the recipient. The ovary and reproductive tract was replaced into the peritoneal cavity, the wound closed with metal clips and the mice received post-operative care. In this manner transplants were performed from AAV9 MIS treated mice (for 60 days) into either AAV9 GFP or AAV9 MIS recipients, and animals were euthanized and ovaries examined either 12 or 30 days post-operatively.

Production of rhMIS Protein

RhMIS protein was purified as previously described (20). Briefly, a CHOK1 clone stably transfected with the LR-MIS vector was grown in hyperflasks, and serum-free conditioned media collected after 72 h of incubation is concentrated 10-20× using a tangential flow over a size-exclusion membrane. The concentrated media is incubated with sepharose beads conjugated with an anti-human MIS monoclonal antibody (6E11). Bound rhMIS is serially eluted with a glycine buffered solution (pH 2.9). The eluates containing high levels of rhMIS protein were dialyzed for 4 h against 10× volume of phosphate buffered saline (PBS). All purified protein is tested for activity in the rat urogenital ridge bioassay, and stored at −80 C until use.

Production of AAV9 Virus

Recombinant AAV9 viral particles were produced, purified, and titrated as previously described (21). Briefly, HEK293 cells were transfected with a pAAV plasmid containing the LR-MIS construct flanked with inverted terminal repeats (ITR), and the virus was rescued with plasmids expressing AAV9 capsid proteins, and adenoviral helper proteins. Particles of rAAV were sedimented by cesium chloride gradient and purified by dialysis. The rAAV vector titer was quantified by silver staining of capsid proteins and quantitative PCR of genome copy.

Fetal Rat Urogenital Ridge Bioassay

The rat urogenital organ culture bioassay for MIS was performed as previously described (20, 38). In brief, timed pregnant Sprague Dawley rat's (Envigo, South Easton, Mass.) E14.5 female embryonic urogenital ridges containing ovary, Wolffian and Mullerian ducts, and intervening mesenephros were dissected and incubated on 2% agarose gel over CMRL 1066 media (ThermoFisherScientific, Waltham, Mass.) supplemented with 10% FemaleFCS, 1% penicillin/streptomycin, 1% L-glutamine, 1% Fungizone (ThermoFisherScientific, Waltham, Mass.), and 5 nM testosterone (Sigma-Aldrich, St. Louis, Mo.). After incubation for 72 hrs in presence of the sample, the specimens were fixed, embedded in paraffin, sectioned and stained with H&E. The sections were then scored under a light microscope by experienced blinded observers. Cultures were carried out with the purified rhMIS at 5 µg/ml, rhMIS solution at 5 µg/ml recovered from the pumps implanted for 7 days in mice, and commercially available recombinant MIS C-terminus (R&D systems, Minneapolis, Minn.) at a final concentration of 5 µg/ml.

Example 4

Administration of LRMIS during doxorubicin cycles in mice leads to a 2.9 fold increase in ovarian reserve compared to doxorubicin controls. As used herein, "MIS" refers to the purified recombinant LR-MIS protein formulation. This increased ovarian reserve translates into greater reproductive output, as measured by cumulative number of pups over a 5 month period in continuous mating pairs. The fertility gains widen with time, suggesting a delay or prevention of primary ovarian failure, and indicate egg quality is preserved.

Furthermore, a lower incidence of uterine dystocia was observed in the LRMIS treated group, suggesting treatment may be protective of the uterus.

It was previously shown that treatment with LRMIS during exposure to doxorubicin (DOX) can significantly reduce the loss of ovarian reserve (1). In these experiments, implantation of an osmotic pump delivering recombinant LRMIS intraperitoneally in C57BL/6 mice during two cycles of DOX resulted in a 2.9-fold ($p<0.001$) increase in primordial follicle counts compared to control mice receiving chemotherapy plus saline. Without wishing to be bound by theory, it is hypothesized that the increase in ovarian reserve should translate into greater fertility post-treatment and lower/delayed incidence of primary ovarian insufficiency.

Furthermore, Doxorubicin is known to have significant cardiotoxicity (2) and to be associated with uterine dysfunction in mice. MISR2 is expressed in the adult uterus, and is associated with a uterine stem cell capable of repairing the uterine damage associated with parturition (3). Without wishing to be bound by theory, it is hypothesized that treatment with LRMIS should lessen uterine damage and translate into lower rates of uterine dystocia.

Results

Figure 9A:
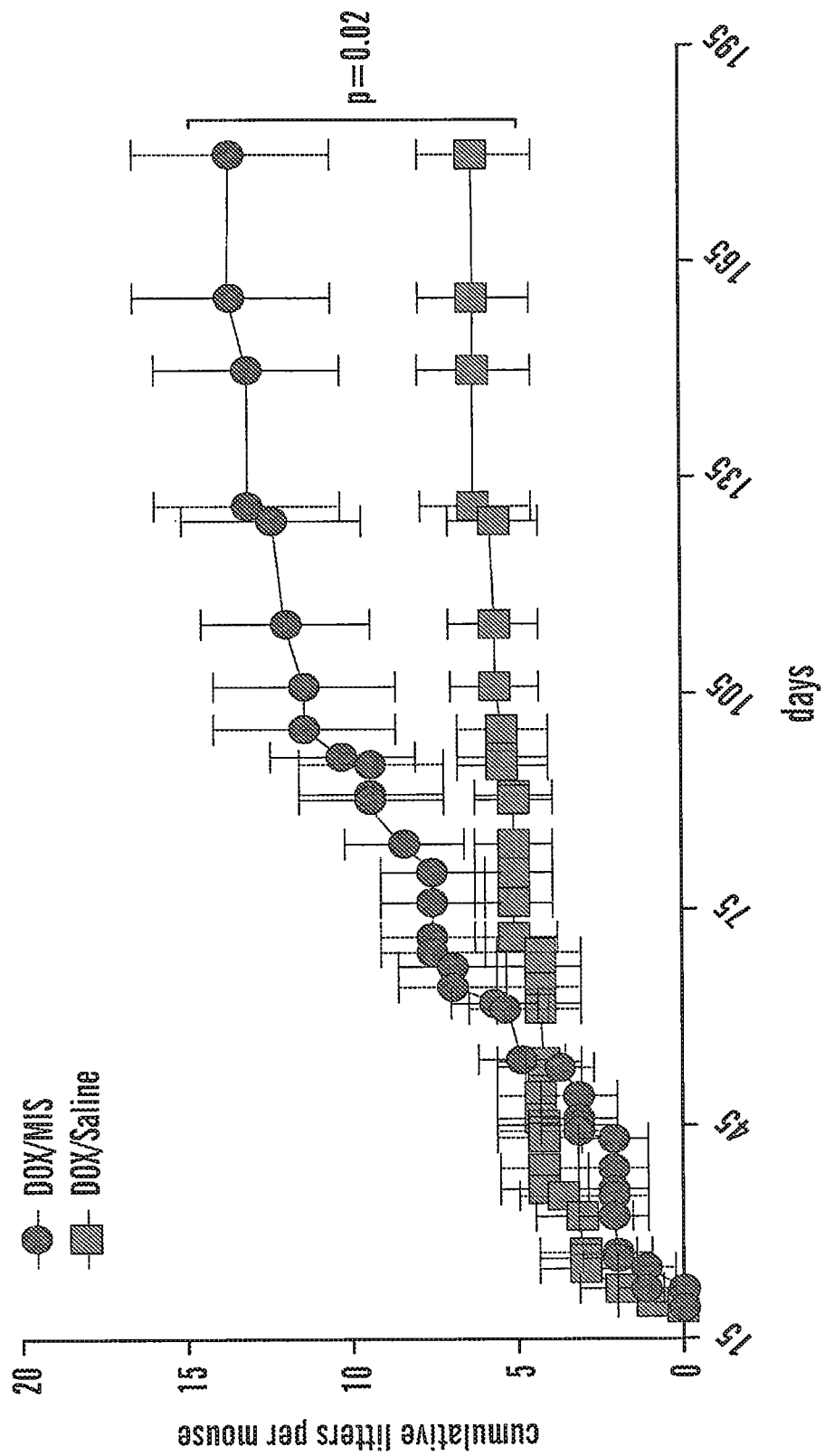
FIGS. 9A and 9B present experimental data showing the fertility of mice treated with MIS via implantable pumps and given doxorubicin IP in long-term continuous mating pairs. C57BL/6 mice were implanted with Alzet™ pumps delivering MIS IP at 600 ng/h (or saline control) and treated weekly with doxorubicin (6 mg/kg) and, after a 2 week recovery period, placed in mating pairs which included one treated and one control female together with a breeding male.
Figure 9B:
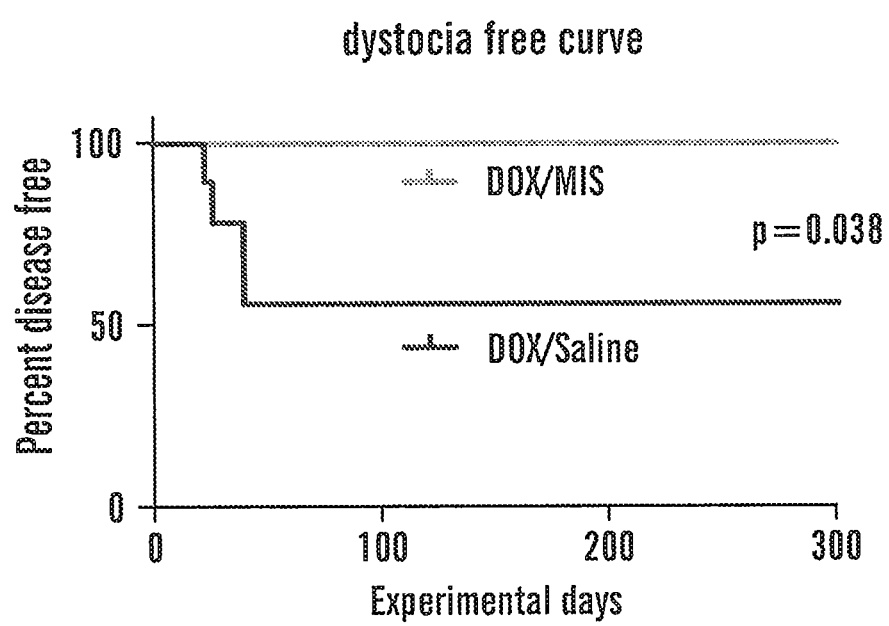
Figure 10:
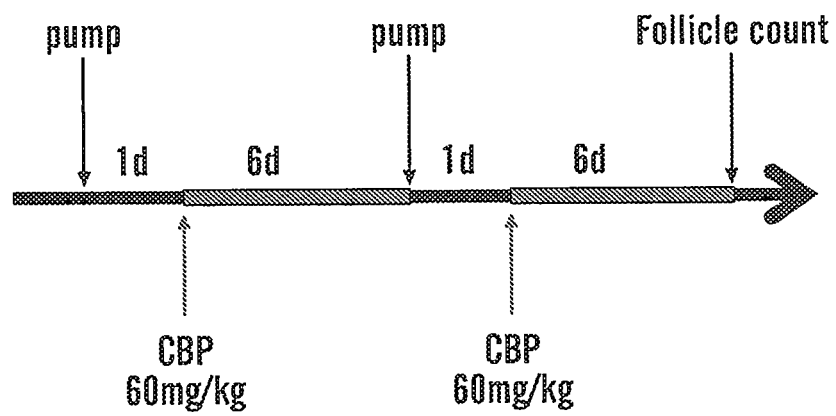
FIG. 10 shows an exemplary schematic of the treatment scheme used in an experiment where LR-MIS protein was delivered by an implanted osmotic pumps, when CBP (60 mg/kg) was also administered to the mouse.
Figure 11:
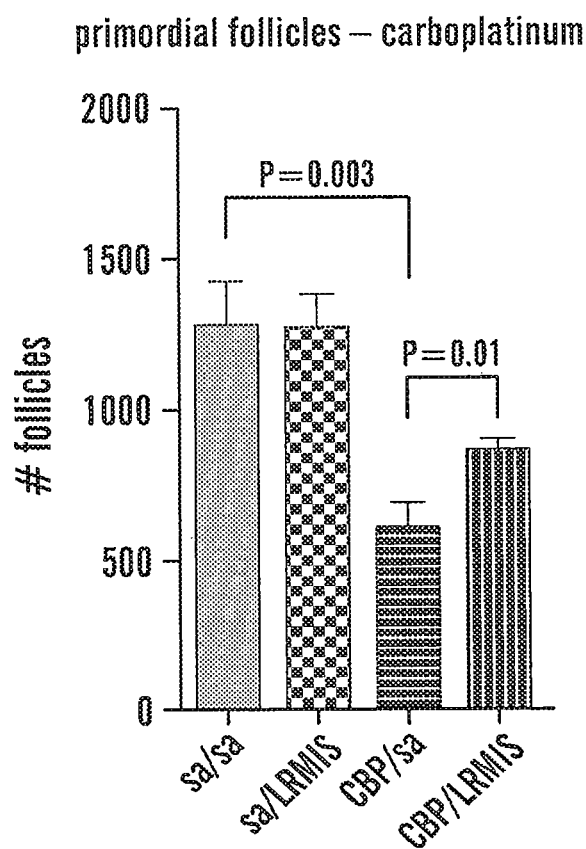
FIG. 11 presents experimental data showing primordial follicle counts following chemotherapy and LR-MIS protein treatment. 5 mice from each group treated with saline/saline, saline/LR-MIS, carboplatin/saline, or carboplatin/LR-MIS were analyzed by follicle counts in one ovary with complete sectioning Mean+SEM.
Figure 12:
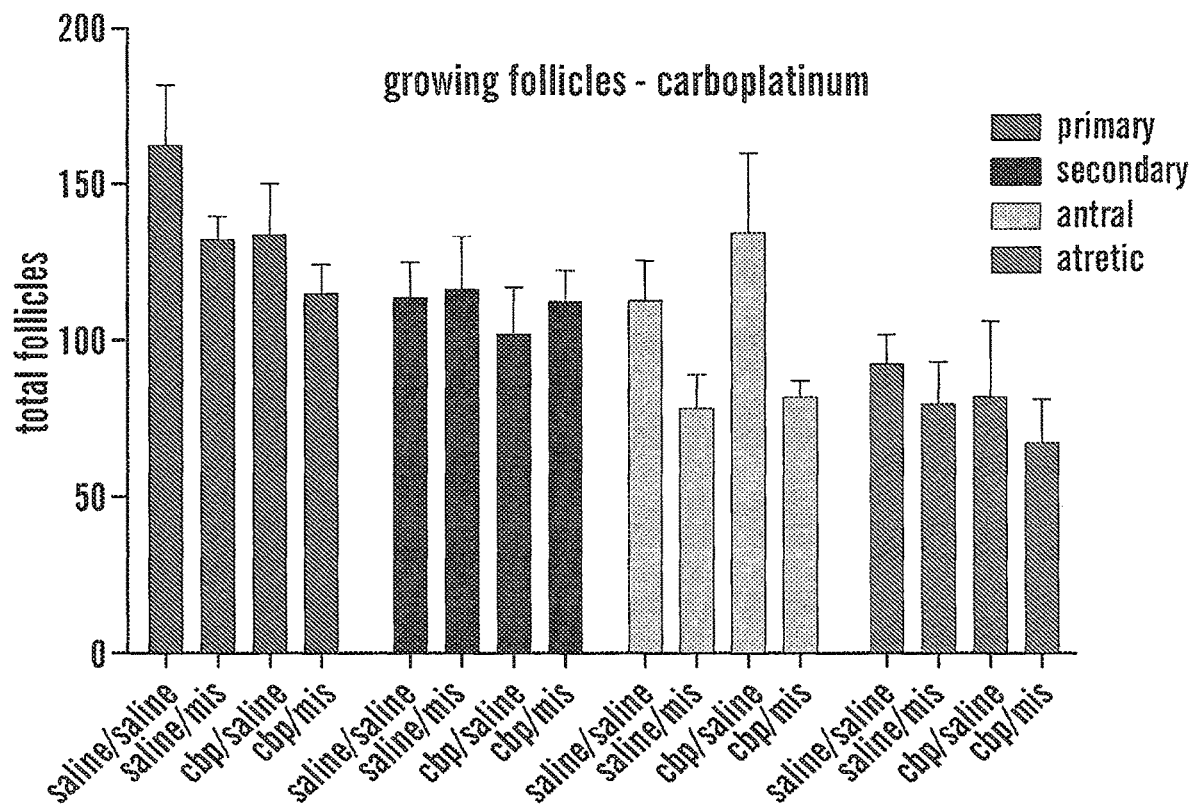
FIG. 12 presents experimental data showing total follicle counts following chemotherapy and LR-MIS protein treatment. 5 mice from each group treated with saline/saline, saline/LR-MIS, carboplatin/saline, or carboplatin/LR-MIS were analyzed by follicle counts in one ovary with complete sectioning Bars represent the mean+SEM.
Figure 13:
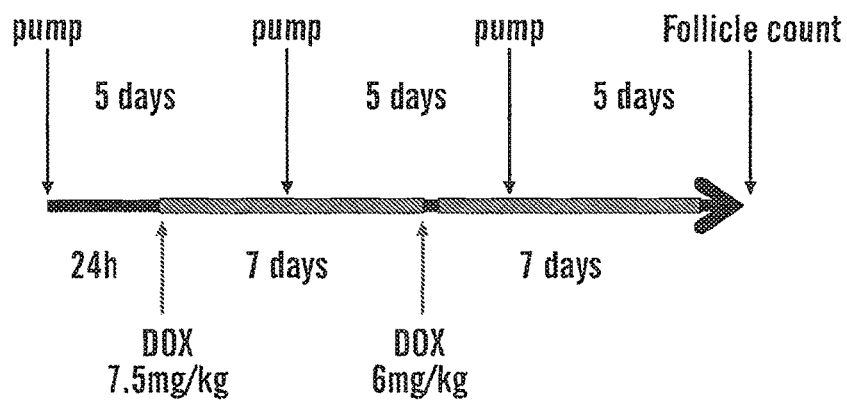
FIG. 13 presents a schematic of the treatment scheme used in an experiment where LR-MIS protein was delivered by an implanted osmotic pumps, when DOX (7.5 mg/kg) was also administered to the mouse.
Figure 14:
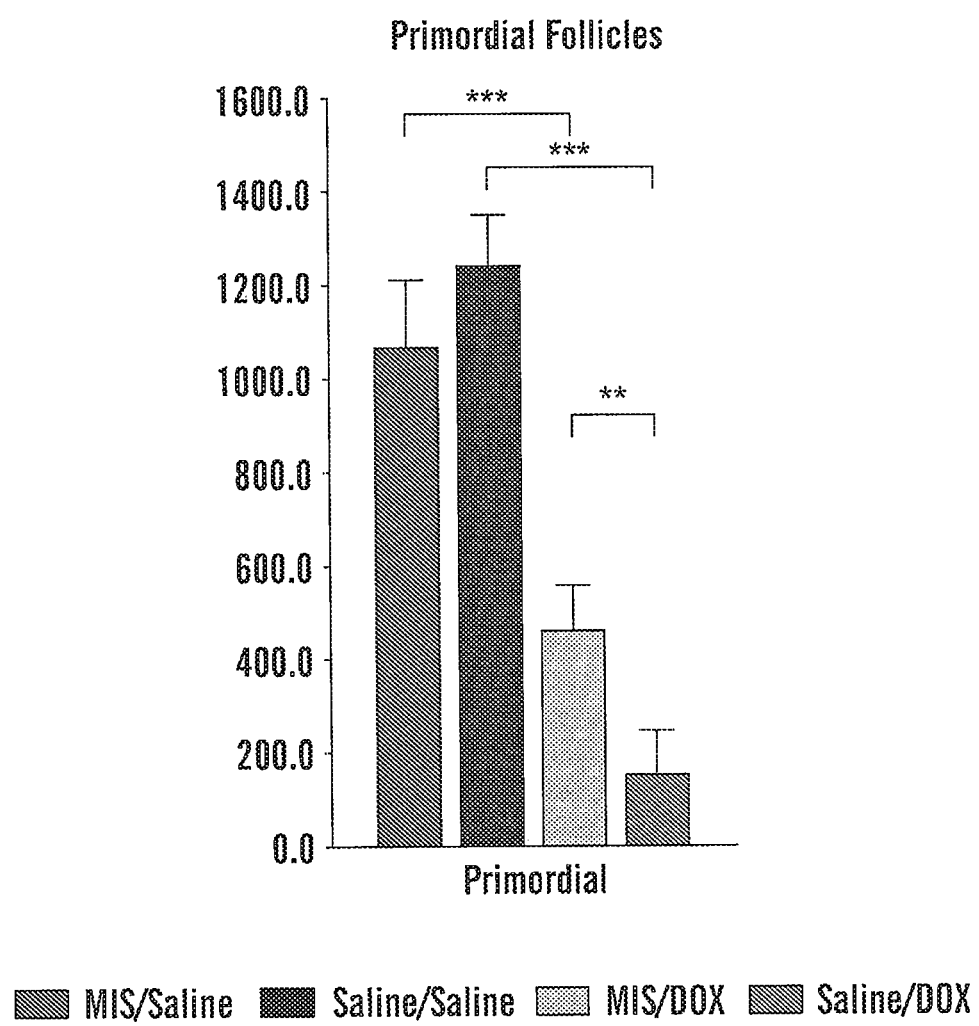
FIG. 14 presents experimental data showing primordial follicle counts following chemotherapy and LR-MIS treatment. 3-5 mice from each group treated with saline/saline, saline/LR-MIS, carboplatin/saline, or carboplatin/LR-MIS were analyzed by follicle counts in two ovaries with complete sectioning.  $p<0.02$, * $p<0.01$.
Figure 15:
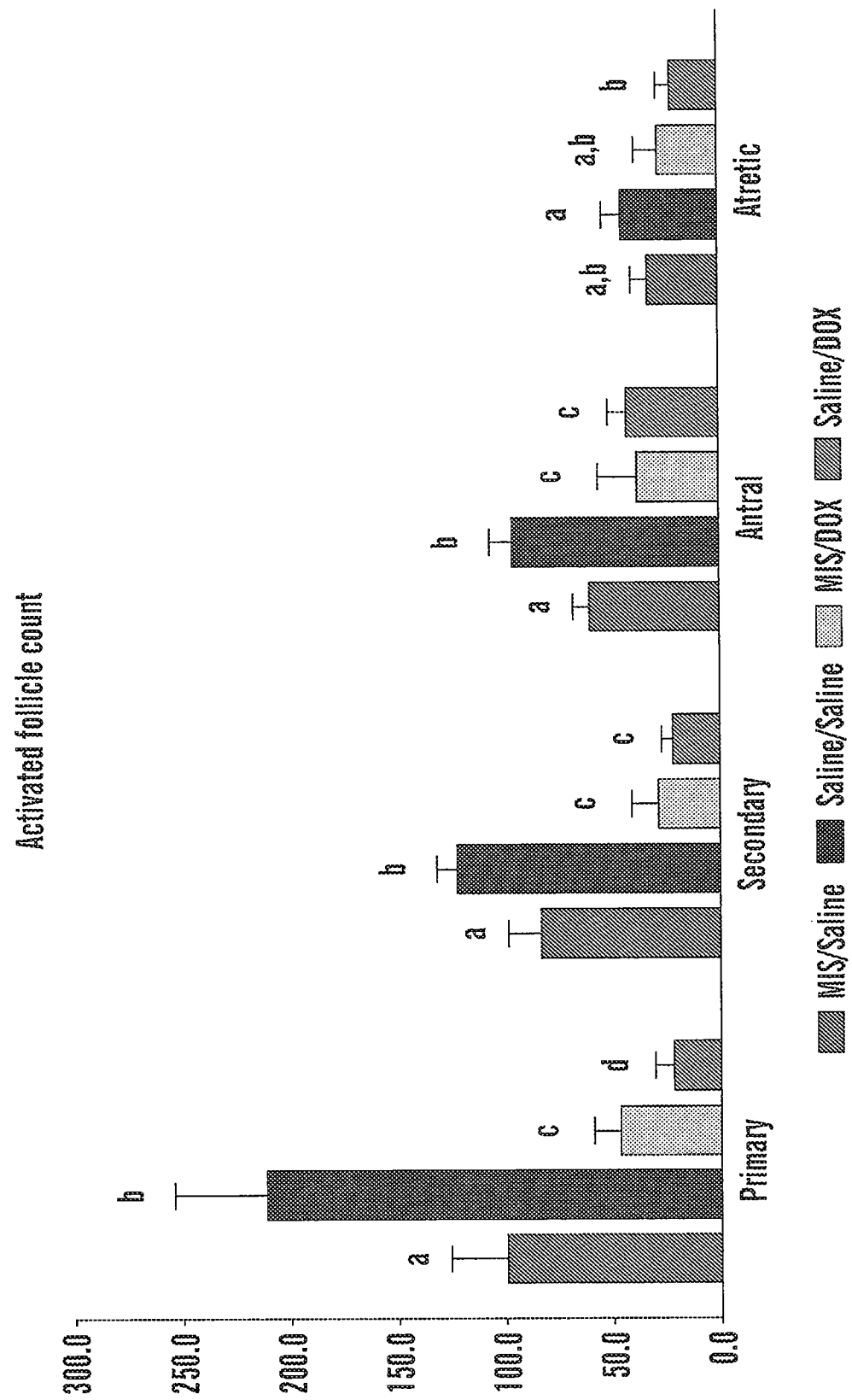
FIG. 15 presents experimental data showing total follicle counts following chemotherapy and LR-MIS treatment. 5 mice from each group treated with sa/sa, sa/PRV100, DOX/sa, DOX/PRV100 from exp AK were analyzed by follicle counts in two ovaries with complete sectioning. Different letters above the bars indicate significant differences within each follicle type.
Figure 16A:
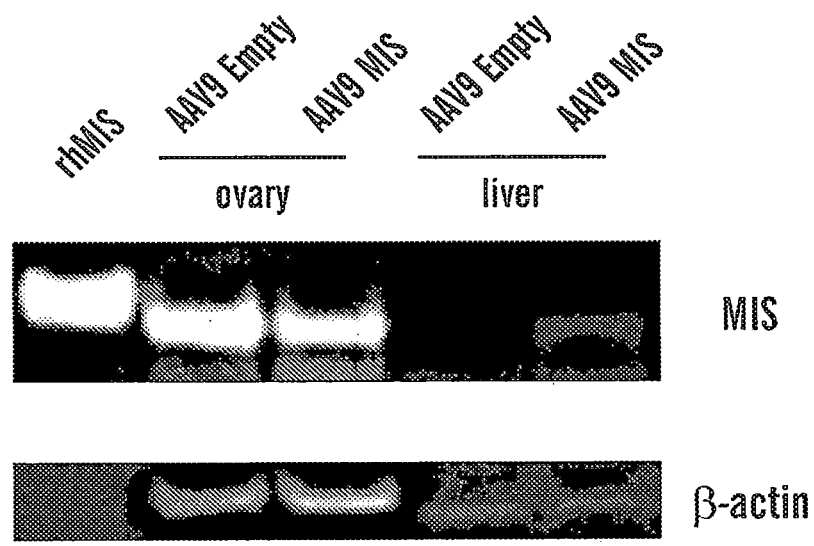
FIGS. 16A and 16B present experimental data showing expression of MIS in the ovary following AAV9 treatment and chemotherapy-induced changes in endogenous murine MIS.
Figure 16B:
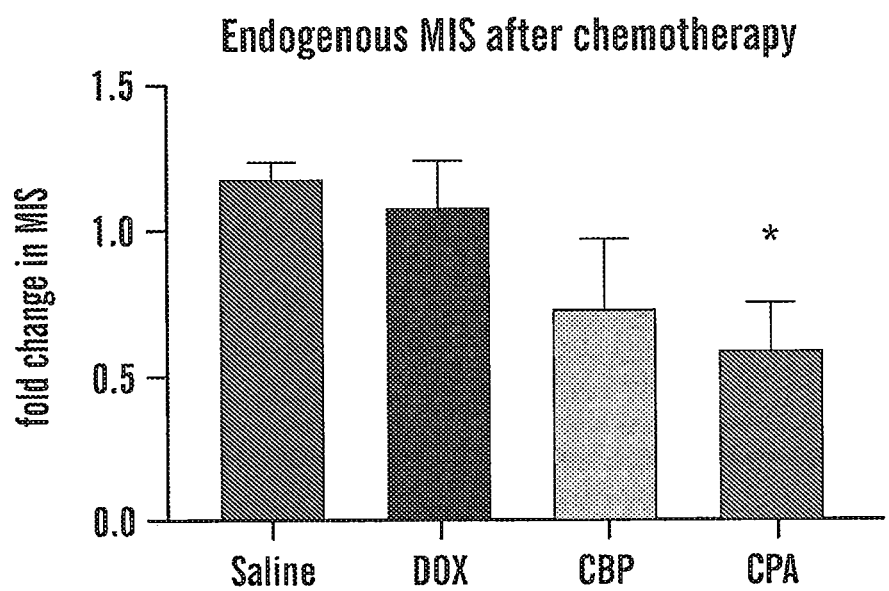

C57BL/6 mice (N=5/group) were co-treated with an intraperitoneal implantation of an osmotic pump delivering recombinant MIS during two cycles of doxorubicin (DOX; 6 mg/kg IP/week). The treated animals were subsequently mated continuously for over five months and their fertility was monitored. These breeding experiments revealed an increase in the cumulative number of pups compared to control mice receiving chemotherapy plus saline ($p=0.02$) (FIG. 9A) and also resulted in a decrease of dystocia, a previously documented lethal complication of DOX treatment ($p=0.038$) (FIG. 9B).

REFERENCES

The references herein are incorporated herein in their entirety by reference.

1. Baker M L, Metcalfe S A, Hutson J M (1990) Serum levels of müllerian inhibiting substance in boys from birth to 18 years, as determined by enzyme immunoassay. *J Clin Endocrinol Metab* 70(1):11-15.
2. Hudson P L, et al. (1990) An immunoassay to detect human müllerian inhibiting substance in males and females during normal development. *J Clin Endocrinol Metab* 70(1):16-22.
3. Seifer D B, et al. (1993) Gonadotropin-releasing hormone agonist-induced differences in granulosa cell cycle kinetics are associated with alterations in follicular fluid müllerian-inhibiting substance and androgen content. *J Clin Endocrinol Metab* 76(3):711-714.
4. Josso N, Picard J Y, Rey R, di Clemente N (2006) Testicular anti-Müllerian hormone: history, genetics, regulation and clinical applications. *Pediatr Endocrinol Rev PER* 3(4):347-358.
5. Dewailly D, et al. (2014) The physiology and clinical utility of anti-Mullerian hormone in women. *Hum Reprod Update* 20(3):370-385.
6. Jost A (1947) Sur les dérivés mülleriens d'embryons de lapin des deux sexes castrés a 21 jours. *C R Seances Soc Biol Fil* 141(3-4): 135.
7. Behringer R R, Finegold M J, Cate R L (1994) Müllerian-inhibiting substance function during mammalian sexual development. *Cell* 79(3):415-425.
8. Nilsson E E, Schindler R, Savenkova M I, Skinner M K (2011) Inhibitory actions of Anti-Müllerian Hormone (AMH) on ovarian primordial follicle assembly. *PloS One* 6(5):e20087.
9. Hirobe S, He W W, Lee M M, Donahoe P K (1992) Mullerian inhibiting substance messenger ribonucleic acid expression in granulosa and Sertoli cells coincides with their mitotic activity. *Endocrinology* 131(2): 854-862.
10. Teixeira J, et al. (1996) Developmental expression of a candidate müllerian inhibiting substance type II receptor. *Endocrinology* 137(1):160-165.
11. Baarends W M, et al. (1994) A novel member of the transmembrane serine/threonine kinase receptor family is specifically expressed in the gonads and in mesenchymal cells adjacent to the mullerian duct. *Development* 120(1): 189-197.
12. Baarends W M, et al. (1995) Anti-müllerian hormone and anti-müllerian hormone type II receptor messenger ribonucleic acid expression in rat ovaries during postnatal development, the estrous cycle, and gonadotropin-induced follicle growth. *Endocrinology* 136(11):4951-4962.
13. di Clemente N, et al. (1994) Cloning, expression, and alternative splicing of the receptor for anti-Müllerian hormone. *Mol Endocrinol Baltim Md.* 8(8):1006-1020.
14. Connolly D C, et al. (2003) Female mice chimeric for expression of the simian virus 40 TAg under control of the MISIIR promoter develop epithelial ovarian cancer. *Cancer Res* 63(6):1389-1397.
15. Durlinger A L, et al. (1999) Control of primordial follicle recruitment by anti-Müllerian hormone in the mouse ovary. *Endocrinology* 140(12):5789-5796.
16. Gigli I, Cushman R A, Wahl C M, Fortune J E (2005) Evidence for a role for anti-Mullerian hormone in the suppression of follicle activation in mouse ovaries and bovine ovarian cortex grafted beneath the chick chorioallantoic membrane. *Mol Reprod Dev* 71(4):480-488.
17. Nilsson E, Rogers N, Skinner M K (2007) Actions of anti-Müllerian hormone on the ovarian transcriptome to inhibit primordial to primary follicle transition. *Reprod Camb Engl* 134(2):209-221.
18. Ragin R C, Donahoe P K, Kenneally M K, Ahmad M F, MacLaughlin D T (1992) Human müllerian inhibiting substance-enhanced purification imparts biochemical stability and restores antiproliferative effects. *Protein Expr Purif* 3(3):236-245.
19. Lorenzo H K, et al. (2002) New approaches for high-yield purification of Müllerian inhibiting substance improve its bioactivity. *J Chromatogr B Analyt Technol Biomed Life Sci* 766(1):89-98.
20. Pépin D, et al. (2013) An albumin leader sequence coupled with a cleavage site modification enhances the yield of recombinant C-terminal Mullerian Inhibiting Substance. *Technol Elmsford N* 1(1):63-71.
21. Pépin D, et al. (2015) AAV9 delivering a modified human Mullerian inhibiting substance as a gene therapy in patient-derived xenografts of ovarian cancer. *Proc Natl Acad Sci USA* 112(32):E4418-4427.
22. Gupta S K, Malik A, Arukha A P (2015) Ovarian and oocyte targets for development of female contraceptives. *Expert Opin Ther Targets* 19(11): 1433-1446.
23. Pelosi E, Forabosco A, Schlessinger D (2015) Genetics of the ovarian reserve. *Front Genet* 6. doi:10.3389/fgene.2015.00308.
24. Knight P G, Glister C (2006) TGF-β superfamily members and ovarian follicle development. *Reproduction* 132 (2): 191-206.
25. Morgan S, Anderson R A, Gourley C, Wallace W H, Spears N (2012) How do chemotherapeutic agents damage the ovary? *Hum Reprod Update* 18(5):525-535.
26. Hudson M M (2010) Reproductive Outcomes for Survivors of Childhood Cancer. *Obstet Gynecol* 116(5):1171.
27. Green D M, et al. (2009) Ovarian Failure and Reproductive Outcomes After Childhood Cancer Treatment: Results From the Childhood Cancer Survivor Study. *J Clin Oncol* 27(14):2374.
28. Hachem H E, Atallah D, Grynberg M (2014) Fertility preservation in breast cancer patients. *Future Oncol* 10(10):1767-1777.
29. Woodruff T K (2007) The emergence of a new interdiscipline: oncofertility. *Cancer Treat Res* 138:3-11.
30. Lobo R A (2005) Potential Options for Preservation of Fertility in Women. *N Engl J Med* 353(1):64-73.
31. Moore H C F, et al. (2015) Goserelin for ovarian protection during breast-cancer adjuvant chemotherapy. *N Engl J Med* 372(10):923-932.
32. Elgindy E, Sibai H, Abdelghani A, Mostafa M (2015) Protecting Ovaries During Chemotherapy Through Gonad Suppression: A Systematic Review and Meta-analysis. *Obstet Gynecol* 126(1):187-195.
33. Lambertini M, et al. (2015) Ovarian suppression using luteinizing hormone-releasing hormone agonists during chemotherapy to preserve ovarian function and fertility of breast cancer patients: a meta-analysis of randomized studies. *Ann Oncol* 26(12):2408-2419.
34. Oktay K, Briggs D, Gosden R G (1997) Ontogeny of Follicle-Stimulating Hormone Receptor Gene Expression in Isolated Human Ovarian Follicles. *J Clin Endocrinol Metab* 82(11):3748-3751.
35. Lee M M, et al. (1997) Measurements of serum müllerian inhibiting substance in the evaluation of children with nonpalpable gonads. *N Engl J Med* 336(21):1480-1486.
36. Gustafson M L, et al. (1992) Müllerian inhibiting substance as a marker for ovarian sex-cord tumor. *N Engl J Med* 326(7):466-471.
37. Cate R L, et al. (1986) Isolation of the bovine and human genes for Müllerian inhibiting substance and expression of the human gene in animal cells. *Cell* 45(5):685-698.
38. Price J M, Donahoe P K, Ito Y (1979) Involution of the female Mullerian duct of the fetal rat in the organ-culture assay for the detection of Mullerian Inhibiting Substance. *Am J Anat* 156(2):265-284.
39. Grive K J, et al. (2016) TAF4b Regulates Oocyte-Specific Genes Essential for Meiosis. *PLoS Genet* 12(6): e1006128.
40. Franks L M, Payne J (1970) The Influence of Age on Reproductive Capacity in C57bl Mice. *J Reprod Fertil* 21(3):563-565.
41. Xu J, Bishop C V, Lawson M S, Park B S, Xu F (2016) Anti-Müllerian hormone promotes pre-antral follicle growth, but inhibits antral follicle maturation and dominant follicle selection in primates. *Hum Reprod Oxf Engl* 31(7): 1522-1530.
42. Schmidt K L T, Kryger-Baggesen N, Byskov A G, Andersen C Y (2005) Anti-Müllerian hormone initiates growth of human primordial follicles in vitro. *Mol Cell Endocrinol* 234(1-2):87-93.
43. Durlinger A L L, et al. (2002) Anti-Müllerian hormone inhibits initiation of primordial follicle growth in the mouse ovary. *Endocrinology* 143(3):1076-1084.
44. Cimino I, et al. (2016) Novel role for anti-Müllerian hormone in the regulation of GnRH neuron excitability and hormone secretion. *Nat Commun* 7:10055.
45. Garrel G, et al. (2016) Anti-Müllerian hormone: a new actor of sexual dimorphism in pituitary gonadotrope activity before puberty. *Sci Rep* 6:23790.
46. Takahashi M, Koide S S, Donahoe P K (1986) Müllerian inhibiting substance as oocyte meiosis inhibitor. *Mol Cell Endocrinol* 47(3):225-234.
47. Li J, et al. (2015) Vectored antibody gene delivery mediates long-term contraception. *Curr Biol* 25(19): R820-R822.
48. Li X, Kang X, Deng Q, Cai J, Wang Z (2013) Combination of a GnRH agonist with an antagonist prevents flare-up effects and protects primordial ovarian follicles in the rat ovary from cisplatin-induced toxicity: a controlled experimental animal study. *Reprod Biol Endocrinol RBE* 11:16.
49. Morgan S, Lopes F, Gourley C, Anderson R A, Spears N (2013) Cisplatin and doxorubicin induce distinct mecha- 50. Kalich-Philosoph L, et al. (2013) Cyclophosphamide triggers follicle activation and "burnout"; AS101 prevents follicle loss and preserves fertility. *Sci Transl Med* 5(185): 185ra62.
51. van der Kaaij M A E, van Echten-Arends J, Simons A H M, Kluin-Nelemans H C (2010) Fertility preservation after chemotherapy for Hodgkin lymphoma. *Hematol Oncol* 28(4):168-179.
52. Yuksel A, et al. (2015) The magnitude of gonadotoxicity of chemotherapy drugs on ovarian follicles and granulosa cells varies depending upon the category of the drugs and the type of granulosa cells. *Hum Reprod Oxf Engl* 30(12): 2926-2935.
53. McAllister J M, Legro R S, Modi B P, Strauss J F (2015) Functional genomics of PCOS: from GWAS to molecular mechanisms. *Trends Endocrinol Metab* TEN/26(3):118-124.
54. Sullivan S D, Welt C, Sherman S (2011) FMR1 and the continuum of primary ovarian insufficiency. *Semin Reprod Med* 29(4):299-307.
55. Gavish Z, et al. (2014) Follicle activation and "burn-out" contribute to post-transplantation follicle loss in ovarian tissue grafts: the effect of graft thickness. *Hum Reprod Oxf Engl* 29(5):989-996.
56. Jensen A K, et al. (2016) Cryopreservation of ovarian tissue for fertility preservation in a large cohort of young girls: focus on pubertal development. *Hum Reprod Oxf Engl*. doi:10.1093/humrep/dew273.
57. Pépin D, Paradis F, Perez-Iratxeta C, Picketts D J, Vanderhyden B C (2013) The imitation switch ATPase Snf2l is required for superovulation and regulates Fgl2 in differentiating mouse granulosa cells. *Biol Reprod* 88(6): 142.
58. Allen E (1922) The oestrous cycle in the mouse. *Am J Anat* 30(3):297-371.
59. Nagy A (2002) *Manipulating the Mouse Embryo: A Laboratory Manual, Third Edition* (Cold Spring Harbor Laboratory Press, Cold Spring Harbor, N.Y). 3rd edition.
1. Kano M, et al. (2017) AMH/MIS as a contraceptive that protects the ovarian reserve during chemotherapy. *Proc Natl Acad Sci USA* 114(9):E1688-E1697.
2. McGowan J V, et al. (2017) Anthracycline Chemotherapy and Cardiotoxicity. *Cardiovasc Drugs Ther* 31(1):63-75.
3. Huang C-C, Orvis G D, Wang Y, Behringer R R (2012) Stromal-to-Epithelial Transition during Postpartum Endometrial Regeneration. *PLOS ONE* 7(8):e44285.

What is claimed is:

1. A method for uterine protection in a female subject, comprising administering to the female subject a composition comprising a recombinant Mullerian Inhibiting Substance (MIS) protein, wherein the recombinant MIS protein has at least 95% sequence identity to amino acid residues 26-451 of SEQ ID NO: 3, wherein amino acid residue 450 of SEQ ID NO: 3 (MIS) is changed from Q to R, to increase cleavage of the recombinant MIS protein as compared to the absence of the modification, wherein the uterine protection is a reduction in uterine lining thinning or a reduction of uterine dystocia, and wherein administration is via a transdermal patch or pump for continuous administration or pulse administration to achieve superphysiological levels of recombinant MIS protein in the blood of the subject relative to normal MIS protein levels.

2. The method of claim 1, wherein the recombinant MIS protein comprises amino acid residues 25-559 of SEQ ID NO: 4 (LR-MIS) or a polypeptide which has at least 96% sequence identity to the amino acid sequence of amino acid residues 25-559 of SEQ ID NO: 4 (LR-MIS); or is a homodimer comprising two monomers, each monomer comprising (i) a N-terminal domain of the recombinant MIS protein comprising amino acids 26-451 of SEQ ID NO: 3 (MIS), wherein amino acid residue 450 of SEQ ID NO: 3 (MIS) is changed from Q to R, and (ii) a C-terminal domain of the recombinant MIS protein comprising amino acids residues 452-546 of SEQ ID NO: 3 (MIS).

3. The method of claim 1, wherein the female subject has cancer and will be treated with, or is currently being treated with, or has been treated with, a cancer treatment selected from chemotherapy, radiotherapy, chemo-radiotherapy, or surgery;

has an autoimmune disease and will be treated with, or is currently being treated with, or has been treated with, an immunotherapy;

will be treated with, or is currently being treated with, or has been treated with, a cytotoxic drug or cytotoxic agent that causes cell death or cell damage to cells in the uterus or ovary; or will be treated with, or is currently being treated with, or has been treated with, a long-term treatment regimen.

4. The method of claim 1, wherein the superphysiological levels of recombinant MIS protein is sufficient to result in any of the following:

a. a concentration of MIS protein in the blood of the subject that is 10% to 50% higher as compared to the absence of administration of the recombinant MIS protein;

b. a concentration of MIS protein in the blood of the subject that is 50% to 100% higher as compared to the absence of administration of the recombinant MIS protein;

c. a concentration of MIS protein in the blood of the subject that is 2 to 5-fold higher or more than 5-fold higher as compared to the absence of administration of the recombinant MIS protein; or d. a concentration of MIS protein in the blood of the subject of between 1 µg/ml-5 µg/ml.

5. The method of claim 4, wherein the superphysiological levels of recombinant MIS protein is administered between 0.001 mg/kg per hour and 0.1 mg/kg per hour.

6. The method of claim 1, wherein the female subject is in need of fertility preservation.

7. The method claim 1, wherein the female subject will undergo, or has undergone an ovarian tissue graft or cortical ovarian tissue graft.

8. The method of claim 1, wherein the MIS protein is administered prior to, in combination with, and/or concurrently with a chemotherapeutic agent or anti-cancer therapy, cytotoxic drug, or immunotherapy agent.

9. The method of claim 1, wherein the subject has an ovarian autoimmune disease or oophoritis.

* * * * *

SEQUENCE LISTING

```
<160> NUMBER OF SEQ ID NOS: 21

<210> SEQ ID NO 1
<211> LENGTH: 1680
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgaagtggg tgagcttcat cagcctgctg ttcctgttca gcagcgctta ctcccgcggt      60
gtgttccgcc gcagagcaga ggagccagct gtgggcacca gtggcctcat cttccgagaa     120
gacttggact ggcctccagg cagcccacaa gagcctctgt gcctggtggc actgggcggg     180
gacagcaatg gcagcagctc ccccctgcgg gtggtggggg ctctaagcgc ctatgagcag     240
gccttcctgg gggccgtgca gagggcccgc tggggccccc gagacctggc caccttcggg     300
gtctgcaaca ccggtgacag gcaggctgcc ttgccctctc tacggcggct gggggcctgg     360
ctgcgggacc ctggggggca gcgcctggtg gtcctacacc tggaggaagt gacctgggag     420
ccaacaccct cgctgaggtt ccaggagccc ccgcctggag gagctggccc cccagagctg     480
gcgctgctgg tgctgtaccc tgggcctggc cctgaggtca ctgtgacgag ggctgggctg     540
ccgggtgccc agagcctctg cccctcccga gacacccgct acctggtgtt agcggtggac     600
cgccctgcgg gggcctggcg cggctccggg ctggccttga ccctgcagcc ccgcggagag     660
gactcccggc tgagtaccgc ccggctgcag gcactgctgt tcggcgacga ccaccgctgc     720
ttcacacgga tgacccccggc cctgctcctg ctgccgcggt ccgagcccgc gccgctgcct     780
gcgcacggcc agctggacac cgtgcccttc ccgccgccca ggccatccgc ggaactcgag     840
gagtcgccac ccagcgcaga ccccttcctg gagacgctca cgcgcctggt gcgggcgctg     900
cgggtccccc cggcccgggc ctccgcgccg cgcctggccc tggatccgga cgcgctggcc     960
ggcttcccgc agggcctagt caacctgtcg gacccgcgg cgctggagcg cctactcgac    1020
```

```
ggcgaggagc cgctgctgct gctgctgagg cccactgcgg ccaccaccgg ggatcctgcg    1080
cccctgcacg accccacgtc ggcgccgtgg gccacggccc tggcgcgccg cgtggctgct    1140
gaactgcaag cggcggctgc cgagctgcga agcctcccgg gtctgcctcc ggccacagcc    1200
ccgctgctgg cgcgcctgct cgcgctctgc ccaggtggcc ccggcggcct cggcgatccc    1260
ctgcgagcgc tgctgctcct gaaggcgctg cagggcctgc gcgtggagtg gcgcgggcgg    1320
gatccgcgcg ggccgggtcg ggcacggcgc agcgcggggg ccaccgccgc cgacgggccg    1380
tgcgcgctgc gcgagctcag cgtagacctc cgcgccgagc gctccgtact catccccgag    1440
acctaccagg ccaacaattg ccagggcgtg tgcggctggc ctcagtccga ccgcaacccg    1500
cgctacggca accacgtggt gctgctgctg aagatgcagg cccgtggggc cgccctggcg    1560
cgcccaccct gctgcgtgcc caccgcctac gcgggcaagc tgctcatcag cctgtcggag    1620
gagcgcatca gcgcgcacca cgtgcccaac atggtggcca ccgagtgtgg ctgccggtga    1680
```

<210> SEQ ID NO 2
<211> LENGTH: 1704
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atgaagtggg tgagcttcat cagcctgctg ttcctgttca gcagcgctta ctcccgcggt      60
gtgttccgcc gcagagcaga ggagccagct gtgggcacca gtggcctcat cttccgagaa     120
gacttggact ggcctccagg cagcccacaa gagcctctgt gcctggtggc actgggcggg     180
gacagcaatg gcagcagctc cccctgcgg gtggtggggg ctctaagcgc ctatgagcag     240
gccttcctgg gggccgtgca gagggcccgc tggggccccc gagacctggc caccttcggg     300
gtctgcaaca ccggtgacag gcaggctgcc ttgccctctc tacggcggct ggggcctgg     360 ctgcgggacc ctggggggca cgcctggtg gtcctacacc tggaggaagt gacctgggag     420
ccaacaccct cgctgaggtt ccaggagccc ccgcctggag gagctggccc cccagagctg     480
gcgctgctgg tgctgtaccc tgggcctggc cctgaggtca ctgtgacgag ggctgggctg     540
ccgggtgccc agagcctctg cccctcccga cacaccgct acctggtgtt agcggtggac     600
cgccctgcgg gggcctggcg cggctccggg ctggccttga ccctgcagcc ccgcggagag     660 gactccggc tgagtaccgc ccggctgcag gcactgctgt tcggcgacga ccaccgctgc     720
ttcacacgga tgaccccggc cctgctcctg ctgccgcggt ccgagcccgc gccgctgcct     780
gcgcacggcc agctggacac cgtgcccttc ccgccgccca ggccatccgc ggaactcgag     840
gagtcgccac ccagcgcaga ccccttcctg gagacgctca cgcgcctggt gcgggcgctg     900
cgggtccccc cggccggc ctccgcgccg cgcctggccc tggatccgga cgcgctggcc     960
ggcttcccgc agggcctagt caacctgtcg gaccccgcgg cgctggagcg cctactcgac    1020
ggcgaggagc cgctgctgct gctgctgagg cccactgcgg ccaccaccgg ggatcctgcg    1080
cccctgcacg accccacgtc ggcgccgtgg gccacggccc tggcgcgccg cgtggctgct    1140
gaactgcaag cggcggctgc cgagctgcga agcctcccgg gtctgcctcc ggccacagcc    1200
ccgctgctgg cgcgcctgct cgcgctctgc ccaggtggcc ccggcggcct cggcgatccc    1260
ctgcgagcgc tgctgctcct gaaggcgctg cagggcctgc gcgtggagtg gcgcgggcgg    1320
gatccgcgcg ggccgggtcg ggcacggcgc agcgactaca aggatgacga cgacaaggcg    1380
```

-continued

```
gggccaccg  ccgccgacgg  gccgtgcgcg  ctgcgcgagc  tcagcgtaga  cctccgcgcc   1440
gagcgctccg  tactcatccc  cgagacctac  caggccaaca  attgccaggg  cgtgtgcggc   1500
tggcctcagt  ccgaccgcaa  cccgcgctac  ggcaaccacg  tggtgctgct  gctgaagatg   1560
caggcccgtg  gggccgccct  ggcgcgccca  ccctgctgcg  tgcccaccgc  ctacgcgggc   1620
aagctgctca  tcagcctgtc  ggaggagcgc  atcagcgcgc  accacgtgcc  caacatggtg   1680
gccaccgagt  gtggctgccg  gtga                                             1704
```

<210> SEQ ID NO 3
<211> LENGTH: 560
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Glu Pro Ala Val
                20                  25                  30

Gly Thr Ser Gly Leu Ile Phe Arg Glu Asp Leu Asp Trp Pro Pro Gly
            35                  40                  45

Ser Pro Gln Glu Pro Leu Cys Leu Val Ala Leu Gly Gly Asp Ser Asn
        50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

Leu Ala Thr Phe Gly Val Cys Asn Thr Gly Asp Arg Gln Ala Ala Leu
                100                 105                 110

Pro Ser Leu Arg Arg Leu Gly Ala Trp Leu Arg Asp Pro Gly Gly Gln
            115                 120                 125

Arg Leu Val Val Leu His Leu Glu Glu Val Thr Trp Glu Pro Thr Pro
130                 135                 140

Ser Leu Arg Phe Gln Glu Pro Pro Gly Gly Ala Gly Pro Pro Glu
145                 150                 155                 160

Leu Ala Leu Leu Val Leu Tyr Pro Gly Pro Gly Pro Glu Val Thr Val
                165                 170                 175

Thr Arg Ala Gly Leu Pro Gly Ala Gln Ser Leu Cys Pro Ser Arg Asp
                180                 185                 190

Thr Arg Tyr Leu Val Leu Ala Val Asp Arg Pro Ala Gly Ala Trp Arg
            195                 200                 205

Gly Ser Gly Leu Ala Leu Thr Leu Gln Pro Arg Gly Glu Asp Ser Arg
        210                 215                 220

Leu Ser Thr Ala Arg Leu Gln Ala Leu Leu Phe Gly Asp Asp His Arg
225                 230                 235                 240

Cys Phe Thr Arg Met Thr Pro Ala Leu Leu Leu Leu Pro Arg Ser Glu
                245                 250                 255

Pro Ala Pro Leu Pro Ala His Gly Gln Leu Asp Thr Val Pro Phe Pro
                260                 265                 270

Pro Pro Arg Pro Ser Ala Glu Leu Glu Glu Ser Pro Pro Ser Ala Asp
            275                 280                 285

Pro Phe Leu Glu Thr Leu Thr Arg Leu Val Arg Ala Leu Arg Val Pro
        290                 295                 300
```

Pro Ala Arg Ala Ser Ala Pro Arg Leu Ala Leu Asp Pro Asp Ala Leu
305                 310                 315                 320

Ala Gly Phe Pro Gln Gly Leu Val Asn Leu Ser Asp Pro Ala Ala Leu
            325                 330                 335

Glu Arg Leu Leu Asp Gly Glu Pro Leu Leu Leu Leu Arg Pro
        340                 345                 350

Thr Ala Ala Thr Thr Gly Asp Pro Ala Pro Leu His Asp Pro Thr Ser
        355                 360                 365

Ala Pro Trp Ala Thr Ala Leu Ala Arg Arg Val Ala Ala Glu Leu Gln
        370                 375                 380

Ala Ala Ala Ala Glu Leu Arg Ser Leu Pro Gly Leu Pro Pro Ala Thr
385                 390                 395                 400

Ala Pro Leu Leu Ala Arg Leu Leu Ala Leu Cys Pro Gly Gly Pro Gly
                405                 410                 415

Gly Leu Gly Asp Pro Leu Arg Ala Leu Leu Leu Lys Ala Leu Gln
            420                 425                 430

Gly Leu Arg Val Glu Trp Arg Gly Arg Asp Pro Arg Gly Pro Gly Arg
            435                 440                 445

Ala Gln Arg Ser Ala Gly Ala Thr Ala Ala Asp Gly Pro Cys Ala Leu
    450                 455                 460

Arg Glu Leu Ser Val Asp Leu Arg Ala Glu Arg Ser Val Leu Ile Pro
465                 470                 475                 480

Glu Thr Tyr Gln Ala Asn Asn Cys Gln Gly Val Cys Gly Trp Pro Gln
            485                 490                 495

Ser Asp Arg Asn Pro Arg Tyr Gly Asn His Val Val Leu Leu Leu Lys
            500                 505                 510

Met Gln Val Arg Gly Ala Ala Leu Ala Arg Pro Pro Cys Cys Val Pro
        515                 520                 525

Thr Ala Tyr Ala Gly Lys Leu Leu Ile Ser Leu Ser Glu Glu Arg Ile
        530                 535                 540

Ser Ala His His Val Pro Asn Met Val Ala Thr Glu Cys Gly Cys Arg
545                 550                 555                 560

<210> SEQ ID NO 4
<211> LENGTH: 559
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Lys Trp Val Thr Phe Ile Ser Leu Leu Phe Leu Phe Ser Ser Ala
1               5                   10                  15

Tyr Ser Arg Gly Val Phe Arg Arg Ala Glu Glu Pro Ala Val Gly
            20                  25                  30

Thr Ser Gly Leu Ile Phe Arg Glu Asp Leu Asp Trp Pro Pro Gly Ser
        35                  40                  45

Pro Gln Glu Pro Leu Cys Leu Val Ala Leu Gly Gly Asp Ser Asn Gly
    50                  55                  60

Ser Ser Ser Pro Leu Arg Val Val Gly Ala Leu Ser Ala Tyr Glu Gln
65                  70                  75                  80

Ala Phe Leu Gly Ala Val Gln Arg Ala Arg Trp Gly Pro Arg Asp Leu
                85                  90                  95

Ala Thr Phe Gly Val Cys Asn Thr Gly Asp Arg Gln Ala Ala Leu Pro

```
                100                 105                 110
Ser Leu Arg Arg Leu Gly Ala Trp Leu Arg Asp Pro Gly Gly Gln Arg
            115                 120                 125

Leu Val Val Leu His Leu Glu Glu Val Thr Trp Glu Pro Thr Pro Ser
        130                 135                 140

Leu Arg Phe Gln Glu Pro Pro Gly Gly Ala Gly Pro Pro Glu Leu
145                 150                 155                 160

Ala Leu Leu Val Leu Tyr Pro Gly Pro Gly Pro Glu Val Thr Val Thr
                165                 170                 175

Arg Ala Gly Leu Pro Gly Ala Gln Ser Leu Cys Pro Ser Arg Asp Thr
            180                 185                 190

Arg Tyr Leu Val Leu Ala Val Asp Arg Pro Ala Gly Ala Trp Arg Gly
        195                 200                 205

Ser Gly Leu Ala Leu Thr Leu Gln Pro Arg Gly Glu Asp Ser Arg Leu
    210                 215                 220

Ser Thr Ala Arg Leu Gln Ala Leu Leu Phe Gly Asp Asp His Arg Cys
225                 230                 235                 240

Phe Thr Arg Met Thr Pro Ala Leu Leu Leu Pro Arg Ser Glu Pro
                245                 250                 255

Ala Pro Leu Pro Ala His Gly Gln Leu Asp Thr Val Pro Phe Pro Pro
            260                 265                 270

Pro Arg Pro Ser Ala Glu Leu Glu Ser Pro Pro Ser Ala Asp Pro
        275                 280                 285

Phe Leu Glu Thr Leu Thr Arg Leu Val Arg Ala Leu Arg Val Pro Pro
    290                 295                 300

Ala Arg Ala Ser Ala Pro Arg Leu Ala Leu Asp Pro Asp Ala Leu Ala
305                 310                 315                 320

Gly Phe Pro Gln Gly Leu Val Asn Leu Ser Asp Pro Ala Ala Leu Glu
                325                 330                 335

Arg Leu Leu Asp Gly Glu Glu Pro Leu Leu Leu Leu Arg Pro Thr
            340                 345                 350

Ala Ala Thr Thr Gly Asp Pro Ala Pro Leu His Asp Pro Thr Ser Ala
        355                 360                 365

Pro Trp Ala Thr Ala Leu Ala Arg Val Ala Ala Glu Leu Gln Ala
    370                 375                 380

Ala Ala Ala Glu Leu Arg Ser Leu Pro Gly Leu Pro Pro Ala Thr Ala
385                 390                 395                 400

Pro Leu Leu Ala Arg Leu Leu Ala Leu Cys Pro Gly Gly Pro Gly Gly
                405                 410                 415

Leu Gly Asp Pro Leu Arg Ala Leu Leu Leu Lys Ala Leu Gln Gly
            420                 425                 430

Leu Arg Val Glu Trp Arg Gly Arg Asp Pro Arg Gly Pro Gly Arg Ala
        435                 440                 445

Arg Arg Ser Ala Gly Ala Thr Ala Ala Asp Gly Pro Cys Ala Leu Arg
    450                 455                 460

Glu Leu Ser Val Asp Leu Arg Ala Glu Arg Ser Val Leu Ile Pro Glu
465                 470                 475                 480

Thr Tyr Gln Ala Asn Asn Cys Gln Gly Val Cys Gly Trp Pro Gln Ser
                485                 490                 495

Asp Arg Asn Pro Arg Tyr Gly Asn His Val Val Leu Leu Lys Met
            500                 505                 510

Gln Val Arg Gly Ala Ala Leu Ala Arg Pro Pro Cys Cys Val Pro Thr
        515                 520                 525
```

Ala Tyr Ala Gly Lys Leu Leu Ile Ser Leu Ser Glu Glu Arg Ile Ser
            530                 535                 540

Ala His His Val Pro Asn Met Val Ala Thr Glu Cys Gly Cys Arg
545                 550                 555

<210> SEQ ID NO 5
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Trp Val Thr Phe Ile Ser Leu Leu Phe Leu Phe Ser Ser Ala
1               5                   10                  15

Tyr Ser Arg Gly Val Phe Arg Arg Ala Glu Glu Pro Ala Val Gly
                20                  25                  30

Thr Ser Gly Leu Ile Phe Arg Glu Asp Leu Asp Trp Pro Pro Gly Ser
            35                  40                  45

Pro Gln Glu Pro Leu Cys Leu Val Ala Leu Gly Gly Asp Ser Asn Gly
        50                  55                  60

Ser Ser Ser Pro Leu Arg Val Val Gly Ala Leu Ser Ala Tyr Glu Gln
65                  70                  75                  80

Ala Phe Leu Gly Ala Val Gln Arg Ala Arg Trp Gly Pro Arg Asp Leu
                85                  90                  95

Ala Thr Phe Gly Val Cys Asn Thr Gly Asp Arg Gln Ala Ala Leu Pro
            100                 105                 110

Ser Leu Arg Arg Leu Gly Ala Trp Leu Arg Asp Pro Gly Gly Gln Arg
        115                 120                 125

Leu Val Val Leu His Leu Glu Glu Val Thr Trp Glu Pro Thr Pro Ser
130                 135                 140

Leu Arg Phe Gln Glu Pro Pro Pro Gly Gly Ala Gly Pro Pro Glu Leu
145                 150                 155                 160

Ala Leu Leu Val Leu Tyr Pro Gly Pro Gly Pro Glu Val Thr Val Thr
                165                 170                 175

Arg Ala Gly Leu Pro Gly Ala Gln Ser Leu Cys Pro Ser Arg Asp Thr
            180                 185                 190

Arg Tyr Leu Val Leu Ala Val Asp Arg Pro Ala Gly Ala Trp Arg Gly
        195                 200                 205

Ser Gly Leu Ala Leu Thr Leu Gln Pro Arg Gly Glu Asp Ser Arg Leu
210                 215                 220

Ser Thr Ala Arg Leu Gln Ala Leu Leu Phe Gly Asp Asp His Arg Cys
225                 230                 235                 240

Phe Thr Arg Met Thr Pro Ala Leu Leu Leu Pro Arg Ser Glu Pro
                245                 250                 255

Ala Pro Leu Pro Ala His Gly Gln Leu Asp Thr Val Pro Phe Pro Pro
            260                 265                 270

Pro Arg Pro Ser Ala Glu Leu Glu Glu Ser Pro Pro Ser Ala Asp Pro
        275                 280                 285

Phe Leu Glu Thr Leu Thr Arg Leu Val Arg Ala Leu Arg Val Pro Pro
    290                 295                 300

Ala Arg Ala Ser Ala Pro Arg Leu Ala Leu Asp Pro Asp Ala Leu Ala
305                 310                 315                 320

Gly Phe Pro Gln Gly Leu Val Asn Leu Ser Asp Pro Ala Ala Leu Glu

```
                    325                 330                 335
Arg Leu Leu Asp Gly Glu Glu Pro Leu Leu Leu Leu Arg Pro Thr
                340                 345                 350

Ala Ala Thr Thr Gly Asp Pro Ala Pro Leu His Asp Pro Thr Ser Ala
                355                 360                 365

Pro Trp Ala Thr Ala Leu Ala Arg Arg Val Ala Ala Glu Leu Gln Ala
        370                 375                 380

Ala Ala Ala Glu Leu Arg Ser Leu Pro Gly Leu Pro Pro Ala Thr Ala
385                 390                 395                 400

Pro Leu Leu Ala Arg Leu Leu Ala Leu Cys Pro Gly Gly Pro Gly Gly
                405                 410                 415

Leu Gly Asp Pro Leu Arg Ala Leu Leu Leu Lys Ala Leu Gln Gly
                420                 425                 430

Leu Arg Val Glu Trp Arg Gly Arg Asp Pro Arg Gly Pro Gly Arg Ala
                435                 440                 445

Arg Arg Ser Asp Tyr Lys Asp Asp Asp Lys Ala Gly Ala Thr Ala
        450                 455                 460

Ala Asp Gly Pro Cys Ala Leu Arg Glu Leu Ser Val Asp Leu Arg Ala
465                 470                 475                 480

Glu Arg Ser Val Leu Ile Pro Glu Thr Tyr Gln Ala Asn Asn Cys Gln
                485                 490                 495

Gly Val Cys Gly Trp Pro Gln Ser Asp Arg Asn Pro Arg Tyr Gly Asn
                500                 505                 510

His Val Val Leu Leu Leu Lys Met Gln Val Arg Gly Ala Ala Leu Ala
                515                 520                 525

Arg Pro Pro Cys Cys Val Pro Thr Ala Tyr Ala Gly Lys Leu Leu Ile
        530                 535                 540

Ser Leu Ser Glu Glu Arg Ile Ser Ala His His Val Pro Asn Met Val
545                 550                 555                 560

Ala Thr Glu Cys Gly Cys Arg
                565

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Lys Trp Val Thr Phe Ile Ser Leu Leu Phe Leu Phe Ser Ser Ala
1               5                   10                  15

Tyr Ser Arg Gly Val Phe Arg Arg
            20

<210> SEQ ID NO 7
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atgaagtggg tgagcttcat cagcctgctg ttcctgttca gcagcgctta ctcccgcggt     60
gtgttccgcc gcagagca                                                  78
```

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Tyr Lys Asp Asp Asp Asp Lys
1               5

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Lys Trp Val Thr Phe Ile Ser Leu Leu Phe Leu Phe Ser Ser Ala
1               5                   10                  15

Tyr Ser

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Lys Trp Val Ser Phe Ile Ser Leu Leu Phe Leu Phe Ser Ser Ala
1               5                   10                  15

Tyr Ser

<210> SEQ ID NO 11
<211> LENGTH: 21
<212> TYPE: PRT
<213> ORGANISM: Homo sapiens

<400> SEQUENCE: 11

Met Lys Val Ser Val Ala Ala Leu Ser Cys Leu Met Leu Val Thr Ala
1               5                   10                  15

Leu Gly Ser Gln Ala
            20

<210> SEQ ID NO 12
<211> LENGTH: 17
<212> TYPE: PRT
<213> ORGANISM: Unknown
<220> FEATURE:
<223> OTHER INFORMATION: Description of Unknown:
      Stanniocalcin signal peptide

<400> SEQUENCE: 12

Met Leu Gln Asn Ser Ala Val Leu Leu Leu Leu Val Ile Ser Ala Ser
1               5                   10                  15

Ala

<210> SEQ ID NO 13
<211> LENGTH: 19

```
<212> TYPE: PRT
<213> ORGANISM: Unknown
<220> FEATURE:
<223> OTHER INFORMATION: Description of Unknown:
      Invertase signal peptide

<400> SEQUENCE: 13

Met Leu Leu Gln Ala Phe Leu Phe Leu Leu Ala Gly Phe Ala Ala Lys
1               5                   10                  15

Ile Ser Ala

<210> SEQ ID NO 14
<211> LENGTH: 24
<212> TYPE: PRT
<213> ORGANISM: Unknown
<220> FEATURE:
<223> OTHER INFORMATION: Description of Unknown:
      Hybrid signal peptide

<400> SEQUENCE: 14

Met Lys Trp Val Ser Phe Ile Ser Leu Leu Phe Leu Phe Ser Ser Ala
1               5                   10                  15

Tyr Ser Arg Ser Leu Glu Lys Arg
            20

<210> SEQ ID NO 15
<211> LENGTH: 24
<212> TYPE: PRT
<213> ORGANISM: Unknown
<220> FEATURE:
<223> OTHER INFORMATION: Description of Unknown:
      HSA/MFalpha-1 hybrid signal peptide

<400> SEQUENCE: 15

Met Lys Trp Val Ser Phe Ile Ser Leu Leu Phe Leu Phe Ser Ser Ala
1               5                   10                  15

Tyr Ser Arg Ser Leu Asp Lys Arg
            20

<210> SEQ ID NO 16
<211> LENGTH: 21
<212> TYPE: PRT
<213> ORGANISM: Unknown
<220> FEATURE:
<223> OTHER INFORMATION: Description of Unknown:
      K. Lactis killer/MFalpha-1 fusion leader peptide

<400> SEQUENCE: 16

Met Asn Ile Phe Tyr Ile Phe Leu Phe Leu Leu Ser Phe Val Gln Gly
1               5                   10                  15

Ser Leu Asp Lys Arg
            20

<210> SEQ ID NO 17
<211> LENGTH: 19
<212> TYPE: PRT
<213> ORGANISM: Unknown
<220> FEATURE:
<223> OTHER INFORMATION: Description of Unknown:
      Immunoglobulin Ig signal peptide

<400> SEQUENCE: 17

Met Gly Trp Ser Cys Ile Ile Leu Phe Leu Val Ala Thr Ala Thr Gly
1               5                   10                  15

Val His Ser
```

```
<210> SEQ ID NO 18
<211> LENGTH: 29
<212> TYPE: PRT
<213> ORGANISM: Unknown
<220> FEATURE:
<223> OTHER INFORMATION: Description of Unknown:
      Fibulin B precursor signal peptide

<400> SEQUENCE: 18

Met Glu Arg Ala Ala Pro Ser Arg Arg Val Pro Leu Pro Leu Leu Leu
1               5                   10                  15

Leu Gly Gly Leu Ala Leu Leu Ala Ala Gly Val Asp Ala
            20                  25

<210> SEQ ID NO 19
<211> LENGTH: 22
<212> TYPE: PRT
<213> ORGANISM: Unknown
<220> FEATURE:
<223> OTHER INFORMATION: Description of Unknown:
      Clusterin precursor signal peptide

<400> SEQUENCE: 19

Met Met Lys Thr Leu Leu Leu Phe Val Gly Leu Leu Leu Thr Trp Glu
1               5                   10                  15

Ser Gly Gln Val Leu Gly
            20

<210> SEQ ID NO 20
<211> LENGTH: 21
<212> TYPE: PRT
<213> ORGANISM: Unknown
<220> FEATURE:
<223> OTHER INFORMATION: Description of Unknown:
      Insulin-like growth factor-binding protein 4
      signal peptide

<400> SEQUENCE: 20

Met Leu Pro Leu Cys Leu Val Ala Ala Leu Leu Leu Ala Ala Gly Pro
1               5                   10                  15

Gly Pro Ser Leu Gly
            20

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Gly Asp Ser
1
```